(12) United States Patent
Foster et al.

(10) Patent No.: US 8,852,603 B2
(45) Date of Patent: *Oct. 7, 2014

(54) INHIBITION OF SECRETION FROM NON-NEURONAL CELLS

(75) Inventors: Keith Alan Foster, Abingdon (GB); John Andrew Chaddock, Abingdon (GB); Conrad Padraig Quinn, Abingdon (GB); John Robert Purkiss, Abingdon (GB)

(73) Assignee: Syntaxin Limited, Abingdon, Oxfordshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/344,776

(22) Filed: Jan. 6, 2012

(65) Prior Publication Data

US 2012/0101027 A1 Apr. 26, 2012

Related U.S. Application Data

(63) Continuation of application No. 13/022,184, filed on Feb. 7, 2011, now abandoned, which is a continuation of application No. 11/066,648, filed on Jun. 1, 2007, now abandoned, which is a continuation-in-part of application No. 11/327,855, filed on Jan. 9, 2006, now abandoned, which is a continuation of application No. 10/088,665, filed as application No. PCT/GB00/03681 on Sep. 25, 2000, now abandoned.

(30) Foreign Application Priority Data

Sep. 23, 1999 (GB) .................................. 9922558.3

(51) Int. Cl.

| | |
|---|---|
| A61K 39/08 | (2006.01) |
| C07K 14/54 | (2006.01) |
| C07K 14/50 | (2006.01) |
| C07K 14/33 | (2006.01) |
| C07K 14/48 | (2006.01) |
| A61K 38/18 | (2006.01) |
| A61K 47/48 | (2006.01) |
| C07K 16/12 | (2006.01) |
| A61K 38/48 | (2006.01) |

(52) U.S. Cl.
CPC ....... A61K 38/1808 (2013.01); A61K 47/48246 (2013.01); C07K 16/1282 (2013.01); C07K 2319/00 (2013.01); A61K 38/4886 (2013.01)
USPC .................. 424/192.1; 424/239.1; 424/193.1; 424/178.1; 424/133.1; 424/143.1; 424/152.1; 530/350; 530/388.22

(58) Field of Classification Search
None
See application file for complete search history.

(56) References Cited

U.S. PATENT DOCUMENTS

| | | | |
|---|---|---|---|
| 4,792,447 A | 12/1988 | Uhr et al. | |
| 5,190,873 A * | 3/1993 | Lernhardt et al. | 435/177 |
| 5,196,193 A * | 3/1993 | Carroll | 424/172.1 |
| 5,614,488 A * | 3/1997 | Bacha | 514/16.8 |
| 5,668,255 A | 9/1997 | Murphy | |
| 5,766,591 A | 6/1998 | Brooks et al. | |
| 5,874,080 A * | 2/1999 | Hebert et al. | 424/145.1 |
| 6,632,440 B1* | 10/2003 | Quinn et al. | 424/239.1 |
| 2003/0180289 A1* | 9/2003 | Foster et al. | 424/132.1 |
| 2004/0072270 A1* | 4/2004 | Fernandez-Salas et al. | 435/7.32 |
| 2005/0245446 A1* | 11/2005 | Hailes et al. | 514/12 |

FOREIGN PATENT DOCUMENTS

| | | |
|---|---|---|
| DE | 19735105 A1 | 3/1999 |
| WO | 9109871 A1 | 7/1991 |
| WO | 9215327 A1 | 9/1992 |
| WO | 9304191 A1 | 3/1993 |
| WO | 9315766 A1 | 8/1993 |
| WO | 9421300 A2 | 9/1994 |
| WO | 9612802 A1 | 5/1996 |
| WO | 9633273 A1 | 10/1996 |
| WO | 9807864 A1 | 2/1998 |
| WO | 9808540 A1 | 3/1998 |
| WO | 9958571 A2 | 11/1999 |
| WO | 0004926 A2 | 2/2000 |
| WO | 0010598 A2 | 3/2000 |
| WO | 0033863 A2 | 6/2000 |
| WO | 0061192 A2 | 10/2000 |
| WO | 0061195 A1 | 10/2000 |
| WO | 0062814 A2 | 10/2000 |
| WO | WO00/71096 * | 11/2000 |
| WO | 0074703 A2 | 12/2000 |
| WO | 0121213 A2 | 3/2001 |
| WO | 2006059113 A2 | 6/2006 |

OTHER PUBLICATIONS

Uhl et al, J immunology 142(5): 1576-1581, 1989.*
Takeyama et al, Proc Natl Acad Sci 96(6): 3081-3086, Mar. 1999.*
Barnes et al, J Allergy Clin Immunol 104: S10-17, Aug. 1999.*
Colman et al., In Research in Immunology (145(1):33-36, 1994.*
Nath et al., J Immunology 152: 1370-1379, 1994.*
Imamura et al., Molecular and Cellular Biology 9(5): 2239-2243, May 1989.*

(Continued)

*Primary Examiner* — Phuong Huynh
(74) *Attorney, Agent, or Firm* — Morris Manning & Martin, LLP; Christopher W. Raimund

(57) ABSTRACT

The present invention relates to treatment of disease by inhibition of cellular secretory processes, to agents and compositions therefor, and to manufacture of those agents and compositions. The present invention relates particularly, to treatment of disease dependent upon the exocytotic activity of endocrine cells, exocrine cells, inflammatory cells, cells of the immune system, cells of the cardiovascular system and bone cells.

6 Claims, 16 Drawing Sheets

(56) References Cited

OTHER PUBLICATIONS

Foster et al., J. Neurotoxicity Research 9(2-3): 101-107, Apr. 2006.
Kessler et al., Clin. Cancer Res 11(17): 6317-6324, Sep. 1, 2005.
Hart et al., J. Biol. Chem. 269(17): 12468-12474, 1994.
Schneider et al., FEBS Letters 458: 329-332, 1999.
Chica et al., Curr Opin Biotechnol 16(4): 378-84, Aug. 2005.
Witkowski, et al. Biochemistry 38(36): 11643-50, Sep. 1999.
Seffernick, et al., J. Bacteriol 183(8): 2405-10, Apr. 2001.
Chaddock, et al., "Inhibition of Vesicular Secretion in Both Neuronal and Nonneuronal Cells by a Retargeted Endopeptidase Derivative of *Clostridium botulinum* Neurotoxin Type A: Infection and Immunity" American Society for Microbiology, 68(5), May 2000, pp. 2587-2593.
Nemoz-Gaillard, et al. "Expression of SNARE Proteins in Enteroendocrine Cell Lines and Functional Role of Tetanus Toxin-Sensitive Proteins in Cholecystokin Release" FEBS Letters, vol. 425, 1998, pp. 66-70.
Bizzini "Investigation of the Mode of Action of Tetanus Toxin with the Aid of Hybrid Molecules Consisting in Part of Tetanus Toxin-derived Fragments" Academic Press London, 1984, pp. 437-434.
Van Damme, et al. "The Neutrophil-activating Proteins Interleukin 8 and β-thromboglobulin: in vitro and in vivo comparison of NH2-Terminally Processed Forms" Eur. J. Immunno., Sep. 1990, pp. 2113-2118.
Stryer, et al., Biochemistry, Third Edition, W.H. Freeman Company, New York, 1998, pp. 31-33.
Ngo et al. "Computational Complexity, Protein Structure Prediction, and the Levinthal Paradox" The Protein Folding Problem and Tertiary Structure Prediction, Boston, 1994, pp. 491-495.
Ray et al., Cytokine, 9(8), 1997, pp. 587-596.
Van Noort et al., International Review of Cytology, vol. 178, 1998, pp. 127-205.
Gerald R. Dubois et al. "Human Eosinophils Constitutively Express a Functional Interleukin-4 Receptor: Interleukin-4-Induced Priming of Chemotactic Responses and Induction of PI-3 Kinase Activity" Am. J. Respir. Cell Mol. Biol. vol. 19, pp. 691-699, 1998.
Aram E. Elovic, et al. "IL-4-Dependent Regulation of TGF- and TGF-β 1 Expression in Human Eosinophils" J Immunol 1998; 160:6121-6127; http://www.jimmunol.org/content/160/12/6121.
Marc E. Rothenberg "Mechanisms of Disease, Eosinophilia" The New England Journal of Medicine, pp. 1592-1600, May 28, 1998.
By Ji-Liang Gao et al. "Impaired Host Defense, Hematopoiesis, Granulomatous Inflammation and Type 1-Type 2 Cytokine Balance in Mice Lacking CC Chemokine Receptor 1" The Journal of Experimental Medicine • vol. 185, No. 11, Jun. 2, 1997 1959-1968.
Abhi Parikh et al. "Clinical review, Fortnightly review Seasonal allergic rhinitis" BMJ, vol. 314, 10 May 1997, pp. 1392-1395.
Poh-Chun Tai, et al. "Toxic effects of human eosinophil secretion products on isolated rat heart cells in vitro " Biochem. J. (1982) 204, pp. 75-80.
G. Torpier, et al. "Eosinophilic gastroenteritis: ultrastructural evidence for a selective release of eosinophil major basic protein" Clin. exp. Immunol. (1988) 74, pp. 404-408.
David T. W. Wong, et al. "Human Eosinophils Express Transforming Growth Factor α" J . Exp. Med., vol. 172, Sep. 1990, pp. 673-681.
Bernhard Moser, et al. "Neutrophil-Activating Properties of the Melanoma Growth-Stimulatory Activity" J. Exp. Med., vol. 171, May 1990, pp. 1797-1802.
Alfred Walz, et al. "Structure and Neutrophil-activating Properties of a Novel Inflammatory Peptide (ENA-78) with Homology to Interleukin 8" J. Exp. Med., vol. 174, Dec. 1991, pp. 1355-1362.
Yoshimi Hatano, et al. "Macrophage inflammatory protein 1 alpha expression by synovial fluid neutrophils in rheumatoid arthritis" Ann. Rheum. Dis., 1999; vol. 58, pp. 297-302.
Tsuyoshi Kasama, et al. "Synovial fluid neutrophil expression of interleukin-8 in rheumatoid arthritis" Japanese Journal ofRheumatology, vol. 9, No. 2, pp. 175-187 (1999).
RenC de Waal Malefyt, et al. "Effects of IL-13 on Phenotype, Cytokine Production, and Cytotoxic Function of Human Monocytes" The Journal of Immunology, vol. 151, 6370-6381, No. 11, Dec. 1, 1993.
Antal Rot, et al. "RANTES and Macrophage Inflammatory Protein lot Induce the Migration and Activation of Normal Human Eosinophil Granulocytes" J. Exp. Med., vol. 176, Dec. 1992, pp. 1489-1495.
Raffaella Bonecchi, et al. "Divergent Effects of Interleukin-4 and Interferon-g on Macrophage-Derived Chemokine Production: An Amplification Circuit of Polarized T Helper 2 Responses" Blood, vol. 92, no. 8 (Oct. 15), 1998: pp. 2668-2671.
Valerie A. Fadok, et al. "Macrophages That Have Ingested Apoptotic Cells In Vitro Inhibit Proinflammatory Cytokine Production Through Autocrine/Paracrine Mechanisms Involving TGFβ, PGE2, and PAF" J. Clin. Invest., vol. 101, No. 4, Feb. 1998, pp. 890-898.
Dyana K. Dalton, et al. "Multiple Defects of Immune Cell Function in Mice with Disrupted Interferon-y Genes" Science Vol. 259 Mar. 19, 1993.
Elizabeth J. Kovacs "Fibrogenic cytokines: the role of immune mediators in the development of scar tissue" Immunology Today, vol. 12, No. 1 1991, pp. 17-23.
Carl F. Nathan, et al. "Administration of recombinant interferon y to cancer patients enhances monocyte secretion of hydrogen peroxide" Proc. Natl. Acad. Sci. USA, vol. 82, pp. 8686-8690, Dec. 1985.
Marco Baggiolini, et al. "Neutrophil-activating Peptide-1/ Interleukin 8, a Novel Cytokine That Activates Neutrophils" J. Clin. Invest., vol. 84, Oct. 1989, pp. 1045-1049.
Norton S. Taichman, et al. "Human neutrophils secrete vascular endothelial growth factor" Journal of Leukocyte Biology, vol. 62, Sep. 1997, 397-400.
T.C. Theoharides, Ph.D., M.D. "Mast Cells: The Immune Gate to the Brain" Life Sciences, vol. 46, pp. 607-617, 1990.
Stephen J. Galli, et al. "Cytokine production by mast cells and basophils" Current Opinion in Immunology 1991, vol. 3 pp. 865-873.
Stephen J Galli, et al. "Mast cells as sentinels of innate immunity" Current Opinion in Immunology, 1999, 11:53-59.
Galli SJ, et al. "Mast-cell-leukocyte cytokine cascades in allergic inflammation" Allergy, 1995 vol. 511, pp. 851-862.
John R. Gordon, et al. "Mast cells as a source of multifunctional cytokines" Immunology Today, vol. 11, No. 12 1990, pp. 458-464.
Yoshikazu Inoue, et al. "Human Mast Cell Basic Fibroblast Growth Factor in Pulmonary Fibrotic Disorders" American Journal of Pathology, vol. 149, No. 6, Dec. 1996, pp. 2037-2054.
A. Leon, et al. "Mast cells synthesize, store, and release nerve growth factor" Proc. Nati. Acad. Sci. USA, vol. 91, pp. 3739-3743, Apr. 1994.
Douglas S Robinson et al. "Cytokines in asthma" Thorax BMJ, 1993, vol. 48, pp. 845-853.
Fen-yu Jin, et al. "Secretory Leukocyte Protease Inhibitor: A Macrophage Product Induced by and Antagonistic to Bacterial Lipopolysaccharide" Cell, vol. 88, 417-426, Feb. 7, 1997.

* cited by examiner

SEQUENCE LISTING

```
<160> NUMBER OF SEQ ID NOS: 33

<210> SEQ ID NO 1
<211> LENGTH: 2631
<212> TYPE: DNA
<213> ORGANISM: Unknown
<220> FEATURE:
<223> OTHER INFORMATION: DNA sequence of LHN/B

<400> SEQUENCE: 1
ggatccatgc cggttaccat caacaacttc aactacaacg acccgatcga caacaacaac      60
atcattatga tggaaccgcc gttcgcacgt ggtaccggac gttactacaa ggcttttaag     120
atcaccgacc gtatctggat catcccggaa cgttacacct tcggttacaa acctgaggac     180
ttcaacaaga gtagcgggat tttcaatcgt gacgtctgcg agtactatga tccagattat     240
ctgaatacca acgataagaa gaacatattc cttcagacta tgattaaact cttcaaccgt     300
atcaaaagca aaccgctcgg tgaaaaactc ctcgaaatga ttatcaacgg tatcccgtac     360
ctcggtgacc gtcgtgtccc gcttgaagag ttcaacacca acatcgcaag cgtcaccgtc     420
aacaaactca tcagcaaccc aggtgaagtc gaacgtaaaa aaggtatctt cgcaaacctc     480
atcatcttcg gtccgggtcc ggtcctcaac gaaaacgaaa ccatcgacat cggtatccag     540
aaccacttcg caagccgtga aggtttcggt ggtatcatgc agatgaaatt ctgcccggaa     600
tacgtcagtg tcttcaacaa cgtccaggaa aacaaaggtg caagcatctt caaccgtcgt     660
ggttacttca gcgacccggc actcatcctc atgcatgaac tcatccacgt cctccacggt     720
ctctacggta tcaaagttga cgacctcccg atcgtcccga acgagaagaa attcttcatg     780
cagagcaccg acgcaatcca ggctgaggaa ctctacacct tcggtggcca agacccaagt     840
atcataaccc cgtccaccga caaaagcatc tacgacaaag tcctccagaa cttcaggggt     900
atcgtggaca gactcaacaa agtcctcgtc tgcatcagcg acccgaacat caatatcaac     960
atatacaaga acaagttcaa agacaagtac aaattcgtcg aggacagcga aggcaaatac    1020
agcatcgacg tagaaagttt cgacaagctc tacaaaagcc tcatgttcgg tttcaccgaa    1080
accaacatcg ccgagaacta caagatcaag acaagggcaa gttacttcag cgacagcctc    1140
ccgcctgtca aaatcaagaa cctcttagac aacgagattt acacaattga gagggcttc    1200 aacatcagtg acaaagacat ggagaaggaa tacagaggtc agaacaaggc tatcaacaaa    1260
caggcatacg aggagatcag caaagaacac ctcgcagtct acaagatcca gatgtgcgtc    1320
gacgaagaaa agctgtacga cgacgacgac aaagaccgtt ggggttcttc gctgcagtgc    1380
atcgacgttg acaacgaaga cctgttcttc atcgctgaca aaacagctt cagtgacgac    1440 ctgagcaaaa cgaacgtat cgaatacaac acccagagca actacatcga aaacgacttc    1500
ccgatcaacg aactgatcct ggacaccgac ctgataagta aaatcgaact gccgagcgaa    1560
aacaccgaaa gtctgaccga cttcaacgtt gacgttccgg tttacgaaaa acagccggct    1620
atcaagaaaa tcttcaccga cgaaaacacc atcttccagt acctgtacag ccagaccttc    1680
ccgctggaca tccgtgacat cagtctgacc agcagtttcg acgacgctct gctgttcagc    1740
aacaaagttt acagtttctt cagcatggac tacatcaaaa ccgctaacaa agttgttgaa    1800
```

```
gcagggctgt tcgctggttg ggttaaacag atcgttaacg acttcgttat cgaagctaac   1860
aaaagcaaca ctatggacaa aatcgctgac atcagtctga tcgttccgta catcggtctg   1920
gctctgaacg ttggtaacga aaccgctaaa ggtaactttg aaaacgcttt cgagatcgct   1980
ggtgcaagca tcctgctgga gttcatcccg gaactgctga tcccggttgt tggtgctttc   2040
ctgctggaaa gttacatcga caacaaaaac aagatcatca aaaccatcga caacgctctg   2100
accaaacgta acgaaaaatg gagtgatatg tacggtctga tcgttgctca gtggctgagc   2160
accgtcaaca cccagttcta caccatcaaa gaaggtatgt acaaagctct gaactaccag   2220
gctcaggctc tggaagagat catcaaatac cgttacaaca tctacagtga aggaaaaag   2280 agtaacatca acatcgactt caacgacatc aacagcaaac tgaacgaagg tatcaaccag   2340
gctatcgaca catcaacaa cttcatcaac ggttgcagtg ttagctacct gatgaagaag   2400
atgatcccgc tggctgttga aaaactgctg gacttcgaca cacccctgaa aagaacctg   2460 ctgaactaca tcgacgaaaa caagctgtac ctgatcggta gtgctgaata cgaaaaagt   2520 aaagtgaaca aatacctgaa gaccatcatg ccgttcgacc tgagtatcta caccaacgac   2580
accatcctga tcgaaatgtt caacaaatac aactctctag actagaagct t            2631
```

<210> SEQ ID NO 2
<211> LENGTH: 2620
<212> TYPE: DNA
<213> ORGANISM: Unknown
<220> FEATURE:
<223> OTHER INFORMATION: DNA sequence of LHN/C

<400> SEQUENCE: 2

```
ggatccatgc cgatcaccat caacaacttc aactacagcg atccggtgga taacaaaaac     60
atcctgtacc tggataccca tctgaatacc ctggcgaacg aaccggaaaa agcgtttcgt    120
atcaccggca acatttgggt tattccggat cgttttagcc gtaacagcaa cccgaatctg    180
aataaaccgc cgcgtgttac cagcccgaaa agcggttatt acgatccgaa ctatctgagc    240
accgatagcg ataaagatac cttcctgaaa gaaatcatca actgttcaa acgcatcaac    300 agccgtgaaa ttggcgaaga actgatctat cgcctgagcc ccgatattcc gtttccgggc    360
aacaacaaca ccccgatcaa caccttgat ttcgatgtgg atttcaacag cgttgatgtt    420
aaaacccgcc agggtaacaa ttgggtgaaa accggcagca ttaacccaag cgtgattatt    480
accggtccgc gcgaaaacat tattgatccg gaaaccagca cctttaaact gaccaacaac    540
acctttgcgg cgcaggaagg ttttggcgcg ctgagcatta ttagcattag cccgcgcttt    600
atgctgacct atagcaacgc gaccaacgat gttggtgaag ccgtttcag caaaagcgaa    660 ttttgcatgg acccgatcct gatcctgatg catgaactga accatgcgat gcataacctg    720
tatggcatcg cgattccgaa cgatcagacc attagcagcg tgaccagcaa catcttttac    780
agccagtaca acgtgaaact ggaatatgcg gaaatctatg cgtttggcgg tccgaccatt    840
gatctgattc cgaaaagcgc gcgcaaatac ttcgaagaaa aagcgctgga ttactatcgc    900
agcattgcga acgtctgaa cagcattacc accgcgaatc cgagcagctt caacaaatat    960
atcggcgaat ataaacagaa actgatccgc aaatatcgct ttgtggtgga aagcagcggc   1020
gaagttaccg ttaaccgcaa taaattcgtg gaactgtaca cgaactgac ccagatcttc    1080 accgaattta ctatgcgaa aatctataac gtgcagaacc gtaaaatcta cctgagcaac   1140
gtgtataccc cggtgaccgc gaatattctg gatgataacg tgtacgatat ccagaacggc   1200
```

```
tttaacatcc cgaaaagcaa cctgaacgtt ctgtttatgg gccagaacct gagccgtaat    1260
ccggcgctgc gtaaagtgaa cccggaaaac atgctgtacc tgttcaccaa attttgcgtc    1320
gacgcgattg atggtcgtag cctgtacaac aaaaccctgc agtgtcgtga actgctggtg    1380
aaaaacaccg atctgccgtt tattggcgat atcagcgatg tgaaaaccga tatcttcctg    1440
cgcaaagata tcaacgaaga aaccgaagtg atctactacc cggataacgt gagcgttgat    1500
caggtgatcc tgagcaaaaa caccagcgaa catggtcagc tggatctgct gtatccgagc    1560
attgatagcg aaagcgaaat tctgccgggc gaaaaccagg tgttttacga taaccgtacc    1620
cagaacgtgg attacctgaa cagctattac tacctggaaa gccagaaact gagcgataac    1680
gtggaagatt ttacctttac ccgcagcatt gaagaagcgc tggataacag cgcgaaagtt    1740
tacacctatt ttccgaccct ggcgaacaaa gttaatgcgg gtgttcaggg cggtctgttt    1800
ctgatgtggg cgaacgatgt ggtggaagat ttcaccacca acatcctgcg taaagatacc    1860
ctggataaaa tcagcgatgt tagcgcgatt attccgtata ttggtccggc gctgaacatt    1920
agcaatagcg tgcgtcgtgg caattttacc gaagcgtttg cggttaccgg tgtgaccatt    1980
ctgctggaag cgtttccgga atttaccatt ccggcgctgg gtgcgtttgt gatctatagc    2040
aaagtgcagg aacgcaacga aatcatcaaa accatcgata actgcctgga acagcgtatt    2100
aaacgctgga agatagcta tgaatggatg atgggcacct ggctgagccg tattatcacc    2160
cagttcaaca acatcagcta ccagatgtac gatagcctga actatcaggc gggtgcgatt    2220
aaagcgaaaa tcgatctgga atacaaaaaa tacagcggca gcgataaaga aaacatcaaa    2280
agccaggttg aaaacctgaa aaacagcctg gatgtgaaaa ttagcgaagc gatgaataac    2340
atcaacaaat tcatccgcga atgcagcgtg acctacctgt tcaaaaacat gctgccgaaa    2400
gtgatcgatg aactgaacga atttgatcgc aacaccaaag cgaaactgat caacctgatc    2460
gatagccaca acattattct ggtgggcgaa gtggataaac tgaaagcgaa agttaacaac    2520
agcttccaga acaccatccc gtttaacatc ttcagctata ccaacaacag cctgctgaaa    2580
gatatcatca acgaatactt caatctagac taataagctt                          2620

<210> SEQ ID NO 3
<211> LENGTH: 249
<212> TYPE: DNA
<213> ORGANISM: Unknown
<220> FEATURE:
<223> OTHER INFORMATION: DNA sequence of EGF linker

<400> SEQUENCE: 3
ggatccgtcg acctgcaggg tctagaaggc ggtggcggta gcggcggtgg cggtagcggc      60
ggtggcggta gcgcactaga caactctgac tctgaatgcc cgctgtctca cgacggttac     120
tgcctgcacg acggtgtttg catgtacatc gaagctctgg acaaatacgc ttgcaactgc     180
gttgttggtt acatcggtga acgttgccag taccgtgacc tgaaatggtg ggaactgcgt     240
tgaaagctt                                                             249

<210> SEQ ID NO 4
<211> LENGTH: 2838
<212> TYPE: DNA
<213> ORGANISM: Unknown
<220> FEATURE:
<223> OTHER INFORMATION: DNA sequence of EGF-C fusion

<400> SEQUENCE: 4
ggatccgaat tcatgccgat caccatcaac aacttcaact acagcgatcc ggtggataac       60
```

-continued

```
aaaaacatcc tgtacctgga tacccatctg aatccctgg cgaacgaacc ggaaaaagcg      120
tttcgtatca ccggcaacat ttgggttatt ccgatcgtt ttagccgtaa cagcaacccg      180
aatctgaata aaccgccgcg tgttaccagc ccgaaaagcg gttattacga tccgaactat      240
ctgagcaccg atagcgataa agataccttc ctgaaagaaa tcatcaaact gttcaaacgc      300
atcaacagcc gtgaaattgg cgaagaactg atctatcgcc tgagcaccga tattccgttt      360
ccgggcaaca caacacccc gatcaacacc tttgatttcg atgtggattt caacagcgtt      420
gatgttaaaa cccgccaggg taacaattgg gtgaaaaccg gcagcattaa cccgagcgtg      480
attattaccg gtccgcgcga aaacattatt gatccggaaa ccagcaccttt aaactgacc      540 aacaacacct tgcggcgca ggaaggtttt ggcgcgctga gcattattag cattagcccg      600
cgctttatgc tgacctatag caacgcgacc aacgatgttg tgaaggccg tttcagcaaa      660 agcgaatttt gcatggaccc gatcctgatc ctgatgcatg aactgaacca tgcgatgcat      720
aacctgtatg gcatcgcgat tccgaacgat cagaccatta gcagcgtgac cagcaacatc      780
ttttacagcc agtacaacgt gaaactggaa tatgcggaaa tctatgcgtt tggcggtccg      840
accattgatc tgattccgaa aagcgcgcgc aaatacttcg aagaaaaagc gctggattac      900
tatcgcagca ttgcgaaacg tctgaacagc attaccaccg cgaatccgag cagcttcaac      960
aaatatatcg gcgaatataa acagaaactg atccgcaaat atcgctttgt ggtgaaaagc     1020
agcggcgaag ttaccgttaa ccgcaataaa ttcgtggaac tgtacaacga actgacccag     1080
atcttcaccg aatttaacta tgcgaaaatc tataacgtgc agaaccgtaa aatctacctg     1140
agcaacgtgt ataccccggt gaccgcgaat attctggatg ataacgtgta cgatatccag     1200
aacggcttta acatcccgaa aagcaacctg aacgttctgt ttatgggcca gaacctgagc     1260
cgtaatccgg cgctgcgtaa agtgaacccg gaaaacatgc tgtacctgtt caccaaattt     1320
tgcgtcgacg cgattgatgg tcgtagcctg tacaacaaaa ccctgcagtg tcgtgaactg     1380
ctggtgaaaa acaccgatct gccgtttatt ggcgatatca gcgatgtgaa aaccgatatc     1440
ttcctgcgca aagatatcaa cgaagaaacc gaagtgatct actacccgga taacgtgagc     1500
gttgatcagg tgatcctgag caaaaacacc agcgaacatg gtcagctgga tctgctgtat     1560
ccgagcattg atagcgaaag cgaaattctg ccgggcgaaa accaggtgtt ttacgataac     1620
cgtacccaga cgtggatta cctgaacagc tattactacc tggaaagcca gaaactgagc     1680
gataacgtgg aagattttac ctttacccgc agcattgaag aagcgctgga taacagcgcg     1740
aaagtttaca cctatttcc gaccctggcg aacaaagtta tgcgggtgt tcagggcggt     1800 ctgtttctga tgtgggcgaa cgatgtggtg aagatttca ccaccaacat cctgcgtaaa     1860
gataccctgg ataaaatcag cgatgttagc gcgattattc cgtatattgg tccggcgctg     1920
aacattagca atagcgtgcg tcgtggcaat tttaccgaag cgtttgcggt taccggtgtg     1980
accattctgc tggaagcgtt tccggaattt accattccgg cgctgggtgc gtttgtgatc     2040
tatagcaaag tgcaggaacg caacgaaatc atcaaaacca tcgataactg cctggaacag     2100
cgtattaaac gctggaaaga tagctatgaa tggatgatgg gcacctggct gagccgtatt     2160
atcacccagt tcaacaacat cagctaccag atgtacgata gcctgaacta tcaggcgggt     2220
gcgattaaag cgaaaatcga tctggaatac aaaaaataca gcggcagcga taagaaaaac     2280
atcaaaagcc aggttgaaaa cctgaaaaac agcctggatg tgaaaattag cgaagcgatg     2340
aataacatca acaaattcat ccgcgaatgc agcgtgacct acctgttcaa aaacatgctg     2400
```

-continued

```
ccgaaagtga tcgatgaact gaacgaattt gatcgcaaca ccaaagcgaa actgatcaac    2460
ctgatcgata gccacaacat tattctggtg ggcgaagtgg ataaactgaa agcgaaagtt    2520
aacaacagct tccagaacac catcccgttt aacatcttca gctataccaa caacagcctg    2580
ctgaaagata tcatcaacga atacttcaat ctagaaggtg cggtgggtc cggtggcggt     2640 ggctcaggcg ggggcggtag cgcactagac aactctgact ctgaatgccc gctgtctcac    2700
gacggttact gcctgcacga cggtgtttgc atgtacatcg aagctctgga caaatacgct    2760
tgcaactgcg ttgttggtta catcggtgaa cgttgccagt accgtgacct gaaatggtgg    2820
gaactgcgtt gaaagctt                                                  2838
```

<210> SEQ ID NO 5
<211> LENGTH: 945
<212> TYPE: PRT
<213> ORGANISM: Unknown
<220> FEATURE:
<223> OTHER INFORMATION: Protein sequence of the EGF-C fusion

<400> SEQUENCE: 5

```
Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
        195                 200                 205

Ala Thr Asn Asp Val Gly Glu Gly Arg Phe Ser Lys Ser Glu Phe Cys
    210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255

Thr Ser Asn Ile Phe Tyr Ser Gln Tyr Asn Val Lys Leu Glu Tyr Ala
            260                 265                 270

Glu Ile Tyr Ala Phe Gly Gly Pro Thr Ile Asp Leu Ile Pro Lys Ser
        275                 280                 285
```

```
Ala Arg Lys Tyr Phe Glu Glu Lys Ala Leu Asp Tyr Tyr Arg Ser Ile
290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                325                 330                 335

Val Val Glu Ser Ser Gly Glu Val Thr Val Asn Arg Asn Lys Phe Val
                340                 345                 350

Glu Leu Tyr Asn Glu Leu Thr Gln Ile Phe Thr Glu Phe Asn Tyr Ala
            355                 360                 365

Lys Ile Tyr Asn Val Gln Asn Arg Lys Ile Tyr Leu Ser Asn Val Tyr
370                 375                 380

Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
                405                 410                 415

Gln Asn Leu Ser Arg Asn Pro Ala Leu Arg Lys Val Asn Pro Glu Asn
                420                 425                 430

Met Leu Tyr Leu Phe Thr Lys Phe Cys Val Asp Ala Ile Asp Gly Arg
            435                 440                 445

Ser Leu Tyr Asn Lys Thr Leu Gln Cys Arg Glu Leu Leu Val Lys Asn
450                 455                 460

Thr Asp Leu Pro Phe Ile Gly Asp Ile Ser Asp Val Lys Thr Asp Ile
465                 470                 475                 480

Phe Leu Arg Lys Asp Ile Asn Glu Glu Thr Glu Val Ile Tyr Tyr Pro
                485                 490                 495

Asp Asn Val Ser Val Asp Gln Val Ile Leu Ser Lys Asn Thr Ser Glu
                500                 505                 510

His Gly Gln Leu Asp Leu Leu Tyr Pro Ser Ile Asp Ser Glu Ser Glu
            515                 520                 525

Ile Leu Pro Gly Glu Asn Gln Val Phe Tyr Asp Asn Arg Thr Gln Asn
530                 535                 540

Val Asp Tyr Leu Asn Ser Tyr Tyr Leu Glu Ser Gln Lys Leu Ser
545                 550                 555                 560

Asp Asn Val Glu Asp Phe Thr Phe Thr Arg Ser Ile Glu Glu Ala Leu
                565                 570                 575

Asp Asn Ser Ala Lys Val Tyr Thr Tyr Phe Pro Thr Leu Ala Asn Lys
            580                 585                 590

Val Asn Ala Gly Val Gln Gly Gly Leu Phe Leu Met Trp Ala Asn Asp
            595                 600                 605

Val Val Glu Asp Phe Thr Thr Asn Ile Leu Arg Lys Asp Thr Leu Asp
            610                 615                 620

Lys Ile Ser Asp Val Ser Ala Ile Ile Pro Tyr Ile Gly Pro Ala Leu
625                 630                 635                 640

Asn Ile Ser Asn Ser Val Arg Arg Gly Asn Phe Thr Glu Ala Phe Ala
                645                 650                 655

Val Thr Gly Val Thr Ile Leu Leu Glu Ala Phe Pro Glu Phe Thr Ile
                660                 665                 670

Pro Ala Leu Gly Ala Phe Val Ile Tyr Ser Lys Val Gln Glu Arg Asn
            675                 680                 685

Glu Ile Ile Lys Thr Ile Asp Asn Cys Leu Glu Gln Arg Ile Lys Arg
690                 695                 700
```

```
Trp Lys Asp Ser Tyr Glu Trp Met Met Gly Thr Trp Leu Ser Arg Ile
705                 710                 715                 720
Ile Thr Gln Phe Asn Asn Ile Ser Tyr Gln Met Tyr Asp Ser Leu Asn
            725                 730                 735
Tyr Gln Ala Gly Ala Ile Lys Ala Lys Ile Asp Leu Glu Tyr Lys Lys
        740                 745                 750
Tyr Ser Gly Ser Asp Lys Glu Asn Ile Lys Ser Gln Val Glu Asn Leu
    755                 760                 765
Lys Asn Ser Leu Asp Val Lys Ile Ser Glu Ala Met Asn Asn Ile Asn
770                 775                 780
Lys Phe Ile Arg Glu Cys Ser Val Thr Tyr Leu Phe Lys Asn Met Leu
785                 790                 795                 800
Pro Lys Val Ile Asp Glu Leu Asn Glu Phe Asp Arg Asn Thr Lys Ala
            805                 810                 815
Lys Leu Ile Asn Leu Ile Asp Ser His Asn Ile Ile Leu Val Gly Glu
        820                 825                 830
Val Asp Lys Leu Lys Ala Lys Val Asn Asn Ser Phe Gln Asn Thr Ile
    835                 840                 845
Pro Phe Asn Ile Phe Ser Tyr Thr Asn Asn Ser Leu Leu Lys Asp Ile
850                 855                 860
Ile Asn Glu Tyr Phe Asn Leu Glu Gly Gly Gly Ser Gly Gly Gly
865                 870                 875                 880
Gly Ser Gly Gly Gly Ser Ala Leu Asp Asn Ser Asp Ser Glu Cys
            885                 890                 895
Pro Leu Ser His Asp Gly Tyr Cys Leu His Asp Gly Val Cys Met Tyr
        900                 905                 910
Ile Glu Ala Leu Asp Lys Tyr Ala Cys Asn Cys Val Val Gly Tyr Ile
    915                 920                 925
Gly Glu Arg Cys Gln Tyr Arg Asp Leu Lys Trp Trp Glu Leu Arg Lys
930                 935                 940
Leu
945

<210> SEQ ID NO 6
<211> LENGTH: 2850
<212> TYPE: DNA
<213> ORGANISM: Unknown
<220> FEATURE:
<223> OTHER INFORMATION: DNA sequence of the EGF-B fusion

<400> SEQUENCE: 6
ggatccatgc cggttaccat caacaacttc aactacaacg acccgatcga caacaacaac     60
atcattatga tggaaccgcc gttcgcacgt ggtaccggac gttactacaa ggcttttaag    120
atcaccgacc gtatctggat catcccggaa cgttacacct tcggttacaa acctgaggac    180
ttcaacaaga gtagcgggat tttcaatcgt gacgtctgcg agtactatga tccagattat    240
ctgaatacca acgataagaa gaacatattc cttcagacta tgattaaact cttcaaccgt    300
atcaaaagca aaccgctcgg tgaaaaactc ctcgaaatga ttatcaacgg tatcccgtac    360
ctcggtgacc gtcgtgtccc gcttgaagag ttcaacacca catcgcaag cgtcaccgtc    420 aacaaactca tcagcaaccc aggtgaagtc gaacgtaaaa aaggtatctt cgcaaacctc    480
atcatcttcg gtccgggtcc ggtcctcaac gaaaacgaaa ccatcgacat cggtatccag    540
aaccacttcg caagccgtga aggtttcggt ggtatcatgc agatgaaatt ctgcccggaa    600
tacgtcagtg tcttcaacaa cgtccaggaa aacaaaggtg caagcatctt caaccgtcgt    660
```

```
ggttacttca gcgacccggc actcatcctc atgcatgaac tcatccacgt cctccacggt    720
ctctacggta tcaaagttga cgacctcccg atcgtcccga acgagaagaa attcttcatg    780
cagagcaccg acgcaatcca ggctgaggaa ctctacacct tcggtggcca agacccaagt    840
atcataaccc cgtccaccga caaaagcatc tacgacaaag tcctccagaa cttcaggggt    900
atcgtggaca gactcaacaa agtcctcgtc tgcatcagcg acccgaacat caatatcaac    960
atatacaaga acaagttcaa agacaagtac aaattcgtcg aggacagcga aggcaaatac   1020
agcatcgacg tagaaagttt cgacaagctc tacaaaagcc tcatgttcgg tttcaccgaa   1080
accaacatcg ccgagaacta caagatcaag acaagggcaa gttacttcag cgacagcctc   1140
ccgcctgtca aaatcaagaa cctcttagac aacgagattt acacaattga gagggcttc    1200 aacatcagtg acaagacat ggagaaggaa tacagaggtc agaacaaggc tatcaacaaa   1260
caggcatacg aggagatcag caaagaacac ctcgcagtct acaagatcca gatgtgcgtc   1320
gacgaagaaa agctgtacga cgacgacgac aaagaccgtt ggggttcttc gctgcagtgc   1380
atcgacgttg acaacgaaga cctgttcttc atcgctgaca aaaacagctt cagtgacgac   1440
ctgagcaaaa acgaacgtat cgaatacaac acccagagca actacatcga aaacgacttc   1500
ccgatcaacg aactgatcct ggacaccgac ctgataagta aaatcgaact gccgagcgaa   1560
aacaccgaaa gtctgaccga cttcaacgtt gacgttccgg tttacgaaaa acagccggct   1620
atcaagaaaa tcttcaccga cgaaaacacc atcttccagt acctgtacag ccagaccttc   1680
ccgctggaca tccgtgacat cagtctgacc agcagtttcg acgacgctct gctgttcagc   1740
aacaaagttt acagtttctt cagcatggac tacatcaaaa ccgctaacaa agttgttgaa   1800
gcagggctgt tcgctggttg ggttaaacag atcgttaacg acttcgttat cgaagctaac   1860
aaaagcaaca ctatggacaa aatcgctgac atcagtctga tcgttccgta catcggtctg   1920
gctctgaacg ttggtaacga aaccgctaaa ggtaactttg aaaacgcttt cgagatcgct   1980
ggtgcaagca tcctgctgga gttcatcccg gaactgctga tcccggttgt tggtgctttc   2040
ctgctggaaa gttacatcga caacaaaaac aagatcatca aaaccatcga caacgctctg   2100
accaaacgta acgaaaaatg gagtgatatg tacggtctga tcgttgctca gtggctgagc   2160
accgtcaaca cccagttcta caccatcaaa gaaggtatgt acaaagctct gaactaccag   2220
gctcaggctc tggaagagat catcaaatac cgttacaaca tctacagtga aaggaaaag   2280 agtaacatca acatcgactt caacgacatc aacagcaaac tgaacgaagg tatcaaccag   2340
gctatcgaca acatcaacaa cttcatcaac ggttgcagtg ttagctacct gatgaagaag   2400
atgatcccgc tggctgttga aaaactgctg gacttcgaca acaccctgaa aaagaacctg   2460
ctgaactaca tcgacgaaaa caagctgtac ctgatcggta gtgctgaata cgaaaaaagt   2520
aaagtgaaca aatacctgaa gaccatcatg ccgttcgacc tgagtatcta caccaacgac   2580
accatcctga tcgaaatgtt caacaaatac aactctctag atctagaagg tggcggtggg   2640
tccggtggcg gtggctcagg cggggggcggt agcgcactag acaactctga ctctgaatgc   2700
ccgctgtctc acgacggtta ctgcctgcac gacggtgttt gcatgtacat cgaagctctg   2760
gacaaatacg cttgcaactg cgttgttggt tacatcggtg aacgttgcca gtaccgtgac   2820
ctgaaatggt gggaactgcg ttgaaagctt                                    2850
```

<210> SEQ ID NO 7
<211> LENGTH: 949
<212> TYPE: PRT

```
<213> ORGANISM: Unknown
<220> FEATURE:
<223> OTHER INFORMATION: Protein sequence of the EGF-B fusion

<400> SEQUENCE: 7

Gly Ser Met Pro Val Thr Ile Asn Asn Phe Asn Tyr Asn Asp Pro Ile
1               5                   10                  15

Asp Asn Asn Asn Ile Ile Met Met Glu Pro Pro Phe Ala Arg Gly Thr
            20                  25                  30

Gly Arg Tyr Tyr Lys Ala Phe Lys Ile Thr Asp Arg Ile Trp Ile Ile
        35                  40                  45

Pro Glu Arg Tyr Thr Phe Gly Tyr Lys Pro Glu Asp Phe Asn Lys Ser
    50                  55                  60

Ser Gly Ile Phe Asn Arg Asp Val Cys Glu Tyr Tyr Asp Pro Asp Tyr
65                  70                  75                  80

Leu Asn Thr Asn Asp Lys Lys Asn Ile Phe Leu Gln Thr Met Ile Lys
                85                  90                  95

Leu Phe Asn Arg Ile Lys Ser Lys Pro Leu Gly Glu Lys Leu Leu Glu
            100                 105                 110

Met Ile Ile Asn Gly Ile Pro Tyr Leu Gly Asp Arg Arg Val Pro Leu
        115                 120                 125

Glu Glu Phe Asn Thr Asn Ile Ala Ser Val Thr Val Asn Lys Leu Ile
    130                 135                 140

Ser Asn Pro Gly Glu Val Glu Arg Lys Lys Gly Ile Phe Ala Asn Leu
145                 150                 155                 160

Ile Ile Phe Gly Pro Gly Pro Val Leu Asn Glu Asn Glu Thr Ile Asp
                165                 170                 175

Ile Gly Ile Gln Asn His Phe Ala Ser Arg Glu Gly Phe Gly Gly Ile
            180                 185                 190

Met Gln Met Lys Phe Cys Pro Glu Tyr Val Ser Val Phe Asn Asn Val
        195                 200                 205

Gln Glu Asn Lys Gly Ala Ser Ile Phe Asn Arg Arg Gly Tyr Phe Ser
    210                 215                 220

Asp Pro Ala Leu Ile Leu Met His Glu Leu Ile His Val Leu His Gly
225                 230                 235                 240

Leu Tyr Gly Ile Lys Val Asp Asp Leu Pro Ile Val Pro Asn Glu Lys
                245                 250                 255

Lys Phe Phe Met Gln Ser Thr Asp Ala Ile Gln Ala Glu Glu Leu Tyr
            260                 265                 270

Thr Phe Gly Gly Gln Asp Pro Ser Ile Ile Thr Pro Ser Thr Asp Lys
        275                 280                 285

Ser Ile Tyr Asp Lys Val Leu Gln Asn Phe Arg Gly Ile Val Asp Arg
    290                 295                 300

Leu Asn Lys Val Leu Val Cys Ile Ser Asp Pro Asn Ile Asn Ile Asn
305                 310                 315                 320

Ile Tyr Lys Asn Lys Phe Lys Asp Lys Tyr Lys Phe Val Glu Asp Ser
                325                 330                 335

Glu Gly Lys Tyr Ser Ile Asp Val Glu Ser Phe Asp Lys Leu Tyr Lys
            340                 345                 350

Ser Leu Met Phe Gly Phe Thr Glu Thr Asn Ile Ala Glu Asn Tyr Lys
        355                 360                 365

Ile Lys Thr Arg Ala Ser Tyr Phe Ser Asp Ser Leu Pro Pro Val Lys
    370                 375                 380

Ile Lys Asn Leu Leu Asp Asn Glu Ile Tyr Thr Ile Glu Glu Gly Phe
```

-continued

```
                385                 390                 395                 400
        Asn Ile Ser Asp Lys Asp Met Glu Lys Glu Tyr Arg Gly Gln Asn Lys
                            405                 410                 415
        Ala Ile Asn Lys Gln Ala Tyr Glu Glu Ile Ser Lys Glu His Leu Ala
                        420                 425                 430
        Val Tyr Lys Ile Gln Met Cys Val Asp Glu Glu Lys Leu Tyr Asp Asp
                    435                 440                 445
        Asp Asp Lys Asp Arg Trp Gly Ser Ser Leu Gln Cys Ile Asp Val Asp
                450                 455                 460
        Asn Glu Asp Leu Phe Phe Ile Ala Asp Lys Asn Ser Phe Ser Asp Asp
        465                 470                 475                 480
        Leu Ser Lys Asn Glu Arg Ile Glu Tyr Asn Thr Gln Ser Asn Tyr Ile
                            485                 490                 495
        Glu Asn Asp Phe Pro Ile Asn Glu Leu Ile Leu Asp Thr Asp Leu Ile
                        500                 505                 510
        Ser Lys Ile Glu Leu Pro Ser Glu Asn Thr Glu Ser Leu Thr Asp Phe
                    515                 520                 525
        Asn Val Asp Val Pro Val Tyr Glu Lys Gln Pro Ala Ile Lys Lys Ile
                530                 535                 540
        Phe Thr Asp Glu Asn Thr Ile Phe Gln Tyr Leu Tyr Ser Gln Thr Phe
        545                 550                 555                 560
        Pro Leu Asp Ile Arg Asp Ile Ser Leu Thr Ser Ser Phe Asp Asp Ala
                            565                 570                 575
        Leu Leu Phe Ser Asn Lys Val Tyr Ser Phe Phe Ser Met Asp Tyr Ile
                        580                 585                 590
        Lys Thr Ala Asn Lys Val Val Glu Ala Gly Leu Phe Ala Gly Trp Val
                    595                 600                 605
        Lys Gln Ile Val Asn Asp Phe Val Ile Glu Ala Asn Lys Ser Asn Thr
                610                 615                 620
        Met Asp Lys Ile Ala Asp Ile Ser Leu Ile Val Pro Tyr Ile Gly Leu
        625                 630                 635                 640
        Ala Leu Asn Val Gly Asn Glu Thr Ala Lys Gly Asn Phe Glu Asn Ala
                            645                 650                 655
        Phe Glu Ile Ala Gly Ala Ser Ile Leu Leu Glu Phe Ile Pro Glu Leu
                        660                 665                 670
        Leu Ile Pro Val Val Gly Ala Phe Leu Leu Glu Ser Tyr Ile Asp Asn
                    675                 680                 685
        Lys Asn Lys Ile Ile Lys Thr Ile Asp Asn Ala Leu Thr Lys Arg Asn
                690                 695                 700
        Glu Lys Trp Ser Asp Met Tyr Gly Leu Ile Val Ala Gln Trp Leu Ser
        705                 710                 715                 720
        Thr Val Asn Thr Gln Phe Tyr Thr Ile Lys Glu Gly Met Tyr Lys Ala
                            725                 730                 735
        Leu Asn Tyr Gln Ala Gln Ala Leu Glu Glu Ile Ile Lys Tyr Arg Tyr
                        740                 745                 750
        Asn Ile Tyr Ser Glu Lys Glu Lys Ser Asn Ile Asn Ile Asp Phe Asn
                    755                 760                 765
        Asp Ile Asn Ser Lys Leu Asn Glu Gly Ile Asn Gln Ala Ile Asp Asn
                770                 775                 780
        Ile Asn Asn Phe Ile Asn Gly Cys Ser Val Ser Tyr Leu Met Lys Lys
        785                 790                 795                 800
        Met Ile Pro Leu Ala Val Glu Lys Leu Leu Asp Phe Asp Asn Thr Leu
                            805                 810                 815
```

```
Lys Lys Asn Leu Leu Asn Tyr Ile Asp Glu Asn Lys Leu Tyr Leu Ile
            820                 825                 830
Gly Ser Ala Glu Tyr Glu Lys Ser Lys Val Asn Lys Tyr Leu Lys Thr
            835                 840                 845
Ile Met Pro Phe Asp Leu Ser Ile Tyr Thr Asn Asp Thr Ile Leu Ile
850                 855                 860
Glu Met Phe Asn Lys Tyr Asn Ser Leu Asp Leu Glu Gly Gly Gly Gly
865                 870                 875                 880
Ser Gly Gly Gly Gly Ser Gly Gly Gly Gly Ser Ala Leu Asp Asn Ser
                885                 890                 895
Asp Ser Glu Cys Pro Leu Ser His Asp Gly Tyr Cys Leu His Asp Gly
            900                 905                 910
Val Cys Met Tyr Ile Glu Ala Leu Asp Lys Tyr Ala Cys Asn Cys Val
            915                 920                 925
Val Gly Tyr Ile Gly Glu Arg Cys Gln Tyr Arg Asp Leu Lys Trp Trp
        930                 935                 940
Glu Leu Arg Lys Leu
945

<210> SEQ ID NO 8
<211> LENGTH: 120
<212> TYPE: DNA
<213> ORGANISM: Unknown
<220> FEATURE:
<223> OTHER INFORMATION: DNA sequence of the RGD linker

<400> SEQUENCE: 8
ggatccgtcg acctgcaggg tctagaaggc ggtggcggta gcggcggtgg cggtagcggc     60
ggtggcggta gcgcactagt gggtggtcgt ggtgacatgt tcggtgcttg ataaaagctt    120

<210> SEQ ID NO 9
<211> LENGTH: 2709
<212> TYPE: DNA
<213> ORGANISM: Unknown
<220> FEATURE:
<223> OTHER INFORMATION: DNA sequence of the RGD-C fusion

<400> SEQUENCE: 9
ggatccgaat tcatgccgat caccatcaac aacttcaact acagcgatcc ggtggataac     60
aaaaacatcc tgtacctgga tacccatctg aataccctgg cgaacgaacc ggaaaaagcg    120
tttcgtatca ccggcaacat tgggttatt ccggatcgtt ttagccgtaa cagcaacccg    180
aatctgaata accgccgcg tgttaccagc ccgaaaagcg gttattacga tccgaactat    240
ctgagcaccg atagcgataa agataccttc tgaaagaaa tcatcaaact gttcaaacgc    300
atcaacagcc gtgaaattgg cgaagaactg atctatcgcc tgagcaccga tattccgttt    360
ccgggcaaca caacacccc gatcaacacc tttgatttcg atgtggattt caacagcgtt    420
gatgttaaaa cccgccaggg taacaattgg gtgaaaaccg gcagcattaa cccgagcgtg    480
attattaccg gtccgcgcga aaacattatt gatccggaaa ccagcacctt taaactgacc    540
aacaacacct tgcggcgca ggaaggtttt ggcgcgctga gcattattag cattagcccg    600
cgctttatgc tgacctatag caacgcgacc aacgatgttg gtgaaggccg tttcagcaaa    660
agcgaatttt gcatggaccc gatcctgatc ctgatgcatg aactgaacca tgcgatgcat    720
aacctgtatg gcatcgcgat tccgaacgat cagaccatta gcagcgtgac cagcaacatc    780
ttttacagcc agtacaacgt gaaactggaa tatgcggaaa tctatgcgtt tggcggtccg    840
```

```
accattgatc tgattccgaa aagcgcgcgc aaatacttcg aagaaaaagc gctggattac    900
tatcgcagca ttgcgaaacg tctgaacagc attaccaccg cgaatccgag cagcttcaac    960
aaatatatcg gcgaatataa acagaaactg atccgcaaat atcgctttgt ggtggaaagc   1020
agcggcgaag ttaccgttaa ccgcaataaa ttcgtggaac tgtacaacga actgacccag   1080
atcttcaccg aatttaacta tgcgaaaatc tataacgtgc agaaccgtaa aatctacctg   1140
agcaacgtgt atacccccggt gaccgcgaat attctggatg ataacgtgta cgatatccag   1200
aacggcttta acatcccgaa aagcaacctg aacgttctgt ttatgggcca aacctgagc    1260 cgtaatccgg cgctgcgtaa agtgaacccg gaaaacatgc tgtacctgtt caccaaattt   1320
tgcgtcgacg cgattgatgg tcgtagcctg tacaacaaaa ccctgcagtg tcgtgaactg   1380
ctggtgaaaa acaccgatct gccgtttatt ggcgatatca gcgatgtgaa aaccgatatc   1440
ttcctgcgca aagatatcaa cgaagaaacc gaagtgatct actacccgga taacgtgagc   1500
gttgatcagg tgatcctgag caaaaacacc agcgaacatg gtcagctgga tctgctgtat   1560
ccgagcattg atagcgaaag cgaaattctg ccgggcgaaa accaggtgtt ttacgataac   1620
cgtacccaga acgtggatta cctgaacagc tattactacc tggaaagcca gaaactgagc   1680
gataacgtgg aagattttac ctttacccgc agcattgaag aagcgctgga taacagcgcg   1740
aaagtttaca cctatttccc gaccctggcg aacaaagtta atgcgggtgt tcagggcggt   1800
ctgtttctga tgtgggcgaa cgatgtggtg aagatttca ccaccaacat cctgcgtaaa    1860
gatacctggg ataaaatcag cgatgttagc gcgattattc cgtatattgg tccggcgctg   1920
aacattagca atagcgtgcg tcgtggcaat ttaccgaag cgtttgcggt taccggtgtg    1980
accattctgc tggaagcgtt tccggaattt accattccgg cgctgggtgc gtttgtgatc   2040
tatagcaaag tgcaggaacg caacgaaatc atcaaaacca tcgataactg cctggaacag   2100
cgtattaaac gctggaaaga tagctatgaa tggatgatgg gcacctggct gagccgtatt   2160
atcacccagt tcaacaacat cagctaccag atgtacgata gcctgaacta tcaggcgggt   2220
gcgattaaag cgaaaatcga tctggaatac aaaaaatata gcggcagcga taaagaaaac   2280
atcaaaagcc aggttgaaaa cctgaaaaac agcctggatg tgaaaattag cgaagcgatg   2340
aataacatca caaattcat ccgcgaatgc agcgtgacct acctgttcaa aaacatgctg    2400
ccgaaagtga tcgatgaact gaacgaattt gatcgcaaca ccaaagcgaa actgatcaac   2460
ctgatcgata gccacaacat tattctggtg ggcgaagtgg ataaactgaa agcgaaagtt   2520
aacaacagct tccagaacac catcccgttt aacatcttca gctataccaa caacagcctg   2580
ctgaaagata tcatcaacga atacttcaat ctagaaggcg gtggcggtag cggcggtggc   2640
ggtagcggcg gtggcggtag cgcactagtg ggtggtcgtg gtgacatgtt cggtgcttga   2700
taaaagctt                                                          2709
```

<210> SEQ ID NO 10  
<211> LENGTH: 901  
<212> TYPE: PRT  
<213> ORGANISM: Unknown  
<220> FEATURE:  
<223> OTHER INFORMATION: Protein sequenc eof RGD-C fusion

<400> SEQUENCE: 10

Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr

```
                   20                  25                  30
Leu Ala Asn Glu Pro Glu Lys Ala Phe Arg Ile Thr Gly Asn Ile Trp
            35                  40                  45
Val Ile Pro Asp Arg Phe Ser Arg Asn Ser Asn Pro Asn Leu Asn Lys
        50                  55                  60
Pro Pro Arg Val Thr Ser Pro Lys Ser Gly Tyr Tyr Asp Pro Asn Tyr
65                  70                  75                  80
Leu Ser Thr Asp Ser Asp Lys Asp Thr Phe Leu Lys Glu Ile Ile Lys
                85                  90                  95
Leu Phe Lys Arg Ile Asn Ser Arg Glu Ile Gly Glu Glu Leu Ile Tyr
            100                 105                 110
Arg Leu Ser Thr Asp Ile Pro Phe Pro Gly Asn Asn Asn Thr Pro Ile
        115                 120                 125
Asn Thr Phe Asp Phe Asp Val Asp Phe Asn Ser Val Asp Val Lys Thr
        130                 135                 140
Arg Gln Gly Asn Asn Trp Val Lys Thr Gly Ser Ile Asn Pro Ser Val
145                 150                 155                 160
Ile Ile Thr Gly Pro Arg Glu Asn Ile Ile Asp Pro Glu Thr Ser Thr
                165                 170                 175
Phe Lys Leu Thr Asn Asn Thr Phe Ala Ala Gln Glu Gly Phe Gly Ala
            180                 185                 190
Leu Ser Ile Ile Ser Ile Ser Pro Arg Phe Met Leu Tyr Ser Asn
        195                 200                 205
Ala Thr Asn Asp Val Gly Glu Gly Arg Phe Ser Lys Ser Glu Phe Cys
        210                 215                 220
Met Asp Pro Ile Leu Ile Leu Met His Glu Leu Asn His Ala Met His
225                 230                 235                 240
Asn Leu Tyr Gly Ile Ala Ile Pro Asn Asp Gln Thr Ile Ser Ser Val
                245                 250                 255
Thr Ser Asn Ile Phe Tyr Ser Gln Tyr Asn Val Lys Leu Glu Tyr Ala
            260                 265                 270
Glu Ile Tyr Ala Phe Gly Gly Pro Thr Ile Asp Leu Ile Pro Lys Ser
        275                 280                 285
Ala Arg Lys Tyr Phe Glu Glu Lys Ala Leu Asp Tyr Tyr Arg Ser Ile
        290                 295                 300
Ala Lys Arg Leu Asn Ser Ile Thr Thr Ala Asn Pro Ser Ser Phe Asn
305                 310                 315                 320
Lys Tyr Ile Gly Glu Tyr Lys Gln Lys Leu Ile Arg Lys Tyr Arg Phe
                325                 330                 335
Val Val Glu Ser Ser Gly Glu Val Thr Val Asn Arg Asn Lys Phe Val
            340                 345                 350
Glu Leu Tyr Asn Glu Leu Thr Gln Ile Phe Thr Glu Phe Asn Tyr Ala
        355                 360                 365
Lys Ile Tyr Asn Val Gln Asn Arg Lys Ile Tyr Leu Ser Asn Val Tyr
        370                 375                 380
Thr Pro Val Thr Ala Asn Ile Leu Asp Asp Asn Val Tyr Asp Ile Gln
385                 390                 395                 400
Asn Gly Phe Asn Ile Pro Lys Ser Asn Leu Asn Val Leu Phe Met Gly
                405                 410                 415
Gln Asn Leu Ser Arg Asn Pro Ala Leu Arg Lys Val Asn Pro Glu Asn
            420                 425                 430
Met Leu Tyr Leu Phe Thr Lys Phe Cys Val Asp Ala Ile Asp Gly Arg
        435                 440                 445
```

```
Ser Leu Tyr Asn Lys Thr Leu Gln Cys Arg Glu Leu Leu Val Lys Asn
    450                 455                 460

Thr Asp Leu Pro Phe Ile Gly Asp Ile Ser Asp Val Lys Thr Asp Ile
465                 470                 475                 480

Phe Leu Arg Lys Asp Ile Asn Glu Glu Thr Glu Val Ile Tyr Tyr Pro
                485                 490                 495

Asp Asn Val Ser Val Asp Gln Val Ile Leu Ser Lys Asn Thr Ser Glu
                500                 505                 510

His Gly Gln Leu Asp Leu Leu Tyr Pro Ser Ile Asp Ser Glu Ser Glu
            515                 520                 525

Ile Leu Pro Gly Glu Asn Gln Val Phe Tyr Asp Asn Arg Thr Gln Asn
    530                 535                 540

Val Asp Tyr Leu Asn Ser Tyr Tyr Leu Glu Ser Gln Lys Leu Ser
545                 550                 555                 560

Asp Asn Val Glu Asp Phe Thr Phe Thr Arg Ser Ile Glu Glu Ala Leu
                565                 570                 575

Asp Asn Ser Ala Lys Val Tyr Thr Tyr Phe Pro Thr Leu Ala Asn Lys
                580                 585                 590

Val Asn Ala Gly Val Gln Gly Gly Leu Phe Leu Met Trp Ala Asn Asp
    595                 600                 605

Val Val Glu Asp Phe Thr Thr Asn Ile Leu Arg Lys Asp Thr Leu Asp
610                 615                 620

Lys Ile Ser Asp Val Ser Ala Ile Ile Pro Tyr Ile Gly Pro Ala Leu
625                 630                 635                 640

Asn Ile Ser Asn Ser Val Arg Arg Gly Asn Phe Thr Glu Ala Phe Ala
                645                 650                 655

Val Thr Gly Val Thr Ile Leu Leu Glu Ala Phe Pro Glu Phe Thr Ile
            660                 665                 670

Pro Ala Leu Gly Ala Phe Val Ile Tyr Ser Lys Val Gln Glu Arg Asn
    675                 680                 685

Glu Ile Ile Lys Thr Ile Asp Asn Cys Leu Glu Gln Arg Ile Lys Arg
    690                 695                 700

Trp Lys Asp Ser Tyr Glu Trp Met Met Gly Thr Trp Leu Ser Arg Ile
705                 710                 715                 720

Ile Thr Gln Phe Asn Asn Ile Ser Tyr Gln Met Tyr Asp Ser Leu Asn
                725                 730                 735

Tyr Gln Ala Gly Ala Ile Lys Ala Lys Ile Asp Leu Glu Tyr Lys Lys
                740                 745                 750

Tyr Ser Gly Ser Asp Lys Glu Asn Ile Lys Ser Gln Val Glu Asn Leu
            755                 760                 765

Lys Asn Ser Leu Asp Val Lys Ile Ser Glu Ala Met Asn Asn Ile Asn
770                 775                 780

Lys Phe Ile Arg Glu Cys Ser Val Thr Tyr Leu Phe Lys Asn Met Leu
785                 790                 795                 800

Pro Lys Val Ile Asp Glu Leu Asn Glu Phe Asp Arg Asn Thr Lys Ala
                805                 810                 815

Lys Leu Ile Asn Leu Ile Asp Ser His Asn Ile Ile Leu Val Gly Glu
            820                 825                 830

Val Asp Lys Leu Lys Ala Lys Val Asn Asn Ser Phe Gln Asn Thr Ile
        835                 840                 845

Pro Phe Asn Ile Phe Ser Tyr Thr Asn Asn Ser Leu Leu Lys Asp Ile
850                 855                 860
```

Ile Asn Glu Tyr Phe Asn Leu Glu Gly Gly Gly Gly Ser Gly Gly Gly
865                 870                 875                 880

Gly Ser Gly Gly Gly Ser Ala Leu Val Gly Gly Arg Gly Asp Met
            885                 890                 895

Phe Gly Ala Lys Leu
            900

<210> SEQ ID NO 11
<211> LENGTH: 126
<212> TYPE: DNA
<213> ORGANISM: Unknown
<220> FEATURE:
<223> OTHER INFORMATION: DNA sequence of cyclic RGD linker

<400> SEQUENCE: 11

```
ggatccgtcg acctgcaggg tctagaaggc ggtggcggta gcggcggtgg cggtagcggc    60
ggtggcggta gcgcactagt gggtggttgc cgtggtgaca tgttcggttg cgcttgataa   120
aagctt                                                             126
```

<210> SEQ ID NO 12
<211> LENGTH: 2715
<212> TYPE: DNA
<213> ORGANISM: Unknown
<220> FEATURE:
<223> OTHER INFORMATION: DNA sequence of cyclic RGD-C fusion

<400> SEQUENCE: 12

```
ggatccgaat tcatgccgat caccatcaac aacttcaact acagcgatcc ggtggataac    60
aaaaacatcc tgtacctgga tacccatctg aatccctggc gaacgaaccc ggaaaaagcg   120
tttcgtatca ccggcaacat tgggttatt ccggatcgtt ttagccgtaa cagcaacccg   180
aatctgaata accgccgcg tgttaccagc ccgaaaagcg gttattacga tccgaactat   240
ctgagcaccg atagcgataa agatacctc tgaaagaaa tcatcaaact gttcaaacgc   300
atcaacagcc gtgaaattgg cgaagaactg atctatcgcc tgagcaccga tattccgttt   360
ccgggcaaca caacaccccc gatcaacacc tttgatttcg atgtggattt caacagcgtt   420
gatgttaaaa cccgccaggg taacaattgg gtgaaaccg gcagcattaa cccgagcgtg   480
attattaccg tccgcgcga aaacattatt gatccggaaa ccagcacctt taaactgacc   540
aacaacacct ttgcggcgca ggaaggtttt ggcgcgctga gcattattag cattagcccg   600
cgctttatgc tgacctatag caacgcgacc aacgatgttg gtgaaggccg tttcagcaaa   660
agcgaatttt gcatggaccc gatcctgatc ctgatgcatg aactgaacca tgcgatgcat   720
aacctgtatg gcatcgcgat tccgaacgat cagaccatta gcagcgtgac cagcaacatc   780
ttttacagcc agtacaacgt gaaactgaa tatgcgaaa tctatgcgtt ggcggtccg   840
accattgatc tgattccgaa aagcgcgcgc aaatacttcg aagaaaaagc gctggattac   900
tatcgcagca ttgcgaaacg tctgaacagc attaccaccg cgaatccgag cagcttcaac   960
aaatatatcg gcgaatataa acagaaactg atccgcaaat atcgctttgt ggtggaaagc  1020
agcggcgaag ttaccgttaa ccgcaataaa ttcgtggaac tgtacaacga actgacccag  1080
atcttcaccg aatttaacta tgcgaaaatc tataacgtgc agaaccgtaa aatctacctg  1140
agcaacgtgt ataccccggt gaccgcgaat attctggatg ataacgtgta cgatatccag  1200
aacggcttta acatcccgaa aagcaacctg aacgttctgt ttatgggcca gaacctgagc  1260
cgtaatccgg cgctgcgtaa agtgaacccg gaaaacatgc tgtacctgtt caccaaattt  1320
```

```
tgcgtcgacg cgattgatgg tcgtagcctg tacaacaaaa ccctgcagtg tcgtgaactg   1380
ctggtgaaaa acaccgatct gccgtttatt ggcgatatca gcgatgtgaa aaccgatatc   1440
ttcctgcgca agatatcaa cgaagaaacc gaagtgatct actacccgga taacgtgagc   1500
gttgatcagg tgatcctgag caaaaacacc agcgaacatg gtcagctgga tctgctgtat   1560
ccgagcattg atagcgaaag cgaaattctg ccgggcgaaa accaggtgtt ttacgataac   1620
cgtacccaga cgtggatta cctgaacagc tattactacc tggaaagcca gaaactgagc   1680
gataacgtgg aagatttac ctttacccgc agcattgaag aagcgctgga taacagcgcg   1740
aaagtttaca cctatttcc gaccctggcg aacaaagtta atgcgggtgt tcagggcggt   1800
ctgtttctga tgtgggcgaa cgatgtggtg aagatttca ccaccaacat cctgcgtaaa   1860
gataccctgg ataaaatcag cgatgttagc gcgattattc cgtatattgg tccggcgctg   1920
aacattagca atagcgtgcg tcgtggcaat tttaccgaag cgtttgcggt taccggtgtg   1980
accattctgc tggaagcgtt tccggaattt accattccgg cgctgggtgc gtttgtgatc   2040
tatagcaaag tgcaggaacg caacgaaatc atcaaaacca tcgataactg cctggaacag   2100
cgtattaaac gctggaaaga tagctatgaa tggatgatgg cacctggct gagccgtatt   2160 atcacccagt tcaacaacat cagctaccag atgtacgata gcctgaacta tcaggcgggt   2220
gcgattaaag cgaaaatcga tctggaatac aaaaaataca gcggcagcga taagaaaaac   2280
atcaaaagcc aggttgaaaa cctgaaaaac agcctggatg tgaaaattag cgaagcgatg   2340
aataacatca caaattcat ccgcgaatgc agcgtgacct acctgttcaa aaacatgctg   2400
ccgaaagtga tcgatgaact gaacgaattt gatcgcaaca ccaaagcgaa actgatcaac   2460
ctgatcgata gccacaacat tattctggtg ggcgaagtgg ataaactgaa agcgaaagtt   2520
aacaacagct tccagaacac catcccgttt aacatcttca gctataccaa caacagcctg   2580
ctgaaagata tcatcaacga atacttcaat ctagaaggcg gtggcggtag cggcggtggc   2640
ggtagcggcg gtggcggtag cgcactagtg ggtggttgcc gtggtgacat gttcggttgc   2700
gcttgataaa agctt                                                   2715
```

<210> SEQ ID NO 13
<211> LENGTH: 903
<212> TYPE: PRT
<213> ORGANISM: Unknown
<220> FEATURE:
<223> OTHER INFORMATION: Protein sequence of cyclic RGD-C fusion

<400> SEQUENCE: 13

```
Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110
```

```
Arg Leu Ser Thr Asp Ile Pro Phe Pro Gly Asn Asn Thr Pro Ile
            115                 120                 125
Asn Thr Phe Asp Phe Asp Val Asp Phe Asn Ser Val Asp Val Lys Thr
130                 135                 140
Arg Gln Gly Asn Asn Trp Val Lys Thr Gly Ser Ile Asn Pro Ser Val
145                 150                 155                 160
Ile Ile Thr Gly Pro Arg Glu Asn Ile Ile Asp Pro Glu Thr Ser Thr
                165                 170                 175
Phe Lys Leu Thr Asn Asn Thr Phe Ala Ala Gln Glu Gly Phe Gly Ala
            180                 185                 190
Leu Ser Ile Ile Ser Ile Ser Pro Arg Phe Met Leu Thr Tyr Ser Asn
        195                 200                 205
Ala Thr Asn Asp Val Gly Glu Gly Arg Phe Ser Lys Ser Glu Phe Cys
    210                 215                 220
Met Asp Pro Ile Leu Ile Leu Met His Glu Leu Asn His Ala Met His
225                 230                 235                 240
Asn Leu Tyr Gly Ile Ala Ile Pro Asn Asp Gln Thr Ile Ser Ser Val
                245                 250                 255
Thr Ser Asn Ile Phe Tyr Ser Gln Tyr Asn Val Lys Leu Glu Tyr Ala
            260                 265                 270
Glu Ile Tyr Ala Phe Gly Gly Pro Thr Ile Asp Leu Ile Pro Lys Ser
        275                 280                 285
Ala Arg Lys Tyr Phe Glu Glu Lys Ala Leu Asp Tyr Tyr Arg Ser Ile
    290                 295                 300
Ala Lys Arg Leu Asn Ser Ile Thr Thr Ala Asn Pro Ser Ser Phe Asn
305                 310                 315                 320
Lys Tyr Ile Gly Glu Tyr Lys Gln Lys Leu Ile Arg Lys Tyr Arg Phe
                325                 330                 335
Val Val Glu Ser Ser Gly Glu Val Thr Val Asn Arg Asn Lys Phe Val
            340                 345                 350
Glu Leu Tyr Asn Glu Leu Thr Gln Ile Phe Thr Glu Phe Asn Tyr Ala
        355                 360                 365
Lys Ile Tyr Asn Val Gln Asn Arg Lys Ile Tyr Leu Ser Asn Val Tyr
    370                 375                 380
Thr Pro Val Thr Ala Asn Ile Leu Asp Asp Asn Val Tyr Asp Ile Gln
385                 390                 395                 400
Asn Gly Phe Asn Ile Pro Lys Ser Asn Leu Asn Val Leu Phe Met Gly
                405                 410                 415
Gln Asn Leu Ser Arg Asn Pro Ala Leu Arg Lys Val Asn Pro Glu Asn
            420                 425                 430
Met Leu Tyr Leu Phe Thr Lys Phe Cys Val Asp Ala Ile Asp Gly Arg
        435                 440                 445
Ser Leu Tyr Asn Lys Thr Leu Gln Cys Arg Glu Leu Leu Val Lys Asn
    450                 455                 460
Thr Asp Leu Pro Phe Ile Gly Asp Ile Ser Asp Val Lys Thr Asp Ile
465                 470                 475                 480
Phe Leu Arg Lys Asp Ile Asn Glu Glu Thr Glu Val Ile Tyr Tyr Pro
                485                 490                 495
Asp Asn Val Ser Val Asp Gln Val Ile Leu Ser Lys Asn Thr Ser Glu
            500                 505                 510
His Gly Gln Leu Asp Leu Leu Tyr Pro Ser Ile Asp Ser Glu Ser Glu
        515                 520                 525
Ile Leu Pro Gly Glu Asn Gln Val Phe Tyr Asp Asn Arg Thr Gln Asn
```

```
            530                 535                 540
Val Asp Tyr Leu Asn Ser Tyr Tyr Leu Glu Ser Gln Lys Leu Ser
545                 550                 555                 560

Asp Asn Val Glu Asp Phe Thr Phe Thr Arg Ser Ile Glu Glu Ala Leu
                565                 570                 575

Asp Asn Ser Ala Lys Val Tyr Thr Tyr Phe Pro Thr Leu Ala Asn Lys
                580                 585                 590

Val Asn Ala Gly Val Gln Gly Gly Leu Phe Leu Met Trp Ala Asn Asp
                595                 600                 605

Val Val Glu Asp Phe Thr Thr Asn Ile Leu Arg Lys Asp Thr Leu Asp
        610                 615                 620

Lys Ile Ser Asp Val Ser Ala Ile Ile Pro Tyr Ile Gly Pro Ala Leu
625                 630                 635                 640

Asn Ile Ser Asn Ser Val Arg Arg Gly Asn Phe Thr Glu Ala Phe Ala
                645                 650                 655

Val Thr Gly Val Thr Ile Leu Leu Glu Ala Phe Pro Glu Phe Thr Ile
                660                 665                 670

Pro Ala Leu Gly Ala Phe Val Ile Tyr Ser Lys Val Gln Glu Arg Asn
                675                 680                 685

Glu Ile Ile Lys Thr Ile Asp Asn Cys Leu Glu Gln Arg Ile Lys Arg
        690                 695                 700

Trp Lys Asp Ser Tyr Glu Trp Met Met Gly Thr Trp Leu Ser Arg Ile
705                 710                 715                 720

Ile Thr Gln Phe Asn Asn Ile Ser Tyr Gln Met Tyr Asp Ser Leu Asn
                725                 730                 735

Tyr Gln Ala Gly Ala Ile Lys Ala Lys Ile Asp Leu Glu Tyr Lys Lys
                740                 745                 750

Tyr Ser Gly Ser Asp Lys Glu Asn Ile Lys Ser Gln Val Glu Asn Leu
                755                 760                 765

Lys Asn Ser Leu Asp Val Lys Ile Ser Glu Ala Met Asn Asn Ile Asn
                770                 775                 780

Lys Phe Ile Arg Glu Cys Ser Val Thr Tyr Leu Phe Lys Asn Met Leu
785                 790                 795                 800

Pro Lys Val Ile Asp Glu Leu Asn Glu Phe Asp Arg Asn Thr Lys Ala
                805                 810                 815

Lys Leu Ile Asn Leu Ile Asp Ser His Asn Ile Ile Leu Val Gly Glu
                820                 825                 830

Val Asp Lys Leu Lys Ala Lys Val Asn Asn Ser Phe Gln Asn Thr Ile
        835                 840                 845

Pro Phe Asn Ile Phe Ser Tyr Thr Asn Asn Ser Leu Leu Lys Asp Ile
850                 855                 860

Ile Asn Glu Tyr Phe Asn Leu Glu Gly Gly Gly Ser Gly Gly Gly
865                 870                 875                 880

Gly Ser Gly Gly Gly Ser Ala Leu Val Gly Gly Cys Arg Gly Asp
                885                 890                 895

Met Phe Gly Cys Ala Lys Leu
            900

<210> SEQ ID NO 14
<211> LENGTH: 156
<212> TYPE: DNA
<213> ORGANISM: Unknown
<220> FEATURE:
<223> OTHER INFORMATION: DNA sequence of the LC/C-RGD-HN/C LINKER
```

<400> SEQUENCE: 14

```
ggatccacgc acgtcgacgc gattgatggt cgtggtggtc gtggtgacat gttcggtgct     60
gcgctagcgg gcggtggcgg tagcggcggt ggcggtagcg gcggtggcgg tagcgcacta    120
gtgctgcaga cgcacggtct agaatgataa aagctt                              156
```

<210> SEQ ID NO 15
<211> LENGTH: 2733
<212> TYPE: DNA
<213> ORGANISM: Unknown
<220> FEATURE:
<223> OTHER INFORMATION: DNA sequence of the LC/C-RGD-HN/C fusion

<400> SEQUENCE: 15

```
ggatccgaat tcatgccgat caccatcaac aacttcaact acagcgatcc ggtggataac     60
aaaaacatcc tgtacctgga tacccatctg aataccctgg cgaacgaacc ggaaaaagcg    120
tttcgtatca ccggcaacat ttgggttatt ccggatcgtt ttagccgtaa cagcaacccg    180
aatctgaata aaccgccgcg tgttaccagc ccgaaaagcg gttattacga tccgaactat    240
ctgagcaccg atagcgataa agataccttc ctgaaagaaa tcatcaaact gttcaaacgc    300
atcaacagcc gtgaaattgg cgaagaactg atctatcgcc tgagcaccga tattccgttt    360
ccgggcaaca caacacccc gatcaacacc tttgatttcg atgtggattt caacagcgtt    420
gatgttaaaa cccgccaggg taacaattgg gtgaaaaccg gcagcattaa cccgagcgtg    480
attattaccg gtccgcgcga aaacattatt gatccggaaa ccagcacctt aaactgacc    540
aacaacaccct ttgcggcgca ggaaggtttt ggcgcgctga gcattattag cattagcccg    600
cgctttatgc tgacctatag caacgcgacc aacgatgttg gtgaaggccg tttcagcaaa    660
agcgaatttt gcatggaccc gatcctgatc ctgatgcatg aactgaacca tgcgatgcat    720
aacctgtatg gcatcgcgat tccgaacgat cagaccatta gcagcgtgac cagcaacatc    780
ttttacagcc agtacaacgt gaaactggaa tatgcggaaa tctatgcgtt tggcggtccg    840
accattgatc tgattccgaa aagcgcgcgc aaatacttcg aagaaaaagc gctggattac    900
tatcgcagca ttgcgaaacg tctgaacagc attaccaccg cgaatccgag cagcttcaac    960
aaatatatcg gcgaatataa acagaaactg atccgcaaat atcgctttgt ggtggaaagc   1020
agcggcgaag ttaccgttaa ccgcaataaa ttcgtggaac tgtacaacga actgacccag   1080
atcttcaccg aatttaacta tgcgaaaatc tataacgtgc agaaccgtaa atctacctg   1140
agcaacgtgt ataccccggt gaccgcgaat attctggatg ataacgtgta cgatatccag   1200
aacggcttta acatcccgaa aagcaacctg aacgttctgt ttatgggcca gaacctgagc   1260
cgtaatccgg cgctgcgtaa agtgaacccc gaaaacatgc tgtacctgtt caccaaattt   1320
tgcgtcgacg cgattgatgg tcgtggtggt cgtggtgaca tgttcggtgc tgcgctagcg   1380
ggcggtggcg gtagcggcgg tggcggtagc ggcggtggcg gtagcgcact agtgctgcag   1440
tgtcgtgaac tgctggtgaa aaacaccgat ctgccgttta ttggcgatat cagcgatgtg   1500
aaaaccgata tcttcctgcg caaagatatc aacgaagaaa ccgaagtgat ctactacccg   1560
gataacgtga cgttgatca ggtgatcctg agcaaaaca ccagcgaaca tggtcagctg    1620
gatctgctgt atccgagcat tgatagcgaa agcgaaattc tgccgggcga aaaccaggtg   1680
ttttacgata ccgtacccca gaacgtggat tacctgaaca gctattacta cctggaaagc   1740
cagaaactga cgataacgt ggaagatttt acctttaccc gcagcattga agaagcgctg    1800
gataacagcg cgaaagttta cacctatttt ccgaccctgg cgaacaaagt taatgcgggt   1860
```

```
gttcagggcg gtctgtttct gatgtgggcg aacgatgtgg tggaagattt caccaccaac   1920
atcctgcgta aagatccct ggataaaatc agcgatgtta gcgcgattat tccgtatatt    1980
ggtccggcgc tgaacattag caatagcgtg cgtcgtggca attttaccga agcgtttgcg   2040
gttaccggtg tgaccattct gctggaagcg tttccggaat ttaccattcc ggcgctgggt   2100
gcgtttgtga tctatagcaa agtgcaggaa cgcaacgaaa tcatcaaaac catcgataac   2160
tgcctggaac agcgtattaa acgctggaaa gatagctatg aatggatgat gggcacctgg   2220
ctgagccgta ttatcaccca gttcaacaac atcagctacc agatgtacga tagcctgaac   2280
tatcaggcgg gtgcgattaa agcgaaaatc gatctggaat acaaaaaata cagcggcagc   2340
gataaagaaa acatcaaaag ccaggttgaa aacctgaaaa acagcctgga tgtgaaaatt   2400
agcgaagcga tgaataacat caacaaattc atccgcgaat gcagcgtgac ctacctgttc   2460
aaaaacatgc tgccgaaagt gatcgatgaa ctgaacgaat ttgatcgcaa caccaaagcg   2520
aaactgatca acctgatcga tagccacaac attattctgg tgggcgaagt ggataaactg   2580
aaagcgaaag ttaacaacag cttccagaac accatcccgt ttaacatctt cagctatacc   2640
aacaacagcc tgctgaaaga tatcatcaac gaatacttca atctagaagc actagcgagt   2700
gggcaccatc accatcacca ttaatgaaag ctt                                2733

<210> SEQ ID NO 16
<211> LENGTH: 909
<212> TYPE: PRT
<213> ORGANISM: Unknown
<220> FEATURE:
<223> OTHER INFORMATION: Protein sequence of the LC/C-RGD-HN/C fusion

<400> SEQUENCE: 16

Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
        195                 200                 205
```

```
Ala Thr Asn Asp Val Gly Glu Gly Arg Phe Ser Lys Ser Glu Phe Cys
210                 215                 220
Met Asp Pro Ile Leu Ile Leu Met His Glu Leu Asn His Ala Met His
225                 230                 235                 240
Asn Leu Tyr Gly Ile Ala Ile Pro Asn Asp Gln Thr Ile Ser Ser Val
                245                 250                 255
Thr Ser Asn Ile Phe Tyr Ser Gln Tyr Asn Val Lys Leu Glu Tyr Ala
                260                 265                 270
Glu Ile Tyr Ala Phe Gly Gly Pro Thr Ile Asp Leu Ile Pro Lys Ser
            275                 280                 285
Ala Arg Lys Tyr Phe Glu Glu Lys Ala Leu Asp Tyr Tyr Arg Ser Ile
            290                 295                 300
Ala Lys Arg Leu Asn Ser Ile Thr Thr Ala Asn Pro Ser Ser Phe Asn
305                 310                 315                 320
Lys Tyr Ile Gly Glu Tyr Lys Gln Lys Leu Ile Arg Lys Tyr Arg Phe
                325                 330                 335
Val Val Glu Ser Ser Gly Glu Val Thr Val Asn Arg Asn Lys Phe Val
                340                 345                 350
Glu Leu Tyr Asn Glu Leu Thr Gln Ile Phe Thr Glu Phe Asn Tyr Ala
            355                 360                 365
Lys Ile Tyr Asn Val Gln Asn Arg Lys Ile Tyr Leu Ser Asn Val Tyr
            370                 375                 380
Thr Pro Val Thr Ala Asn Ile Leu Asp Asp Asn Val Tyr Asp Ile Gln
385                 390                 395                 400
Asn Gly Phe Asn Ile Pro Lys Ser Asn Leu Asn Val Leu Phe Met Gly
                405                 410                 415
Gln Asn Leu Ser Arg Asn Pro Ala Leu Arg Lys Val Asn Pro Glu Asn
            420                 425                 430
Met Leu Tyr Leu Phe Thr Lys Phe Cys Val Asp Ala Ile Asp Gly Arg
            435                 440                 445
Gly Gly Arg Gly Asp Met Phe Gly Ala Ala Leu Ala Gly Gly Gly Gly
450                 455                 460
Ser Gly Gly Gly Gly Ser Gly Gly Gly Ser Ala Leu Val Leu Gln
465                 470                 475                 480
Cys Arg Glu Leu Leu Val Lys Asn Thr Asp Leu Pro Phe Ile Gly Asp
                485                 490                 495
Ile Ser Asp Val Lys Thr Asp Ile Phe Leu Arg Lys Asp Ile Asn Glu
            500                 505                 510
Glu Thr Glu Val Ile Tyr Tyr Pro Asp Asn Val Ser Val Asp Gln Val
            515                 520                 525
Ile Leu Ser Lys Asn Thr Ser Glu His Gly Gln Leu Asp Leu Leu Tyr
            530                 535                 540
Pro Ser Ile Asp Ser Glu Ser Glu Ile Leu Pro Gly Glu Asn Gln Val
545                 550                 555                 560
Phe Tyr Asp Asn Arg Thr Gln Asn Val Asp Tyr Leu Asn Ser Tyr Tyr
                565                 570                 575
Tyr Leu Glu Ser Gln Lys Leu Ser Asp Asn Val Glu Asp Phe Thr Phe
            580                 585                 590
Thr Arg Ser Ile Glu Glu Ala Leu Asp Asn Ser Ala Lys Val Tyr Thr
            595                 600                 605
Tyr Phe Pro Thr Leu Ala Asn Lys Val Asn Ala Gly Val Gln Gly Gly
            610                 615                 620
```

```
Leu Phe Leu Met Trp Ala Asn Asp Val Val Glu Asp Phe Thr Thr Asn
625                 630                 635                 640

Ile Leu Arg Lys Asp Thr Leu Asp Lys Ile Ser Asp Val Ser Ala Ile
            645                 650                 655

Ile Pro Tyr Ile Gly Pro Ala Leu Asn Ile Ser Asn Ser Val Arg Arg
            660                 665                 670

Gly Asn Phe Thr Glu Ala Phe Ala Val Thr Gly Val Thr Ile Leu Leu
            675                 680                 685

Glu Ala Phe Pro Glu Phe Thr Ile Pro Ala Leu Gly Ala Phe Val Ile
            690                 695                 700

Tyr Ser Lys Val Gln Glu Arg Asn Glu Ile Ile Lys Thr Ile Asp Asn
705                 710                 715                 720

Cys Leu Glu Gln Arg Ile Lys Arg Trp Lys Asp Ser Tyr Glu Trp Met
            725                 730                 735

Met Gly Thr Trp Leu Ser Arg Ile Ile Thr Gln Phe Asn Asn Ile Ser
            740                 745                 750

Tyr Gln Met Tyr Asp Ser Leu Asn Tyr Gln Ala Gly Ala Ile Lys Ala
            755                 760                 765

Lys Ile Asp Leu Glu Tyr Lys Lys Tyr Ser Gly Ser Asp Lys Glu Asn
770                 775                 780

Ile Lys Ser Gln Val Glu Asn Leu Lys Asn Ser Leu Asp Val Lys Ile
785                 790                 795                 800

Ser Glu Ala Met Asn Asn Ile Asn Lys Phe Ile Arg Glu Cys Ser Val
            805                 810                 815

Thr Tyr Leu Phe Lys Asn Met Leu Pro Lys Val Ile Asp Glu Leu Asn
            820                 825                 830

Glu Phe Asp Arg Asn Thr Lys Ala Lys Leu Ile Asn Leu Ile Asp Ser
            835                 840                 845

His Asn Ile Ile Leu Val Gly Glu Val Asp Lys Leu Lys Ala Lys Val
850                 855                 860

Asn Asn Ser Phe Gln Asn Thr Ile Pro Phe Asn Ile Phe Ser Tyr Thr
865                 870                 875                 880

Asn Asn Ser Leu Leu Lys Asp Ile Ile Asn Glu Tyr Phe Asn Leu Glu
            885                 890                 895

Ala Leu Ala Ser Gly His His His His His Lys Leu
            900                 905
```

<210> SEQ ID NO 17
<211> LENGTH: 2721
<212> TYPE: DNA
<213> ORGANISM: Unknown
<220> FEATURE:
<223> OTHER INFORMATION: DNA sequence of the fully synthesised LC/C-RGD-HN/C fusion

<400> SEQUENCE: 17

```
catatgggct ccgaatttat gccgataaca attaacaatt tcaattactc ggatccggtg      60
gacaacaaaa acattctgta tctggataca catttaaata ctcttgcgaa tgaaccagaa     120
aaagcgttca gaattacggg aaatatctgg gtcatcccgg atcgcttttc gagaaactca     180
aaccccaacc tgaacaaacc gccccgtgtt acaagtccga aaagcggcta ttacgatcca     240
aactaccttt cgaccgactc ggacaaagat acgtttctta agagataat taaactgttt     300 aaacgtatca attcacgcga aattggggaa gagttaattt accgcctctc caccgacatt     360
ccgtttccag gcaataacaa tacaccgatt aacacctttg atttcgacgt ggacttcaac     420
```

```
agcgtggatg ttaaaacgcg ccagggtaat aactgggtaa agacgggatc gattaacccg    480
agtgttatta tcaccggtcc tcgcgaaaat atcatagacc cggaaactag cacgtttaaa    540
cttactaata acacattcgc ggcccaagaa gggttcggcg ccctgtcaat tataagcatc    600
agtccgcgct ttatgctgac ttacagtaat gctactaatg acgtgggtga gggccggttc    660
tctaaatcag aattttgcat ggatccaatc ctgattctga tgcatgagct gaatcacgct    720
atgcacaatc tgtatggtat tgctattccg aacgatcaga caattagttc agtgacgtct    780
aacatattct attctcaata taatgtgaaa ttggagtatg cggaaattta tgcatttggt    840
ggcccaacca tcgatcttat cccaaaatcc gcgcgcaagt atttcgaaga gaaagcatta    900
gattattacc ggtctatcgc aaagcgtctg aatagcataa ctacggctaa tccgagttcg    960
tttaacaaat atattggcga atataaacag aaactgatcc gtaaatatcg tttcgtagtg   1020
gaatcatccg gtgaagttac agtcaatcgt aataaatttg tggagttata caatgagctg   1080
acccaaatct tcaccgaatt caactatgct aaaatttata atgttcagaa ccgcaaaatc   1140
tacctgagta acgtgtatac gcctgtaaca gccaatattc tggatgacaa cgtgtatgat   1200
atccagaatg gctttaacat acctaaaagt aacttgaatg ttctctttat gggtcaaaat   1260
cttttcccgca atccggctct ccgaaaggta atccggaaa acatgctcta tcttttcacc   1320
aaattttgcg tcgacgcaat cgatggacgt ggtgggagag gtgatatgtt tggggccgca   1380
ttagcgggtg gcgggggatc cggcggtggc ggtagtggcg ggggcggaag cgcgctggta   1440
ctgcagtgtc gcgaactttt agttaagaat actgatctgc cattcattgg tgatatctca   1500
gatgtcaaga ccgatatttt cctccgtaaa gatatcaatg aggaaacaga ggtaatttac   1560
tatccggata atgtatctgt cgatcaggtc attctgtcca aaaataccctc tgaacacggt   1620
caactggatc tgctctaccc ctcgattgac tccgaatctg aaatcctccc tggagaaaac   1680
caggtctttt atgacaatcg tacccagaac gtggactact aaactctta ttactatttg   1740
gagagccaaa agttgtccga taacgttgaa gactttactt ttacccgatc tatagaagag   1800
gcattagaca actcggcgaa ggtttacacc tatttcccta ccttagccaa taaagtgaac   1860
gcaggtgtgc agggagggct gtttttgatg tgggccaatg atgtcgttga ggatttcaca   1920
accaacattc tgcgcaaaga cactttagat aaaatctcag atgtatcggc gatcattccc   1980
tacattggcc ctgcccttaa catttctaat tccgttcgtc gcggcaattt tactgaggcg   2040
tttgctgtca ccggtgtgac gatcttgctg gaggcttttc ctgaatttac cattcccgca   2100
ctggggcat tcgttatcta cagtaaggtt caggaacgga acgaaattat aaaaacaatc   2160
gataattgcc tggaacagcg tatcaaacgg tggaaagata gctacgaatg gatgatgggc   2220
acgtggttga ccgcataat tacgcagttt aataacatct catatcaaat gtatgactcc   2280
ctgaattacc aggcgggcgc gattaaagcc aaaatcgatc tggagtacaa aaagtattca   2340
ggcagcgaca agagaacat taaaagtcag gttgaaaacc tgaagaattc actggatgtg   2400
aaaatcagcg aagccatgaa taacattaat aaattcatcc gtgaatgtag tgtgacctat   2460
ctctttaaga atatgttgcc gaaagttatc gatgagctga acgagtttga tcgaaatacc   2520
aaagcaaagc tgattaattt aattgacagc cataatatta tactggtcgg cgaagtggat   2580
aaactgaagg ccaaggtaaa caattctttt caaaacacga taccattcaa catctttttct   2640
tatacgaata acagccttct gaaggacatt attaacgaat attttaattt ggaagccttg   2700
gctagcggat aatgaaagct t                                              2721
```

<210> SEQ ID NO 18
<211> LENGTH: 902
<212> TYPE: PRT
<213> ORGANISM: Unknown
<220> FEATURE:
<223> OTHER INFORMATION: Protein sequence of the fully synthesised LC/C-RGD-HN/C fusion

<400> SEQUENCE: 18

```
Met Gly Ser Glu Phe Met Pro Ile Thr Ile Asn Asn Phe Asn Tyr Ser
1               5                   10                  15

Asp Pro Val Asp Asn Lys Asn Ile Leu Tyr Leu Asp Thr His Leu Asn
            20                  25                  30

Thr Leu Ala Asn Glu Pro Glu Lys Ala Phe Arg Ile Thr Gly Asn Ile
        35                  40                  45

Trp Val Ile Pro Asp Arg Phe Ser Arg Asn Ser Asn Pro Asn Leu Asn
    50                  55                  60

Lys Pro Pro Arg Val Thr Ser Pro Lys Ser Gly Tyr Tyr Asp Pro Asn
65                  70                  75                  80

Tyr Leu Ser Thr Asp Ser Asp Lys Asp Thr Phe Leu Lys Glu Ile Ile
                85                  90                  95

Lys Leu Phe Lys Arg Ile Asn Ser Arg Glu Ile Gly Glu Glu Leu Ile
            100                 105                 110

Tyr Arg Leu Ser Thr Asp Ile Pro Phe Pro Gly Asn Asn Asn Thr Pro
        115                 120                 125

Ile Asn Thr Phe Asp Phe Asp Val Asp Phe Asn Ser Val Asp Val Lys
    130                 135                 140

Thr Arg Gln Gly Asn Asn Trp Val Lys Thr Gly Ser Ile Asn Pro Ser
145                 150                 155                 160

Val Ile Ile Thr Gly Pro Arg Glu Asn Ile Ile Asp Pro Glu Thr Ser
                165                 170                 175

Thr Phe Lys Leu Thr Asn Asn Thr Phe Ala Ala Gln Glu Gly Phe Gly
            180                 185                 190

Ala Leu Ser Ile Ile Ser Ile Ser Pro Arg Phe Met Leu Thr Tyr Ser
        195                 200                 205

Asn Ala Thr Asn Asp Val Gly Glu Gly Arg Phe Ser Lys Ser Glu Phe
    210                 215                 220

Cys Met Asp Pro Ile Leu Ile Leu Met His Glu Leu Asn His Ala Met
225                 230                 235                 240

His Asn Leu Tyr Gly Ile Ala Ile Pro Asn Asp Gln Thr Ile Ser Ser
                245                 250                 255

Val Thr Ser Asn Ile Phe Tyr Ser Gln Tyr Asn Val Lys Leu Glu Tyr
            260                 265                 270

Ala Glu Ile Tyr Ala Phe Gly Gly Pro Thr Ile Asp Leu Ile Pro Lys
        275                 280                 285

Ser Ala Arg Lys Tyr Phe Glu Glu Lys Ala Leu Asp Tyr Tyr Arg Ser
    290                 295                 300

Ile Ala Lys Arg Leu Asn Ser Ile Thr Thr Ala Asn Pro Ser Ser Phe
305                 310                 315                 320

Asn Lys Tyr Ile Gly Glu Tyr Lys Gln Lys Leu Ile Arg Lys Tyr Arg
                325                 330                 335

Phe Val Val Glu Ser Ser Gly Glu Val Thr Val Asn Arg Asn Lys Phe
            340                 345                 350

Val Glu Leu Tyr Asn Glu Leu Thr Gln Ile Phe Thr Glu Phe Asn Tyr
        355                 360                 365
```

-continued

```
Ala Lys Ile Tyr Asn Val Gln Asn Arg Lys Ile Tyr Leu Ser Asn Val
    370                 375                 380

Tyr Thr Pro Val Thr Ala Asn Ile Leu Asp Asp Asn Val Tyr Asp Ile
385                 390                 395                 400

Gln Asn Gly Phe Asn Ile Pro Lys Ser Asn Leu Asn Val Leu Phe Met
                405                 410                 415

Gly Gln Asn Leu Ser Arg Asn Pro Ala Leu Arg Lys Val Asn Pro Glu
            420                 425                 430

Asn Met Leu Tyr Leu Phe Thr Lys Phe Cys Val Asp Ala Ile Asp Gly
        435                 440                 445

Arg Gly Arg Gly Asp Met Phe Gly Ala Ala Leu Ala Gly Gly Gly
450                 455                 460

Gly Ser Gly Gly Gly Ser Gly Gly Gly Ser Ala Leu Val Leu
465             470                 475                 480

Gln Cys Arg Glu Leu Leu Val Lys Asn Thr Asp Leu Pro Phe Ile Gly
            485                 490                 495

Asp Ile Ser Asp Val Lys Thr Asp Ile Phe Leu Arg Lys Asp Ile Asn
            500                 505                 510

Glu Glu Thr Glu Val Ile Tyr Tyr Pro Asp Asn Val Ser Val Asp Gln
        515                 520                 525

Val Ile Leu Ser Lys Asn Thr Ser Glu His Gly Gln Leu Asp Leu Leu
530                 535                 540

Tyr Pro Ser Ile Asp Ser Glu Ser Glu Ile Leu Pro Gly Glu Asn Gln
545                 550                 555                 560

Val Phe Tyr Asp Asn Arg Thr Gln Asn Val Asp Tyr Leu Asn Ser Tyr
                565                 570                 575

Tyr Tyr Leu Glu Ser Gln Lys Leu Ser Asp Asn Val Glu Asp Phe Thr
            580                 585                 590

Phe Thr Arg Ser Ile Glu Glu Ala Leu Asp Asn Ser Ala Lys Val Tyr
        595                 600                 605

Thr Tyr Phe Pro Thr Leu Ala Asn Lys Val Asn Ala Gly Val Gln Gly
    610                 615                 620

Gly Leu Phe Leu Met Trp Ala Asn Asp Val Val Glu Asp Phe Thr Thr
625                 630                 635                 640

Asn Ile Leu Arg Lys Asp Thr Leu Asp Lys Ile Ser Asp Val Ser Ala
                645                 650                 655

Ile Ile Pro Tyr Ile Gly Pro Ala Leu Asn Ile Ser Asn Ser Val Arg
            660                 665                 670

Arg Gly Asn Phe Thr Glu Ala Phe Ala Val Thr Gly Val Thr Ile Leu
        675                 680                 685

Leu Glu Ala Phe Pro Glu Phe Thr Ile Pro Ala Leu Gly Ala Phe Val
    690                 695                 700

Ile Tyr Ser Lys Val Gln Glu Arg Asn Glu Ile Ile Lys Thr Ile Asp
705                 710                 715                 720

Asn Cys Leu Glu Gln Arg Ile Lys Arg Trp Lys Asp Ser Tyr Glu Trp
                725                 730                 735

Met Met Gly Thr Trp Leu Ser Arg Ile Ile Thr Gln Phe Asn Asn Ile
            740                 745                 750

Ser Tyr Gln Met Tyr Asp Ser Leu Asn Tyr Gln Ala Gly Ala Ile Lys
        755                 760                 765

Ala Lys Ile Asp Leu Glu Tyr Lys Lys Tyr Ser Gly Ser Asp Lys Glu
    770                 775                 780

Asn Ile Lys Ser Gln Val Glu Asn Leu Lys Asn Ser Leu Asp Val Lys
```

```
                 785                 790                 795                 800
Ile Ser Glu Ala Met Asn Asn Ile Asn Lys Phe Ile Arg Glu Cys Ser
                805                 810                 815

Val Thr Tyr Leu Phe Lys Asn Met Leu Pro Lys Val Ile Asp Glu Leu
                820                 825                 830

Asn Glu Phe Asp Arg Asn Thr Lys Ala Lys Leu Ile Asn Leu Ile Asp
                835                 840                 845

Ser His Asn Ile Ile Leu Val Gly Glu Val Asp Lys Leu Lys Ala Lys
                850                 855                 860

Val Asn Asn Ser Phe Gln Asn Thr Ile Pro Phe Asn Ile Phe Ser Tyr
865                 870                 875                 880

Thr Asn Asn Ser Leu Leu Lys Asp Ile Ile Asn Glu Tyr Phe Asn Leu
                885                 890                 895

Glu Ala Leu Ala Ser Gly
                900

<210> SEQ ID NO 19
<211> LENGTH: 2859
<212> TYPE: DNA
<213> ORGANISM: Unknown
<220> FEATURE:
<223> OTHER INFORMATION: DNA sequence of the fully synthesised EGF-LHN/C
      fusion

<400> SEQUENCE: 19
catatgattt ccgaatttgg ctcggagttc atgccaatta cgattaacaa ttttaactat      60
agtgatccgg tggataataa aacatttta tacctggata cccacttgaa tactcttgcc     120
aatgagcctg aaaaagcctt tcgcataacg ggtaacattt gggtcattcc ggaccgtttt    180
agccggaact ctaaccctaa tctgaataaa cctccgcgtg tcacgtctcc gaaaagtggg    240
tattacgatc caaattatct gagtaccgat tcagacaagg atacgtttct gaaagaaatc    300
ataaaacttt tcaaaagaat caactcccgt gaaatcggtg aagagctgat ctaccgtctg    360
tcgacggaca ttccttttcc gggaaacaat aacactccca ttaatacctt cgactttgat    420
gtcgatttca actcagtcga tgtgaaaacc cgccagggta taactgggt taaaactgga    480
tccattaacc cgtccgttat tatcacaggt cctcgtgaaa atattataga tcctgagacc    540
tccacgttca agctgacgaa taacactttt gcggcacagg aagggtttgg tgccccttca    600
attatctcta tctctccgcg cttcatgtta acgtattcta acgcaaccaa cgatgttggc    660
gagggccgct tcagcaaaag tgaattctgt atggatccca ttctgatctt gatgcatgag    720
cttaaccacg ctatgcataa tctttatggt attgcaatcc caaacgatca gacgatctcc    780
agcgttacat ctaacatatt ctacagccaa tataatgtga agctcgaata tgcagagatt    840
tacgccttcg gtgggccgac cattgacctc attccaaagt ctgcccgtaa gtactttgag    900
gaaaaagcgt tggattacta tcgtagcatc gcgaaacgcc tgaattcaat tcaactgcaa    960
aacccatcta gcttcaacaa atacatcgga gaatataaac aaaagctgat acgcaaatat   1020
cgctttgtgg tcgaatcgtc cggggaagtg acagttaatc gaaataaatt tgttgaactc   1080
tataatgaat taacgcagat cttcacagaa tttaattatg ctaaaatcta taatgtacag   1140
aaccggaaaa tttatctcag taatgtatac acaccggtga ctgctaacat tctggacgat   1200
aacgtctacg atattcaaaa tggctttaat atcccgaaga gcaacttgaa tgtcctcttc   1260
atggggcaga acttgtcacg taaccccgcg ctgcgaaaag ttaacccaga aaatatgttg   1320
tacctcttta caaaattctg tgtagacgcc attgacggac gctcactgta aacaaaacc    1380
```

```
ctgcaatgcc gtgaacttct ggttaagaac accgacctgc cgttcattgg ggacatcagt    1440
gatgtcaaaa cggatatttt tcttcggaag gatattaatg aggaaaccga agtgatatac    1500
tatcctgaca atgtgtcggt agatcaggta atcctgagta agaacaccag cgagcatggg    1560
cagctggatc tgttgtatcc gagcattgac agcgagtcgg aaatactgcc cggcgaaaat    1620
caagtttttt atgacaatcg gacccagaat gttgattatc tgaatagtta ctattacttg    1680
gagagccaaa aattatcaga taatgtgaaa gactttacct ttacccggtc tatcgaagag    1740
gcgctggata acagcgcgaa agtttacact tattttccca cgctcgcaaa caaagttaat    1800
gctggcgtac agggtggatt atttcttatg tgggcgaatg atgtggtaga ggactttaca    1860
accaacatcc tgcgcaaaga cactttagac aaaatttctg acgtctcggc cattatcccg    1920
tatataggtc cggccttaaa cataagcaat tcggttcgcc gtggcaactt cacagaagcc    1980
ttcgctgtga ctggtgtgac cattctgttg gaagcatttc ctgagtttac gatcccggct    2040
ctgggcgcat ttgtaatttta ctctaaagtt caggaacgaa atgaaattat aaaaactatc    2100
gataattgcc tggaacagcg tatcaagaga tggaaggatt cctatgagtg gatgatgggg    2160
acctggctgt caagaattat cacacagttt aataacatat cctatcaaat gtatgatagc    2220
ttaaactatc aagcaggagc gataaaggcg aaaattgacc tggaatacaa gaaatattct    2280
ggttcggata agagaatat taaaagtcag gtggaaaatc tgaaaaatag tttagatgtc    2340
aaaatttctg aggcgatgaa taacattaac aaattcatcc gcgagtgcag tgtaacttat    2400
ttgtttaaga atatgttacc caaagttatc gacgaactga atgaatttga tcgtaatacc    2460
aaagccaaat tgatcaacct catcgactct cataacatca ttctggtggg agaagtcgac    2520
aaactgaaag ctaaggtgaa taacagcttc cagaatacaa ttccgtttaa tatttctca    2580 tacaccaata actcgctgct aaagatatt atcaacgaat attttaatct ggagggtggc    2640
ggtggcagtg gcggtggcgg atccggcggt ggcggtagcg cactggataa ttcagattcc    2700
gaatgtccac tgtcacacga tggttattgt cttcatgatg gcgtgtgcat gtatatagaa    2760
gcgttagata aatacgcttg caactgcgtg gttggctata tcggcgaacg ttgtcagtat    2820
cgtgatttaa agtggtggga attacgctaa tgaaagctt                            2859
```

<210> SEQ ID NO 20
<211> LENGTH: 948
<212> TYPE: PRT
<213> ORGANISM: Unknown
<220> FEATURE:
<223> OTHER INFORMATION: Protein sequence of the fully synthesised
      EGF-LHN/C fusion <400> SEQUENCE: 20

```
Met Ile Ser Glu Phe Gly Ser Glu Phe Met Pro Ile Thr Ile Asn Asn
1               5                   10                  15

Phe Asn Tyr Ser Asp Pro Val Asp Asn Lys Asn Ile Leu Tyr Leu Asp
            20                  25                  30

Thr His Leu Asn Thr Leu Ala Asn Glu Pro Glu Lys Ala Phe Arg Ile
        35                  40                  45

Thr Gly Asn Ile Trp Val Ile Pro Asp Arg Phe Ser Arg Asn Ser Asn
    50                  55                  60

Pro Asn Leu Asn Lys Pro Pro Arg Val Thr Ser Pro Lys Ser Gly Tyr
65                  70                  75                  80

Tyr Asp Pro Asn Tyr Leu Ser Thr Asp Ser Asp Lys Asp Thr Phe Leu
                85                  90                  95
```

```
Lys Glu Ile Ile Lys Leu Phe Lys Arg Ile Asn Ser Arg Glu Ile Gly
            100                 105                 110

Glu Glu Leu Ile Tyr Arg Leu Ser Thr Asp Ile Pro Phe Pro Gly Asn
        115                 120                 125

Asn Asn Thr Pro Ile Asn Thr Phe Asp Phe Asp Val Asp Phe Asn Ser
130                 135                 140

Val Asp Val Lys Thr Arg Gln Gly Asn Asn Trp Val Lys Thr Gly Ser
145                 150                 155                 160

Ile Asn Pro Ser Val Ile Ile Thr Gly Pro Arg Glu Asn Ile Ile Asp
                165                 170                 175

Pro Glu Thr Ser Thr Phe Lys Leu Thr Asn Asn Thr Phe Ala Ala Gln
            180                 185                 190

Glu Gly Phe Gly Ala Leu Ser Ile Ile Ser Ile Ser Pro Arg Phe Met
        195                 200                 205

Leu Thr Tyr Ser Asn Ala Thr Asn Asp Val Gly Glu Gly Arg Phe Ser
210                 215                 220

Lys Ser Glu Phe Cys Met Asp Pro Ile Leu Ile Leu Met His Glu Leu
225                 230                 235                 240

Asn His Ala Met His Asn Leu Tyr Gly Ile Ala Ile Pro Asn Asp Gln
                245                 250                 255

Thr Ile Ser Ser Val Thr Ser Asn Ile Phe Tyr Ser Gln Tyr Asn Val
            260                 265                 270

Lys Leu Glu Tyr Ala Glu Ile Tyr Ala Phe Gly Gly Pro Thr Ile Asp
        275                 280                 285

Leu Ile Pro Lys Ser Ala Arg Lys Tyr Phe Glu Glu Lys Ala Leu Asp
290                 295                 300

Tyr Tyr Arg Ser Ile Ala Lys Arg Leu Asn Ser Ile Thr Thr Ala Asn
305                 310                 315                 320

Pro Ser Ser Phe Asn Lys Tyr Ile Gly Glu Tyr Lys Gln Lys Leu Ile
                325                 330                 335

Arg Lys Tyr Arg Phe Val Val Glu Ser Ser Gly Glu Val Thr Val Asn
            340                 345                 350

Arg Asn Lys Phe Val Glu Leu Tyr Asn Glu Leu Thr Gln Ile Phe Thr
        355                 360                 365

Glu Phe Asn Tyr Ala Lys Ile Tyr Asn Val Gln Asn Arg Lys Ile Tyr
370                 375                 380

Leu Ser Asn Val Tyr Thr Pro Val Thr Ala Asn Ile Leu Asp Asp Asn
385                 390                 395                 400

Val Tyr Asp Ile Gln Asn Gly Phe Asn Ile Pro Lys Ser Asn Leu Asn
                405                 410                 415

Val Leu Phe Met Gly Gln Asn Leu Ser Arg Asn Pro Ala Leu Arg Lys
            420                 425                 430

Val Asn Pro Glu Asn Met Leu Tyr Leu Phe Thr Lys Phe Cys Val Asp
        435                 440                 445

Ala Ile Asp Gly Arg Ser Leu Tyr Asn Lys Thr Leu Gln Cys Arg Glu
450                 455                 460

Leu Leu Val Lys Asn Thr Asp Leu Pro Phe Ile Gly Asp Ile Ser Asp
465                 470                 475                 480

Val Lys Thr Asp Ile Phe Leu Arg Lys Asp Ile Asn Glu Glu Thr Glu
                485                 490                 495

Val Ile Tyr Tyr Pro Asp Asn Val Ser Val Asp Gln Val Ile Leu Ser
            500                 505                 510
```

```
Lys Asn Thr Ser Glu His Gly Gln Leu Asp Leu Leu Tyr Pro Ser Ile
            515                 520                 525

Asp Ser Glu Ser Glu Ile Leu Pro Gly Glu Asn Gln Val Phe Tyr Asp
            530                 535                 540

Asn Arg Thr Gln Asn Val Asp Tyr Leu Asn Ser Tyr Tyr Leu Glu
545                 550                 555                 560

Ser Gln Lys Leu Ser Asp Asn Val Glu Asp Phe Thr Phe Thr Arg Ser
                565                 570                 575

Ile Glu Glu Ala Leu Asp Asn Ser Ala Lys Val Tyr Thr Tyr Phe Pro
                    580                 585                 590

Thr Leu Ala Asn Lys Val Asn Ala Gly Val Gln Gly Gly Leu Phe Leu
                595                 600                 605

Met Trp Ala Asn Asp Val Val Glu Asp Phe Thr Thr Asn Ile Leu Arg
            610                 615                 620

Lys Asp Thr Leu Asp Lys Ile Ser Asp Val Ser Ala Ile Ile Pro Tyr
625                 630                 635                 640

Ile Gly Pro Ala Leu Asn Ile Ser Asn Ser Val Arg Arg Gly Asn Phe
                    645                 650                 655

Thr Glu Ala Phe Ala Val Thr Gly Val Thr Ile Leu Leu Glu Ala Phe
                660                 665                 670

Pro Glu Phe Thr Ile Pro Ala Leu Gly Ala Phe Val Ile Tyr Ser Lys
            675                 680                 685

Val Gln Glu Arg Asn Glu Ile Ile Lys Thr Ile Asp Asn Cys Leu Glu
                690                 695                 700

Gln Arg Ile Lys Arg Trp Lys Asp Ser Tyr Glu Trp Met Met Gly Thr
705                 710                 715                 720

Trp Leu Ser Arg Ile Ile Thr Gln Phe Asn Asn Ile Ser Tyr Gln Met
                    725                 730                 735

Tyr Asp Ser Leu Asn Tyr Gln Ala Gly Ala Ile Lys Ala Lys Ile Asp
                740                 745                 750

Leu Glu Tyr Lys Lys Tyr Ser Gly Ser Asp Lys Glu Asn Ile Lys Ser
            755                 760                 765

Gln Val Glu Asn Leu Lys Asn Ser Leu Asp Val Lys Ile Ser Glu Ala
770                 775                 780

Met Asn Asn Ile Asn Lys Phe Ile Arg Glu Cys Ser Val Thr Tyr Leu
785                 790                 795                 800

Phe Lys Asn Met Leu Pro Lys Val Ile Asp Glu Leu Asn Glu Phe Asp
                    805                 810                 815

Arg Asn Thr Lys Ala Lys Leu Ile Asn Leu Ile Asp Ser His Asn Ile
                820                 825                 830

Ile Leu Val Gly Glu Val Asp Lys Leu Lys Ala Lys Val Asn Asn Ser
            835                 840                 845

Phe Gln Asn Thr Ile Pro Phe Asn Ile Phe Ser Tyr Thr Asn Asn Ser
850                 855                 860

Leu Leu Lys Asp Ile Ile Asn Glu Tyr Phe Asn Leu Glu Gly Gly Gly
865                 870                 875                 880

Gly Ser Gly Gly Gly Gly Ser Gly Gly Gly Gly Ser Ala Leu Asp Asn
                    885                 890                 895

Ser Asp Ser Glu Cys Pro Leu Ser His Asp Gly Tyr Cys Leu His Asp
                900                 905                 910

Gly Val Cys Met Tyr Ile Glu Ala Leu Asp Lys Tyr Ala Cys Asn Cys
            915                 920                 925

Val Val Gly Tyr Ile Gly Glu Arg Cys Gln Tyr Arg Asp Leu Lys Trp
```

Trp Glu Leu Arg
945

<210> SEQ ID NO 21
<211> LENGTH: 9
<212> TYPE: PRT
<213> ORGANISM: Unknown
<220> FEATURE:
<223> OTHER INFORMATION: Integrin binding peptide sequence

<400> SEQUENCE: 21

Gly Gly Arg Gly Asp Met Phe Gly Ala
1               5

<210> SEQ ID NO 22
<211> LENGTH: 11
<212> TYPE: PRT
<213> ORGANISM: Unknown
<220> FEATURE:
<223> OTHER INFORMATION: Integrin binding peptide sequence

<400> SEQUENCE: 22

Gly Gly Cys Arg Gly Asp Met Phe Gly Cys Ala
1               5                   10

<210> SEQ ID NO 23
<211> LENGTH: 5
<212> TYPE: PRT
<213> ORGANISM: Unknown
<220> FEATURE:
<223> OTHER INFORMATION: cyclic RGD peptide
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: N-methyl-Val

<400> SEQUENCE: 23

Arg Gly Asp Phe Val
1               5

<210> SEQ ID NO 24
<211> LENGTH: 10
<212> TYPE: PRT
<213> ORGANISM: Unknown
<220> FEATURE:
<223> OTHER INFORMATION: linear integrin binding sequence

<400> SEQUENCE: 24

Pro Leu Ala Glu Ile Asp Gly Ile Glu Leu
1               5                   10

<210> SEQ ID NO 25
<211> LENGTH: 12
<212> TYPE: PRT
<213> ORGANISM: Unknown
<220> FEATURE:
<223> OTHER INFORMATION: cyclic integrin binding sequence

<400> SEQUENCE: 25

Cys Pro Leu Ala Glu Ile Asp Gly Ile Glu Leu Cys
1               5                   10

```
<210> SEQ ID NO 26
<211> LENGTH: 6
<212> TYPE: PRT
<213> ORGANISM: Unknown
<220> FEATURE:
<223> OTHER INFORMATION: linear integrin binding sequence

<400> SEQUENCE: 26

Gly Arg Gly Asp Ser Pro
1               5

<210> SEQ ID NO 27
<211> LENGTH: 6
<212> TYPE: PRT
<213> ORGANISM: Unknown
<220> FEATURE:
<223> OTHER INFORMATION: linear integrin binding sequence

<400> SEQUENCE: 27

Gly Arg Gly Glu Ser Pro
1               5

<210> SEQ ID NO 28
<211> LENGTH: 5
<212> TYPE: PRT
<213> ORGANISM: Unknown
<220> FEATURE:
<223> OTHER INFORMATION: spacer molecule

<400> SEQUENCE: 28

Gly Gly Gly Gly Ser
1               5

<210> SEQ ID NO 29
<211> LENGTH: 7
<212> TYPE: PRT
<213> ORGANISM: Unknown
<220> FEATURE:
<223> OTHER INFORMATION: spacer molecule

<400> SEQUENCE: 29

Pro Pro Pro Ile Glu Gly Arg
1               5

<210> SEQ ID NO 30
<211> LENGTH: 7
<212> TYPE: PRT
<213> ORGANISM: Unknown
<220> FEATURE:
<223> OTHER INFORMATION: seroptype B linker

<400> SEQUENCE: 30

Lys Ser Val Lys Ala Pro Gly
1               5

<210> SEQ ID NO 31
<211> LENGTH: 20
<212> TYPE: PRT
<213> ORGANISM: Unknown
<220> FEATURE:
<223> OTHER INFORMATION: protease cleavage site

<400> SEQUENCE: 31

Val Asp Glu Glu Lys Leu Tyr Asp Asp Asp Lys Asp Arg Trp Gly
1               5                   10                  15

Ser Ser Leu Gln
            20
```

```
<210> SEQ ID NO 32
<211> LENGTH: 15
<212> TYPE: PRT
<213> ORGANISM: Unknown
<220> FEATURE:
<223> OTHER INFORMATION: serotype C linker

<400> SEQUENCE: 32

His Lys Ala Ile Asp Gly Arg Ser Leu Tyr Asn Lys Thr Leu Asp
1               5                   10                  15

<210> SEQ ID NO 33
<211> LENGTH: 23
<212> TYPE: PRT
<213> ORGANISM: Unknown
<220> FEATURE:
<223> OTHER INFORMATION: protease cleavage site

<400> SEQUENCE: 33

Val Asp Gly Ile Ile Thr Ser Lys Thr Lys Ser Asp Asp Asp Lys
1               5                   10                  15

Asn Lys Ala Leu Asn Leu Gln
            20
```

INHIBITION OF SECRETION FROM NON-NEURONAL CELLS

This application is continuation of U.S. patent application Ser. No. 13/022,184, filed on Feb. 7, 2011, which is a continuation of U.S. patent application Ser. No. 11/806,648, filed on Jun. 1, 2007, abandoned, which is a continuation-in-part of U.S. patent application Ser. No. 11/327,855, filed on Jan. 9, 2006, abandoned, which is a continuation of U.S. patent application Ser. No. 10/088,665, filed Aug. 14, 2002, abandoned, which is a national phase entry of PCT/GB00/03681, filed Sep. 25, 2000, which claims the benefit of priority of GB 9922558.3, filed Sep. 23, 1999. Each of these applications is hereby incorporated by reference in their entirety.

Pursuant to the provisions of 37 C.F.R. §1.52(e)(5), the sequence listing text file named 82047_Seq_Listing.txt, created on Jan. 6, 2012 and having a size of 93,135 bytes, and which is being submitted herewith, is incorporated by reference herein in its entirety.

The present invention relates to treatment of disease by inhibition of cellular secretory processes, to agents and compositions therefor, and to manufacture of those agents and compositions. The present invention relates particularly, to treatment of diseases dependent upon the exocytotic activity of endocrine cells, exocrine cells, inflammatory cells, cells of the immune system, cells of the cardiovascular system and bone cells.

Exocytosis is the fusion of secretory vesicles with the plasma membrane and results in the discharge of vesicle content—a process also known as cell secretion. Exocytosis can be constitutive or regulated. Constitutive exocytosis is thought to occur in every cell type whereas regulated exocytosis occurs from specialised cells.

The understanding of the mechanisms involved in exocytosis has increased rapidly, following the proposal of the SNARE hypothesis (Rothman, 1994, Nature 372, 55-63). This hypothesis describes protein markers on vesicles, which recognise target membrane markers. These so-called cognate SNARES (denoted v-SNARE for vesicle and t-SNARE for target) facilitate docking and fusion of vesicles with the correct membranes, thus directing discharge of the vesicular contents into the appropriate compartment. Key to the understanding of this process has been the identification of the proteins involved. Three SNARE protein families have been identified for exocytosis: SNAP-25 and SNAP-23, and syntaxins are the t-SNARE families in the membrane; and VAMPs (vesicle-associated membrane protein), including synaptobrevin and cellubrevin, are the v-SNARE family on secretory vesicles. Key components of the fusion machinery including SNARES are involved in both regulated and constitutive exocytosis (De Camilli, 1993, Nature, 364, 387-388).

The clostridial neurotoxins are proteins with molecular masses of the order of 150 kDa. They are produced by various species of the genus *Clostridium*, most importantly *C. tetani* and several strains of *C. botulinum*. There are at present eight different classes of the neurotoxins known: tetanus toxin and botulinum neurotoxin in its serotypes A, B, $C_1$, D, E, F and G, and they all share similar structures and modes of action. The clostridial neurotoxins are synthesized by the bacterium as a single polypeptide that is modified post-translationally to form two polypeptide chains joined together by a disulphide bond. The two chains are termed the heavy chain (H) which has a molecular mass of approximately 100 kDa and the light chain (LC) which has a molecular mass of approximately 50 kDa. The clostridial neurotoxins are highly selective for neuronal cells, and bind with high affinity thereto [see Black, J. D. and Dolly, J. O. (1987) Selective location of acceptors for BoNT/A in the central and peripheral nervous systems. Neuroscience, 23, pp. 767-779; Habermann, E. and Dreyer, F. (1986) Clostridial neurotoxins:handling and action at the cellular and molecular level. Curr. Top. Microbiol. Immunol. 129, pp. 93-179; and Sugiyama, H. (1980) *Clostridium botulinum* neurotoxin. Microbiol. Rev., 44, pp. 419-448 (and internally cited references)].

The functional requirements of neurointoxication by the clostridial neurotoxins can be assigned to specific domains within the neurotoxin structure. The clostridial neurotoxins bind to an acceptor site on the cell membrane of the motor neuron at the neuromuscular junction and, following binding to the highly specific receptor, are internalised by an endocytotic mechanism. The specific neuromuscular junction binding activity of clostridial neurotoxins is known to reside in the carboxy-terminal portion of the heavy chain component of the dichain neurotoxin molecule, a region known as $H_C$. The internalised clostridial neurotoxins possess a highly specific zinc-dependent endopeptidase activity that hydrolyses a specific peptide bond in at least one of three protein families, synaptobrevin, syntaxin or SNAP-25, which are crucial components of the neurosecretory machinery. The zinc-dependent endopeptidase activity of clostridial neurotoxins is found to reside in the L-chain (LC). The amino-terminal portion of the heavy chain component of the dichain neurotoxin molecule, a region known as $H_N$, is responsible for translocation of the neurotoxin, or a portion of it containing the endopeptidase activity, across the endosomal membrane following internalisation, thus allowing access of the endopeptidase to the neuronal cytosol and its substrate protein(s). The result of neurointoxication is inhibition of neurotransmitter release from the target neuron due to prevention of release of synaptic vesicle contents.

The mechanism by which the $H_N$ domain effects translocation of the endopeptidase into the neuronal cytosol is not fully characterised but is believed to involve a conformational change, insertion into the endosomal membrane and formation of some form of channel or pore through which the endopeptidase can gain access to the neuronal cytosol. Following binding to its specific receptor at the neuronal surface pharmacological and morphologic evidence indicate that the clostridial neurotoxins enter the cell by endocytosis [Black & Dolly (1986) J. Cell Biol. 103, 535-44] and then have to pass through a low pH step for neuron intoxication to occur [Simpson et al (1994) J. Pharmacol Exp. Ther., 269, 256-62]. Acidic pH does not activate the toxin directly via a structural change, but is believed to trigger the process of LC membrane translocation from the neuronal endosomal vesicle lumen to the neuronal cytosol [Montecucco et al (1994) FEBS Lett. 346, 92-98]. There is a general consensus that toxin-determined channels are related to the translocation process into the cytosol [Schiavo & Montecucco (1997) in Bacterial Toxins (ed. K. Aktories)]. This model requires that the $H_N$ domain forms a transmembrane hydrophobic pore across the acidic vesicle membrane that allows the partially unfolded LC passage through to the cytosol. The requisite conformational change is believed to be triggered by environmental factors in the neuronal endosomal compartment into which the neurotoxin is internalised, and a necessary feature of the binding domain of the $H_C$ is to target binding sites which enable internalisation into the appropriate endosomal compartment. Therefore clostridial neurotoxins have evolved to target cell surface moieties that fulfil this requirement.

Hormones are chemical messengers that are secreted by the endocrine glands of the body. They exercise specific physiological actions on other organs to which they are carried by the blood. The range of processes regulated by hormones includes various aspects of homeostasis (e.g. insulin regulates the concentration of glucose in the blood), growth (e.g. growth hormone promotes growth and regulates fat, carbohydrate and protein metabolism), and maturation (e.g. sex hormones promote sexual maturation and reproduction). Endocrine hyperfunction results in disease conditions which are caused by excessive amounts of a hormone or hormones in the bloodstream. The causes of hyperfunction are classified as neoplastic, autoimmune, iatrogenic and inflammatory. The endocrine hyperfunction disorders are a complex group of diseases, not only because there is a large number of glands that can cause a pathology (e.g. anterior pituitary, posterior pituitary, thyroid, parathyroid, adrenal cortex, adrenal medulla, pancreas, ovaries, testis) but because many of the glands produce more than one hormone (e.g. the anterior pituitary produces corticotrophin, prolactin, luteinizing hormone, follicle stimulating hormone, thyroid stimulating hormone and gonadotrophins). The majority of disorders that cause hormone excess are due to neoplastic growth of hormone producing cells. However, certain tumours of non-endocrine origin can synthesise hormones causing endocrine hyperfunction disease symptoms. The hormone production under these conditions is termed "ectopic". Surgical removal or radiation induced destruction of part or all of the hypersecreting tissue is frequently the treatment of choice. However, these approaches are not always applicable, result in complete loss of hormone production or have to be repeated due to re-growth of the secreting tissue.

A further level of complexity in endocrine hyperfunction disorders arises in a group of conditions termed multiple endocrine neoplasia (MEN) where two or more endocrine glands are involved. The multiple endocrine neoplasia syndromes (MEN1 and MEN2) are familial conditions with an autosomal dominant pattern of inheritance. MEN1 is characterised by the association of parathyroid hyperplasia, pancreatic endocrine tumours, and pituitary adenomas, and has a prevalence of about 1 in 10000. MEN2 is the association of medullary cell carcinoma of the thyroid and phaeochromocytoma, though parathyroid hyperplasia may also occur in some sufferers.

Most of the morbidity associated with MEN1 is due to the effects of pancreatic endocrine tumours. Often surgery is not possible and the therapeutic aim is to reduce hormone excess. Aside from reducing tumour bulk, which is often precluded, inhibition of hormone secretion is the preferred course of action. Current procedures include subcutaneous application of the somatostatin analogue, octreotide. However, this approach is only temporarily effective, and the success diminishes over a period of months.

Many further disease states are known that involve secretion from other non-endocrine, non-neuronal cells. It would accordingly be desirable to treat, reduce or prevent secretion by non-neuronal cells, such as hyperfunction of the endocrine cells that causes or leads to these disease conditions.

The activity of the botulinum neurotoxins is exclusively restricted to inhibition of neurotransmitter release from neurons. This is due to the exclusive expression of high affinity binding sites for clostridial neurotoxins on neuronal cells [see Daniels-Holgate, P. U. and Dolly, J. O. (1996) Productive and non-productive binding of botulinum neurotoxin to motor nerve endings are distinguished by its heavy chain. J. Neurosci. Res. 44, 263-271].

Non-neuronal cells do not possess the high affinity binding sites for clostridial neurotoxins, and are therefore refractory to the inhibitory effects of exogenously applied neurotoxin. Simple application of clostridial neurotoxins to the surface of non-neuronal cells does not therefore lead to inhibition of secretory vesicle exocytosis.

The productive binding or lack of productive binding of clostridial neurotoxins thereby defines neuronal and non-neuronal cells respectively.

In addition to lacking high affinity binding sites for clostridial neurotoxins, absence of the correct internalisation and intracellular routing mechanism, or additional factors that are not yet understood, would prevent clostridial neurotoxin action in non-neuronal cells.

It is known from WO96/33273 that hybrid clostridial neurotoxins endopeptidases can be prepared and that these hybrids effectively inhibit release of neurotransmitters from neuronal cells to which they are targeted, such as pain transmitting neurons. WO96/33273 describes the activity of hybrids only in neuronal systems where neuronal mechanisms of internalisation and vesicular routing are operational.

Non-neuronal cells are, however, refractory to the effects of clostridial neurotoxins, since simple application of clostridial neurotoxins to the surface of non-neuronal cells does not lead to inhibition of secretory vesicle exocytosis. This insensitivity of non-neuronal cells to clostridial neurotoxins may be due to absence of the requisite receptor, absence of the correct internalisation & intracellular routing mechanism, or additional factors that are not yet understood.

WO95/17904 describes the use of *C. botulinum* holotoxin in the treatment of various disorders such as excessive sweating, lacrimation and mucus secretion, and pain. WO95/17904 describes treatment by targeting neuronal cells It is an object of the present invention to provide methods and compositions for inhibition of secretion from non-neuronal cells.

Accordingly, the present invention is based upon the use of a composition which inhibits the exocytotic machinery in neuronal cells and which surprisingly has been found to be effective at inhibiting exocytotic processes in non-neuronal cells.

A first aspect of the invention thus provides a method of inhibiting secretion from a non-neuronal cell comprising administering an agent comprising at least first and second domains, wherein the first domain cleaves one or more proteins essential to exocytosis and the second domain translocates the first domain into the cell.

Advantageously, the invention provides for inhibition of non-neuronal secretion and enables treatment of disease caused, exacerbated or maintained by such secretion.

An agent for use in the invention is suitably prepared by replacement of the cell-binding $H_C$ domain of a clostridial neurotoxin with a ligand capable of binding to the surface of non-neuronal cells. Surprisingly, this agent is capable of inhibiting the exocytosis of a variety of secreted substances from non-neuronal cells. By covalently linking a clostridial neurotoxin, or a hybrid of two clostridial neurotoxins, in which the $H_C$ region of the H-chain has been removed or modified, to a new molecule or moiety, the Targeting Moiety (TM), an agent is produced that binds to a binding site (BS) on the surface of the relevant non-neuronal secretory cells. A further surprising aspect of the present invention is that if the L-chain of a clostridial neurotoxin, or a fragment, variant or derivative of the L-chain containing the endopeptidase activity, is covalently linked to a TM which can also effect internalisation of the L-chain, or a fragment of the endopeptidase activity, into the cytoplasm of a non-neuronal secretory cell, this also produces an agent capable of inhibiting secretion.

Thus, the present invention overcomes the insusceptibility of non-neuronal cells to the inhibitory effects of clostridial neurotoxins.

An example of an agent of the invention is a polypeptide comprising first and second domains, wherein said first domain cleaves one or more vesicle or plasma-membrane associated proteins essential to neuronal exocytosis and wherein said second domain translocates the polypeptide into the cell or translocates at least that portion responsible for the inhibition of exocytosis into the non-neuronal cell. The polypeptide can be derived from a neurotoxin in which case the polypeptide is typically free of clostridial neurotoxin and free of any clostridial neurotoxin precursor that can be converted into toxin by proteolytic action, being accordingly substantially non-toxic and suitable for therapeutic use. Accordingly, the invention may thus use polypeptides containing a domain equivalent to a clostridial toxin light chain and a domain providing the translocation function of the $H_N$ of a clostridial toxin heavy chain, whilst lacking the functional aspects of a clostridial toxin $H_C$ domain.

In use of the invention, the polypeptide is administered in vivo to a patient, the first domain is translocated into a non-neuronal cell by action of the second domain and cleaves one or more vesicle or plasma-membrane associated proteins essential to the specific cellular process of exocytosis, and cleavage of these proteins results in inhibition of exocytosis, thereby resulting in inhibition of secretion, typically in a non-cytotoxic manner.

The polypeptide of the invention may be obtained by expression of a recombinant nucleic acid, preferably a DNA, and can be a single polypeptide, that is to say not cleaved into separate light and heavy chain domains or two polypeptides linked for example by a disulphide bond.

The first domain preferably comprises a clostridial toxin light chain or a functional fragment or variant of a clostridial toxin light chain. The fragment is optionally an N-terminal, or C-terminal fragment of the light chain, or is an internal fragment, so long as it substantially retains the ability to cleave the vesicle or plasma-membrane associated protein essential to exocytosis. The minimal domains necessary for the activity of the light chain of clostridial toxins are described in J. Biol. Chem., Vol. 267, No. 21, July 1992, pages 14721-14729. The variant has a different peptide sequence from the light chain or from the fragment, though it too is capable of cleaving the vesicle or plasma-membrane associated protein. It is conveniently obtained by insertion, deletion and/or substitution of a light chain or fragment thereof. A variety of variants are possible, including (i) an N-terminal extension to a clostridial toxin light chain or fragment (ii) a clostridial toxin light chain or fragment modified by alteration of at least one amino acid (iii) a C-terminal extension to a clostridial toxin light chain or fragment, or (iv) combinations of 2 or more of (i)-(iii). In further embodiments of the invention, the variant contains an amino acid sequence modified so that (a) there is no protease sensitive region between the LC and $H_N$ components of the polypeptide, or (b) the protease sensitive region is specific for a particular protease. This latter embodiment is of use if it is desired to activate the endopeptidase activity of the light chain in a particular environment or cell, though, in general, the polypeptides of the invention are in an active form prior to administration.

The first domain preferably exhibits endopeptidase activity specific for a substrate selected from one or more of SNAP-25, synaptobrevin/VAMP and syntaxin. The clostridial toxin from which this domain can be obtained or derived is preferably botulinum toxin or tetanus toxin. The polypeptide can further comprise a light chain or fragment or variant of one toxin type and a heavy chain or fragment or variant of another toxin type.

The second domain preferably comprises a clostridial toxin heavy chain $H_N$ portion or a fragment or variant of a clostridial toxin heavy chain $H_N$ portion. The fragment is optionally an N-terminal or C-terminal or internal fragment, so long as it retains the function of the $H_N$ domain. Teachings of regions within the $H_N$ responsible for its function are provided for example in Biochemistry 1995, 34, pages 15175-15181 and Eur. J. Biochem, 1989, 185, pages 197-203. The variant has a different sequence from the $H_N$ domain or fragment, though it too retains the function of the $H_N$ domain. It is conveniently obtained by insertion, deletion and/or substitution of a $H_N$ domain or fragment thereof, and examples of variants include (i) an N-terminal extension to a $H_N$ domain or fragment, (ii) a C-terminal extension to a $H_N$ domain or fragment, (iii) a modification to a $H_N$ domain or fragment by alteration of at least one amino acid, or (iv) combinations of 2 or more of (i)-(iii). The clostridial toxin is preferably botulinum toxin or tetanus toxin.

In preparation of the polypeptides by recombinant means, methods employing fusion proteins can be employed, for example a fusion protein comprising a fusion of (a) a polypeptide of the invention as described above with (b) a second polypeptide adapted for binding to a chromatography matrix so as to enable purification of the fusion protein using said chromatography matrix. It is convenient for the second polypeptide to be adapted to bind to an affinity matrix, such as glutathione Sepharose, enabling rapid separation and purification of the fusion protein from an impure source, such as a cell extract or supernatant.

One second purification polypeptide is glutathione-S-transferase (GST), and others may be chosen so as to enable purification on a chromatography column according to conventional techniques.

In a second aspect of the invention there is provided a method of inhibiting secretion from selected non-neuronal cells responsible for regulated secretion by administering an agent of the invention.

In a third aspect of the invention there is provided a method of treatment of disease resulting, or caused or maintained by secretions from non-neuronal cells, comprising administering an agent of the invention.

In further aspects of the invention there are provided agents of the invention targeted to non-neuronal cells responsible for secretion.

In one embodiment of the invention, an agent is provided for the treatment of conditions resulting from hyperfunction of endocrine cells, for example endocrine neoplasia.

Accordingly, an agent of the invention is used in the treatment of endocrine hyperfunction, to inhibit secretion of endocrine cell-derived chemical messengers. An advantage of the invention is that effective treatment of endocrine hyperfunction and associated disease states is now provided, offering relief to sufferers where hitherto there was none and no such agent available.

A further advantage of the invention is that agents are made available which, in use, result in the inhibition of or decrease in hypersecretion of multiple hormones from a single endocrine gland. Thus, the multitude of disorders that result from hyperfunction of one gland (eg. the anterior pituitary) will be simultaneously treated by a reduction in the function of the hypersecreting gland.

The agent preferably comprises a ligand or targeting domain which binds to an endocrine cell, and is thus rendered specific for these cell types. Examples of suitable ligands include iodine; thyroid stimulating hormone (TSH); TSH receptor antibodies; antibodies to the islet-specific monosialo-ganglioside GM2-1; insulin, insulin-like growth factor and antibodies to the receptors of both; TSH releasing hormone (protirelin) and antibodies to its receptor; FSH/LH releasing hormone (gonadorelin) and antibodies to its receptor; corticotrophin releasing hormone (CRH) and antibodies to its receptor; and ACTH and antibodies to its receptor. According to the invention, an endocrine targeted agent may thus be suitable for the treatment of a disease selected from: endocrine neoplasia including MEN; thyrotoxicosis and other diseases dependent on hypersecretions from the thyroid; acromegaly, hyperprolactinaemia, Cushings disease and other diseases dependent on anterior pituitary hypersecretion; hyperandrogenism, chronic anovulation and other diseases associated with polycystic ovarian syndrome.

In a further embodiment, an agent of the invention is used for the treatment of conditions resulting from secretions of inflammatory cells, for example allergies. Ligands suitable to target agent to these cells include (i) for mast cells, complement receptors in general, including C4 domain of the Fc IgE, and antibodies/ligands to the C3a/C4a-R complement receptor; (ii) for eosinophils, antibodies/ligands to the C3a/C4a-R complement receptor, anti VLA-4 monoclonal antibody, anti-IL5 receptor, antigens or antibodies reactive toward CR4 complement receptor; (iii) for macrophages and monocytes, macrophage stimulating factor, (iv) for macrophages, monocytes and neutrophils, bacterial LPS and yeast B-glucans which bind to CR3, (v) for neutrophils, antibody to OX42, an antigen associated with the iC3b complement receptor, or IL8; (vi) for fibroblasts, mannose 6-phosphate/insulin-like growth factor-beta (M6P/IGF-II) receptor and PA2.26, antibody to a cell-surface receptor for active fibroblasts in mice.

According to a preferred embodiment of the present invention, the TM is a growth factor, preferably an epidermal growth factor (EGF), vascular endothelial growth factor, platelet-derived growth factor, keratinocyte growth factor, hepatocyte growth factor, transforming growth factor alpha, transforming growth factor beta.

According to another preferred embodiment of the present invention, the TM is a peptide or protein that binds to an inflammatory cell. A preferred example of such a TM is an integrin-binding protein.

Integrins are obligate heterodimer transmembrane proteins containing two distinct chains α (alpha) and β (beta) subunits. In mammals, 19 alpha and 8 beta subunits have been characterised—see Humphries, M. J. (2000), Integrin structure. Biochem Soc Trans. 28: 311-339, which is herein incorporated by reference thereto. Integrin subunits span through the plasma membrane, and in general have very short cytoplasmic domains of about 40-70 amino acids. Outside the cell plasma membrane, the alpha and beta chains lie close together along a length of about 23 nm, the final 5 nm $NH_2$-termini of each chain forming a ligand-binding region to which an agent of the present invention binds.

Preferred integrin-binding proteins of the present invention comprise the amino sequence Arg-Gly-Asp ("RGD"), which binds to the above-described ligand-binding region—see Craig. D et al. (2004), Structural insights into how the MIDAS ion stabilizes integrin binding to an RGD peptide under force. Structure, vol. 12, pp 2049-2058, which is herein incorporated by reference thereto.

In one embodiment, the integrin-binding protein TMs of the present invention have an amino acid length of between 3 and 100, preferably between 3 and 50, more preferably between 5 and 25, and particularly preferably between 5 and 15 amino acid residues.

The TMs of the present invention may form linear or cyclic structures. Preferred integrin-binding TMs of the present invention include actin, alpha-actinin, focal contact adhesion kinase, paxillin, talin, RACK1, collagen, laminin, fibrinogen, heparin, phytohaemagglutinin, fibronectin, vitronectin, VCAM-1, ICAM-1, ICAM-2 and serum protein. Many integrins recognise the triple Arg-Gly-Asp (RGD) peptide sequence (Ruoslahti, 1996). The RGD motif is found in over 100 proteins including fibronectin, tenascin, fibrinogen and vitronectin. The RGD-integrin interaction is exploited as a conserved mechanism of cell entry by many pathogens including coxsackievirus (Roivaninen et al., 1991) and adenovirus (Mathias et al., 1994).

Additionally preferred integrin-binding TMs of the present invention include proteins selected from the following sequences: Arg-Gly-Asp-Phe-Val (SEQ ID NO:23); Arg-Gly-Asp-{D-Phe}-{N-methyl-Val} (SEQ ID NO:23); RGDFV (SEQ ID NO:23); RGDfNMeV (SEQ ID NO:23); GGRGDMFGA (SEQ ID NO:21); GGCRGDMFGCA (SEQ ID NO:22); GRGDSP (SEQ ID NO:26); GRGESP (SEQ ID NO:27); PLAEIDGIEL (SEQ ID NO:24 and CPLAEIDG-IELC (SEQ ID NO:25). Reference to the above sequences embraces linear and cyclic forms, together with peptides exhibiting at least 80%, 85%, 90%, 95%, 98%, 99% sequence identity with said sequences. All of said TMs preferably retain the "RGD" tri-peptide sequence.

Diseases thus treatable according to the invention include diseases selected from allergies (seasonal allergic rhinitis (hay fever), allergic conjunctivitis, vasomotor rhinitis and food allergy), eosinophilia, asthma, rheumatoid arthritis, systemic lupus erythematosus, discoid lupus erythematosus, ulcerative colitis, Crohn's disease, haemorrhoids, pruritus, glomerulonephritis, hepatitis, pancreatitis, gastritis, vasculitis, myocarditis, psoriasis, eczema, chronic radiation-induced fibrosis, lung scarring and other fibrotic disorders.

VAMP expression has been demonstrated in B-lymphocytes [see Olken, S. K. and Corley, R. B. 1998, Mol. Biol. Cell. 9, 207a]. Thus, an agent according to the present invention, when targeted to a B-lymphocyte and following internalisation and retrograde transport, may exert its inhibitory effect on such target cells.

In a further embodiment, an agent of the invention is provided for the treatment of conditions resulting from secretions of the exocrine cells, for example acute pancreatitis (Hansen et al, 1999, J. Biol. Chem. 274, 22871-22876). Ligands suitable to target agent to these cells include pituitary adenyl cyclase activating peptide (PACAP-38) or an antibody to its receptor. The present invention also concerns treatment of mucus hypersecretion from mucus-secreting cells located in the alimentary tract, in particular located in the colon.

Gaisano, H. Y. et al. (1994) J. Biol. Chem. 269, pp. 17062-17066 has demonstrated that, following in vitro membrane permeabilisation to permit cellular entry, tetanus toxin light chain cleaves a vesicle-associated membrane protein (VAMP) isoform 2 in rat pancreatic zymogen granules, and inhibits enzyme secretion. Thus, an agent according to the present invention, when targeted to a pancreatic cell and following internalisation and retrograde transport, may exert its inhibitory effect on such target cells.

In a further embodiment, an agent of the invention is used for the treatment of conditions resulting from secretions of immunological cells, for example autoimmune disorders where B lymphocytes are to be targeted (immunosuppression). Ligands suitable to target agent to these cells include Epstein Barr virus fragment/surface feature or idiotypic antibody (binds to CR2 receptor on B-lymphocytes and lymph node follicular dendritic cells). Diseases treatable include myasthenia gravis, rheumatoid arthritis, systemic lupus erythematosus, discoid lupus erythematosus, organ transplant, tissue transplant, fluid transplant, Graves disease, thyrotoxicosis, autoimmune diabetes, haemolytic anaemia, thrombocytopenic purpura, neutropenia, chronic autoimmune hepatitis, autoimmune gastritis, pernicious anaemia, Hashimoto's thyroiditis, Addison's disease, Sjogren's syndrome, primary biliary cirrhosis, polymyositis, scleroderma, systemic sclerosis, pemphigus vulgaris, bullous pemphigoid, myocarditis, rheumatic carditis, glomerulonephritis (Goodpasture type), uveitis, orchitis, ulcerative colitis, vasculitis, atrophic gastritis, pernicious anaemia, type 1 diabetes mellitus.

By using cell permeabilisation techniques it has been possible to internalise BoNT/C into eosinophils [see Pinxteren J A, et al (2000) Biochimie, April; 82(4):385-93 Thirty years of stimulus-secretion coupling: from $Ca(2^+)$ to GTP in the regulation of exocytosis]. Following internalisation, BoNT/C exerted an inhibitory effect on exocytosis in eosinophils. Thus, an agent according to the present invention, when targeted to an eosinophil and following internalisation and retrograde transport, may exert its inhibitory effect on such target cells.

In a further embodiment of the invention, an agent is provided for the treatment of conditions resulting from secretions of cells of the cardiovascular system. Suitable ligands for targeting platelets for the treatment of disease states involving inappropriate platelet activation and thrombus formation include thrombin and TRAP (thrombin receptor agonist peptide) or antibodies to CD31/PECAM-1, CD24 or CD106/VCAM-1, and ligands for targeting cardiovascular endothelial cells for the treatment of hypertension include GP1b surface antigen recognising antibodies.

In a further embodiment of the invention, an agent is provided for the treatment of bone disorders. Suitable ligands for targeting osteoblasts for the treatment of a disease selected from osteopetrosis and osteoporosis include calcitonin, and for targeting an agent to osteoclasts include osteoclast differentiation factors (eg. TRANCE, or RANKL or OPGL), and an antibody to the receptor RANK.

In use of the invention, a Targeting moiety (TM) provides specificity for the BS on the relevant non-neuronal secretory cells. The TM component of the agent can comprise one of many cell binding molecules, including, but not limited to, antibodies, monoclonal antibodies, antibody fragments (Fab, F(ab)'$_2$, Fv, ScFv, etc.), lectins, hormones, cytokines, growth factors, peptides, carbohydrates, lipids, glycons, nucleic acids or complement components.

The TM is selected in accordance with the desired cell-type to which the agent of the present invention is to be targeted, and preferably has a high specificity and/or affinity for non-neuronal target cells. Preferably, the TM does not substantially bind to neuronal cells of the presynaptic muscular junction, and thus the agent is substantially non-toxic in that it is not capable of effecting muscular paralysis. This is in contrast to clostridial holotoxin which targets the presynaptic muscular junction and effects muscular paralysis. In addition, preferably the TM does not substantially bind to neuronal peripheral sensory cells, and thus the agent does not exert any substantial analgesic effect. Preferably, the TM does not substantially bind to neuronal cells, and does not therefore permit the agent to exert an inhibitory effect on secretion in a neuronal cell.

It is known in the art that the $H_C$ portion of the neurotoxin molecule can be removed from the other portion of the H-chain, known as $H_N$, such that the $H_N$ fragment remains disulphide linked to the L-chain of the neurotoxin providing a fragment known as $LH_N$. Thus, in one embodiment of the present invention the $LH_N$ fragment of a clostridial neurotoxin is covalently linked, using linkages which may include one or more spacer regions, to a TM.

In another embodiment of the invention, the $H_C$ domain of a clostridial neurotoxin is mutated, blocked or modified, e.g. by chemical modification, to reduce or preferably incapacitate its ability to bind the neurotoxin to receptors at the neuromuscular junction. This modified clostridial neurotoxin is then covalently linked, using linkages which may include one or more spacer regions, to a TM.

In another embodiment of the invention, the heavy chain of a clostridial neurotoxin, in which the $H_C$ domain is mutated, blocked or modified, e.g. by chemical modification, to reduce or preferably incapacitate its ability to bind the neurotoxin to receptors at the neuromuscular junction, is combined with the L-chain of a different clostridial neurotoxin. This hybrid, modified clostridial neurotoxin is then covalently linked, using linkages which may include one or more spacer regions, to a TM.

In another embodiment of the invention, the $H_N$ domain of a clostridial neurotoxin is combined with the L-chain of a different clostridial neurotoxin. This hybrid $LH_N$ is then covalently linked, using linkages which may include one or more spacer regions, to a TM.

In another embodiment of the invention, the light chain of a clostridial neurotoxin, or a fragment of the light chain containing the endopeptidase activity, is covalently linked, using linkages which may include one or more spacer regions, to a TM which can also effect the internalisation of the L-chain, or a fragment of the L-chain containing the endopeptidase activity, into the cytoplasm of the relevant non-neuronal cells responsible for secretion.

In another embodiment of the invention, the light chain of a clostridial neurotoxin, or a fragment of the light chain containing the endopeptidase activity, is covalently linked, using linkages which may include one or more spacer regions, to a translocation domain to effect transport of the endopeptidase fragment into the cytosol. Examples of translocation domains derived from bacterial neurotoxins are as follows:

Botulinum type A neurotoxin—amino acid residues (449-871)

Botulinum type B neurotoxin—amino acid residues (441-858)

Botulinum type C neurotoxin—amino acid residues (442-866)

Botulinum type D neurotoxin—amino acid residues (446-862)

Botulinum type E neurotoxin—amino acid residues (423-845)

Botulinum type F neurotoxin—amino acid residues (440-864)

Botulinum type G neurotoxin—amino acid residues (442-863)

Tetanus neurotoxin—amino acid residues (458-879)

other clostridial sources include *C. butyricum*, and *C. argentinense*.

[for the genetic basis of toxin production in *Clostridium botulinum* and *C. tetani*, see Henderson et al (1997) in The Clostridia: Molecular Biology and Pathogenesis, Academic press].

In addition to the above translocation domains derived from clostridial sources, other non-clostridial sources may be employed in an agent according to the present invention. These include, for example, diphtheria toxin [London, E. (1992) Biochem. Biophys. Acta., 1112, pp. 25-51], Pseudomonas exotoxin A [Prior et al (1992) Biochem., 31, pp. 3555-3559], influenza virus haemagglutinin fusogenic peptides [Wagner et al (1992) PNAS, 89, pp. 7934-7938], and amphiphilic peptides [Murata et al (1992) Biochem., 31, pp. 1986-1992].

In use, the domains of an agent according to the present invention are associated with each other. In one embodiment, two or more of the Domains may be joined together either directly (eg. by a covalent linkage), or via a linker molecule. Conjugation techniques suitable for use in the present invention have been well documented:—Chemistry of protein conjugation and cross-linking Edited by Wong, S. S. 1993, CRC Press Inc., Florida; and Bioconjugate techniques, Edited by Hermanson, G. T. 1996, Academic Press, London, UK.

Direct linkage of two or more of Domains is now described with reference to clostridial neurotoxins and to the present Applicant's nomenclature of clostridial neurotoxin domains, namely Domain B (contains the binding domain), Domain T (contains the translocation domain) and Domain E (contains the protease domain), although no limitation thereto is intended.

In one embodiment of the present invention, Domains E and T may be mixed together in equimolar quantities under reducing conditions and covalently coupled by repeated dialysis (eg. at 4° C., with agitation), into physiological salt solution in the absence of reducing agents. At this stage, in contrast to Example 6 of WO94/21300, the E-T complex is not blocked by iodoacetamide, therefore any remaining free —SH groups are retained.

Domain B is then modified, for example, by derivatisation with SPDP followed by subsequent reduction. In this reaction, SPDP does not remain attached as a spacer molecule to Domain B, but simply increases the efficiency of this reduction reaction.

Reduced domain B and the E-T complex may then be mixed under non-reducing conditions (eg. at 4° C.) to form a disulphide-linked E-T-B "agent".

In another embodiment, a coupled E-T complex may be prepared according to Example 6 of WO94/21300, including the addition of iodoacetamide to block free sulphydryl groups. However, the E-T complex is not further derivatised, and the remaining chemistry makes use of the free amino (—NH$_2$) groups on amino acid side chains (eg. lysine, and arginine amino acids).

Domain B may be derivatised using carbodiimide chemistry (eg. using EDC) to activate carboxyl groups on amino acid side chains (eg. glutamate, and aspartate amino acids), and the E-T complex mixed with the derivatised Domain B to result in a covalently coupled (amide bond) E-T-B complex.

Suitable methodology for the creation of such an agent is, for example, as follows:

Domain B was dialysed into MES buffer (0.1 M MES, 0.1 M sodium chloride, pH 5.0) to a final concentration of 0.5 mg/ml. EDAC (1-ethyl-3-[3-dimethylaminopropyl]carbodiimide hydrochloride) was added to final concentrations of 0.2 mg/ml and reacted for 30 min at room temperature. Excess EDAC was removed by desalting over a MES buffer equilibrated PD-10 column (Pharmacia). The derivatised domain B was concentrated (to >2 mg/ml) using Millipore Biomax 10 concentrators. The E-T complex (1 mg/ml) was mixed for 16 hours at 4° C., and the E-T-B complex purified by size-exclusion chromatography over a Superose 12 HR10/30 column (Pharmacia) to remove unreacted Domain B (column buffer: 50 mM sodium phosphate pH6.5+20 mM NaCl).

As an alternative to direct covalent linkage of the various Domains of an agent according to the present invention, suitable spacer molecules may be employed. The term linker molecule is used synonymously with spacer molecule. Spacer technology was readily available prior to the present application.

For example, one particular coupling agent (SPDP) is described in Example 6 of WO94/21300 (see lines 3-5 on page 16). In Example 6, SPDP is linked to an E-T complex, thereby providing an E-T complex including a linker molecule. This complex is then reacted a Domain B, which becomes attached to the E-T complex via the linker molecule. In this method, SPDP results in a spacing region of approximately 6.8 Angstroms between different Domains of the "agent" of the present invention.

A variant of SPDP known as LC-SPDP is identical in all respects to SPDP but for an increased chain length. LC-SPDP may be used to covalently link two Domains of the "agent" of the present invention resulting in a 15.6 Angstrom spacing between these Domains.

Examples of spacer molecules include, but are not limited to:—

(GGGGS)$_2$ (SEQ ID NO:28), elbow regions of Fab—[see Anand et al., (1991) J. Biol. Chem. 266, 21874-9];

(GGGGS)$_3$ (SEQ ID NO:28)—[see Brinkmann et al. (1991) Proc. Natl. Acad. Sci. 88, 8616-20];

the interdomain linker of cellulose—[see Takkinen et al. (1991) Protein Eng, 4, 837-841];

PPPIEGR (SEQ ID NO:29)—[see Kim (1993) Protein Science, 2, 348-356];

Collagen-like spacer—[see Rock (1992) Protein Engineering, vol 5, No 6, pp 583-591];

and Trypsin-sensitive diphtheria toxin peptide—[see O'Hare (1990) FEBS, vol 273, No 1,2, pp 200-204].

In a further embodiment of the present invention, an agent having the structure E-X-T-X-B, where "X" is a spacer molecule between each domain, may be prepared, for example, as follows:

Domain E is derivatised with SPDP, but not subsequently reduced. This results in an SPDP-derivatised Domain E.

Domain T is similarly prepared, but subsequently reduced with 10 mM dithiothreitol (DTT). The 10 mM DTT present in the Domain T preparation, following elution from the QAE column (see Example 6 in WO94/21300), is removed by passage of Domain T through a sephadex G-25 column equilibrated in PBS.

Domain T free of reducing agent is then mixed with the SPDP-derivatised Domain E, with agitation at 4° C. for 16 hours. E-T complex is isolated from free Domain E and from free Domain T by size-exclusion chromatography (Sephadex G-150). Whereafter, the same procedure can be followed as described in Example 6 of WO94/21300 for rederivatisation of the E-T complex with SPDP, and subsequent coupling thereof to the free sulphydryl on Domain B.

The agents according to the present invention may be prepared recombinantly. In one embodiment, the preparation of a recombinant agent may involve arrangement of the coding sequences of the selected TM and clostridial neurotoxin component in a single genetic construct. These coding sequences may be arranged in-frame so that subsequent transcription and translation is continuous through both coding sequences and results in a fusion protein. All constructs would have a 5' ATG codon to encode an N-terminal methionine, and a C-terminal translational stop codon.

Thus, a the light chain of a clostridial neurotoxin (or a fragment of the light chain containing the endopeptidase activity) may be expressed recombinantly as a fusion protein with a TM which can also effect the internalisation of the L-chain (or a fragment thereof) into the cytoplasm of the relevant non-neuronal cells responsible for secretion. The expressed fusion protein may also include one or more spacer regions.

In the case of an agent based on clostridial neurotoxin, the following information would be required to produce said agent recombinantly:—(i) DNA sequence data relating to a selected TM; (ii) DNA sequence data relating to the clostridial neurotoxin component; and (iii) a protocol to permit construction and expression of the construct comprising (i) and (ii).

All of the above basic information (i)-(iii) are either readily available, or are readily determinable by conventional methods. For example, both WO98/07864 and WO99/17806 exemplify clostridial neurotoxin recombinant technology suitable for use in the present application.

In addition, methods for the construction and expression of the constructs of the present invention may employ information from the following references and others:—Lorberboum-Galski, H., FitzGerald, D., Chaudhary, V., Adhya, S., Pastan, I. (1988). Cytotoxic activity of an interleukin 2-Pseudomonas exotoxin chimeric protein produced in *Escherichia coli*. Proc Natl Acad Sci USA 85(6):1922-6; Murphy, J. R. (1988) Diphtheria-related peptide hormone gene fusions: a molecular genetic approach to chimeric toxin development. Cancer Treat Res; 37:123-40; Williams, D. P., Parker, K., Bacha, P., Bishai, W., Borowski, M., Genbauffe, F., Strom, T. B., Murphy, J. R. (1987). Diphtheria toxin receptor binding domain substitution with interleukin-2: genetic construction and properties of a diphtheria toxin-related interleukin-2 fusion protein. Protein Eng; 1(6):493-8; Arora, N., Williamson, L. C., Leppla, S. H., Halpern, J. L. (1994). Cytotoxic effects of a chimeric protein consisting of tetanus toxin light chain and anthrax toxin lethal factor in non-neuronal cells J Biol Chem, 269(42):26165-71; Brinkmann, U., Reiter, Y., Jung, S. H., Lee, B., Pastan, I. (1993). A recombinant immunotoxin containing a disulphide-stabilized Fv fragment. Proc Natl Acad Sci USA; 90(16):7538-42; and O'Hare, M., Brown, A. N., Hussain, K., Gebhardt, A., Watson, G., Roberts, L. M., Vitetta, E. S., Thorpe, P. E., Lord, J. M. (1990). Cytotoxicity of a recombinant ricin-A-chain fusion protein containing a proteolytically-cleavable spacer sequence. FEBS Lett October 29; 273(1-2):200-4.

Suitable clostridial neurotoxin sequence information relating to L- and LH$_N$-chains may be obtained from, for example, Kurazono, H. (1992) J. Biol. Chem., vol. 267, No. 21, pp. 14721-14729; and Popoff, M. R., and Marvaud, J.-C. (1999) The Comprehensive Sourcebook of Bacterial Protein Toxins, 2nd edition (ed. Alouf, J. E., and Freer, J. H.), Academic Press, pp. 174-201.

Similarly, suitable TM sequence data are widely available in the art. Alternatively, any necessary sequence data may be obtained by techniques which were well-known to the skilled person.

For example, DNA encoding the TM component may be cloned from a source organism by screening a cDNA library for the correct coding region (for example by using specific oligonucleotides based on the known sequence information to probe the library), isolating the TM DNA, sequencing this DNA for confirmation purposes, and then placing the isolated DNA in an appropriate expression vector for expression in the chosen host.

As an alternative to isolation of the sequence from a library, the available sequence information may be employed to prepare specific primers for use in PCR, whereby the coding sequence is then amplified directly from the source material and, by suitable use of primers, may be cloned directly into an expression vector.

Another alternative method for isolation of the coding sequence is to use the existing sequence information and synthesise a copy, possibly incorporating alterations, using DNA synthesis technology. For example, DNA sequence data may be generated from existing protein and/or RNA sequence information. Using DNA synthesis technology to do this (and the alternative described above) enables the codon bias of the coding sequence to be modified to be optimal for the chosen expression host. This may give rise to superior expression levels of the fusion protein.

Optimisation of the codon bias for the expression host may be applied to the DNA sequences encoding the TM and clostridial components of the construct. Optimisation of the codon bias is possible by application of the protein sequence into freely available DNA/protein database software, eg. programs available from Genetics Computer Group, Inc.

According to a further aspect of the present invention, nucleic acid encoding the light chain of a clostridial neurotoxin (or a fragment of the light chain containing the endopeptidase activity), may be associated with a TM which can also effect the internalisation of the nucleic acid encoding the L-chain (or a fragment thereof) into the cytoplasm of the relevant non-neuronal cells responsible for secretion. The nucleic acid sequence may be coupled to a translocation domain, and optionally to a targeting moiety, by for example direct covalent linkage or via spacer molecule technology. Ideally, the coding sequence will be expressed in the target cell.

Thus, the agent of the present invention may be the expression product of a recombinant gene delivered independently to the preferred site of action of the agent. Gene delivery technologies are widely reported in the literature [reviewed in "Advanced Drug Delivery Reviews" Vol. 27, (1997), Elsevier Science Ireland Ltd].

According to another aspect, the present invention therefore provides a method of treating a condition or disease which is susceptible of treatment with a nucleic acid in a mammal eg. a human which comprises administering to the sufferer an effective, non-toxic amount of a compound of the invention. A condition or disease which is susceptible of treatment with a nucleic acid may be for example a condition or disease which may be treated by or requiring gene therapy. The preferred conditions or diseases susceptible to treatment according to the present invention, together with the preferred TMs, have been described previously in this specification. Similarly, the preferred first domains which cleave one or more proteins (eg. SNAP-25, synaptobrevin and syntaxin) essential to exocytosis have been described previously in this specification. The various domains of an agent for use in gene therapy may be directly linked (eg. via a covalent bond) or indirectly linked (eg. via a spacer molecule), as for example previously described in this specification.

The invention further provides a compound of the invention for use as an active therapeutic substance, in particular for use in treating a condition or disease as set forth in the present claims.

The invention further provides pharmaceutical compositions comprising an agent or a conjugate of the invention and a pharmaceutically acceptable carrier.

In use the agent or conjugate will normally be employed in the form of a pharmaceutical composition in association with a human pharmaceutical carrier, diluent and/or excipient, although the exact form of the composition will depend on the mode of administration.

The conjugate may, for example, be employed in the form of an aerosol or nebulisable solution for inhalation or a sterile solution for parenteral administration, intra-articular administration or intra-cranial administration.

For treating endocrine targets, i.v. injection, direct injection into gland, or aerosolisation for lung delivery are preferred; for treating inflammatory cell targets, i.v. injection, sub-cutaneous injection, or surface patch administration are preferred; for treating exocrine targets, i.v. injection, or direct injection into the gland are preferred; for treating immunological targets, i.v. injection, or injection into specific tissues e.g thymus, bone marrow, or lymph tissue are preferred; for treatment of cardiovascular targets, i.v. injection is preferred; and for treatment of bone targets, i.v. injection, or direct injection is preferred. In cases of i.v. injection, this should also include the use of pump systems.

The dosage ranges for administration of the compounds of the present invention are those to produce the desired therapeutic effect. It will be appreciated that the dosage range required depends on the precise nature of the conjugate, the route of administration, the nature of the formulation, the age of the patient, the nature, extent or severity of the patient's condition, contraindications, if any, and the judgement of the attending physician.

Suitable daily dosages are in the range 0.0001-1 mg/kg, preferably 0.0001-0.5 mg/kg, more preferably 0.002-0.5 mg/kg, and particularly preferably 0.004-0.5 mg/kg. The unit dosage can vary from less that 1 microgram to 30 mg, but typically will be in the region of 0.01 to 1 mg per dose, which may be administered daily or less frequently, such as weekly or six monthly.

Wide variations in the required dosage, however, are to be expected depending on the precise nature of the conjugate, and the differing efficiencies of various routes of administration. For example, oral administration would be expected to require higher dosages than administration by intravenous injection.

Variations in these dosage levels can be adjusted using standard empirical routines for optimisation, as is well understood in the art.

Compositions suitable for injection may be in the form of solutions, suspensions or emulsions, or dry powders which are dissolved or suspended in a suitable vehicle prior to use.

Fluid unit dosage forms are typically prepared utilising a pyrogen-free sterile vehicle. The active ingredients, depending on the vehicle and concentration used, can be either dissolved or suspended in the vehicle.

Solutions may be used for all forms of parenteral administration, and are particularly used for intravenous injection. In preparing solutions the compound can be dissolved in the vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers may be sterilised by autoclaving.

Advantageously additives such as buffering, solubilising, stabilising, preservative or bactericidal, suspending or emulsifying agents and/or local anaesthetic agents may be dissolved in the vehicle.

Dry powders which are dissolved or suspended in a suitable vehicle prior to use may be prepared by filling pre-sterilised drug substance and other ingredients into a sterile container using aseptic technique in a sterile area.

Alternatively the agent and other ingredients may be dissolved in an aqueous vehicle, the solution is sterilized by filtration and distributed into suitable containers using aseptic technique in a sterile area. The product is then freeze dried and the containers are sealed aseptically.

Parenteral suspensions, suitable for intramuscular, subcutaneous or intradermal injection, are prepared in substantially the same manner, except that the sterile compound is suspended in the sterile vehicle, instead of being dissolved and sterilisation cannot be accomplished by filtration. The compound may be isolated in a sterile state or alternatively it may be sterilised after isolation, e.g. by gamma irradiation.

Advantageously, a suspending agent for example polyvinylpyrrolidone is included in the composition to facilitate uniform distribution of the compound.

Compositions suitable for administration via the respiratory tract include aerosols, nebulisable solutions or microfine powders for insufflation. In the latter case, particle size of less than 50 microns, especially less than 10 microns, is preferred. Such compositions may be made up in a conventional manner and employed in conjunction with conventional administration devices.

The agent described in this invention can be used in vivo, either directly or as a pharmaceutically acceptable salt, for the treatment of conditions involving secretion from non-neuronal cells, such as hypersecretion of endocrine cell derived chemical messengers, hypersecretion from exocrine cells, secretions from the cells of the immune system, the cardiovascular system and from bone cells.

The present invention will now be described by reference to the following examples illustrated by the accompanying drawings in which:

FIG. 2 shows activity of WGA-LH$_N$/A on release of transmitter from HIT-T15 cells;

FIG. 3 shows correlation of SNAP-25 cleavage with inhibition of neurotransmitter release following application of WGA-LH$_N$/A to HIT-T15 cells;

FIG. 7 shows the effect of low pH and BoNT/B treatment on stimulated von Willebrands Factor (vWF) release from human umbilical vein endothelial cells;

FIG. 8 shows release of [$^3$H]-glucosamine labelled high molecular weight material from LS180 cells;

FIG. 9 shows the effect of low pH and BoNT/B treatment on stimulated β-glucuronidase release from differentiated HL60 cells;

FIGS. 5-19 are now described in more detail.

Figure 5:
FIG. 5 shows a Western blot indicating expression of recLH$_N$/B in *E. coli*.

Referring to FIG. 5, MBP-LH$_N$/B was expressed in *E. coli* as described in Example 4. Lane 1 represents the profile of the expressed fusion protein in *E. coli*. Lane 2 represents the profile of fusion protein expression in the crude *E. coli* lysate. Lane 3 represents the profile of the MBP-LH$_N$/B following purification by immobilised amylose. Molecular weights in kDa are indicated to the right side of the Figure.

Figure 6:
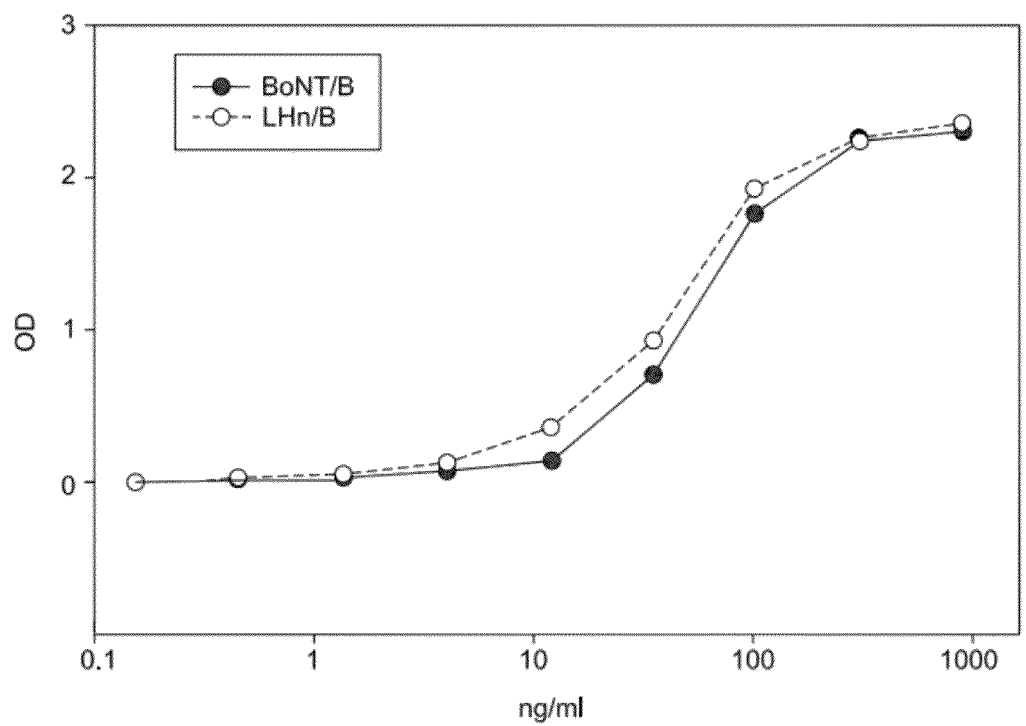
FIG. 6 shows in vitro cleavage of synthetic VAMP peptide by recLH$_N$/B.

Referring to FIG. 6, dilutions of recLH$_N$/B (prepared as described in Example 4) and BoNT/B were compared in an in vitro peptide cleavage assay. Data indicate that the recombinant product has similar catalytic activity to that of the native neurotoxin, indicating that the recombinant product has folded correctly into an active conformation.

Figure 7:
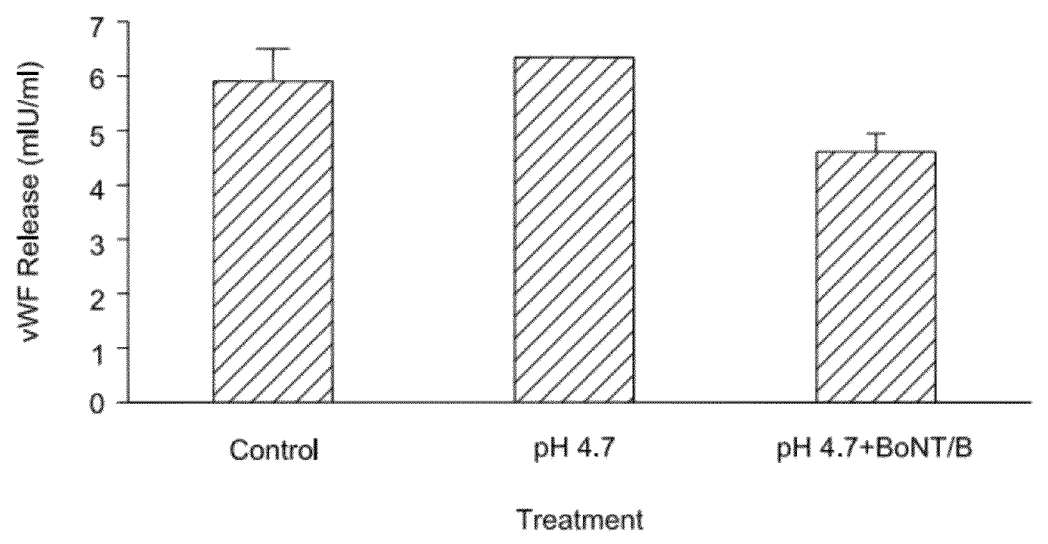

Referring to FIG. 7, cells were exposed to pH 4.7 media with or without 500 nM BoNT/B (control cells received pH7.4 medium) for 2.5 hours then washed. 24 hours later release of vWF was stimulated using 1 mM histamine and the presented results are the net stimulated release with basal subtracted. Results are presented in mIU of vWF/ml and are the mean+/−SEM of three determinations apart from pH 4.7 alone which is two determinations. pH 4.7+BoNT/B has reduced vWF release by 27.4% compared to pH 4.7 controls.

Figure 8:
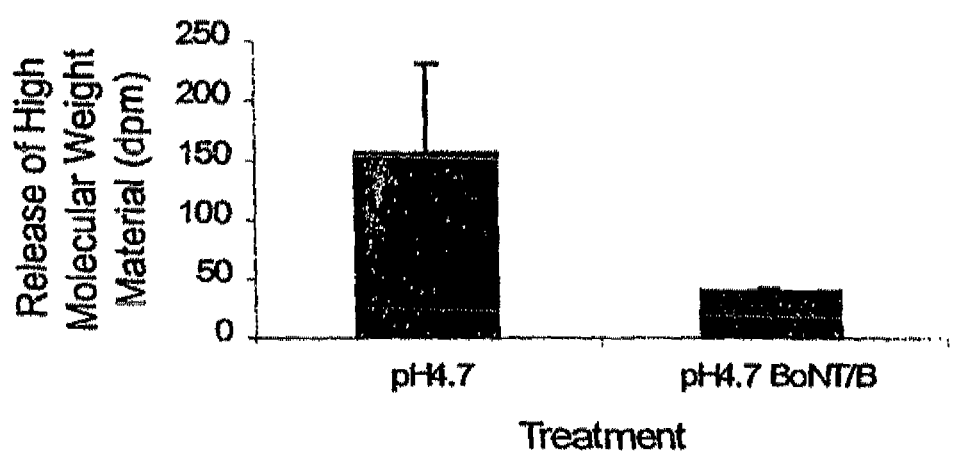

Referring to FIG. 8, high molecular weight mucin synthesising colon carcinoma LS180 cells were treated with pH 4.7 medium and pH 4.7 medium containing 500 nM botulinum neurotoxin type B (BoNT/B) for four hours then labelled with [$^3$H]-glucosamine for 18 hours. Release of high molecular weight material was stimulated with 10 μM ionomycin and [$^3$H]-glucosamine labelled material recovered by ultracentrifugation and centrifugal molecular weight sieving. Radiolabel of release of labelled high molecular weight material was determined by scintillation counting and net stimulated release calculated by subtracting non-stimulated basal values. Data are expressed as disintegrations per minute (dpm)+/−SEM of three determinations. BoNT/B co-treatment clearly inhibits the release of high molecular weight material from these mucin synthesising cells and in this experiment a 74.5% reduction was seen.

Figure 9:
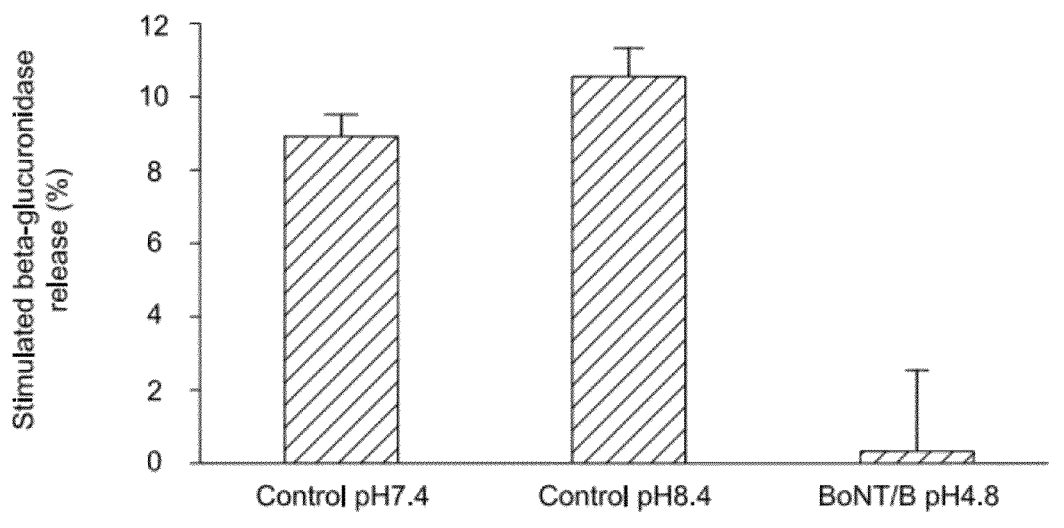

Referring to FIG. 9, cells were exposed to pH 4.8 media with or without 500 nM BoNT/B (control cells received pH 7.4 medium) for 2.5 hours then washed and differentiated for 40 hours by the addition of 300 μM dibutyryl cyclic AMP (dbcAMP). Cells were stimulated with fMet-Leu-Phe (1 μM)+ATP (100 μM) in the presence of cytochalasin B (5 μM) for 10 minutes and released β-glucuronidase determined by colourimetric assay. Net stimulated release was calculated by subtraction of unstimulated basal release values from stimulated values and released activity is expressed as a percentage of the total activity present in the cells. Data are the mean+/−SEM of three determinations. BoNT/B treatment in low pH medium significantly inhibited stimulated release of β-glucuronidase compared to cells treated with low pH alone (p=0.0315 when subjected to a 2 tailed Student T test with groups of unequal variance).

Figure 10:
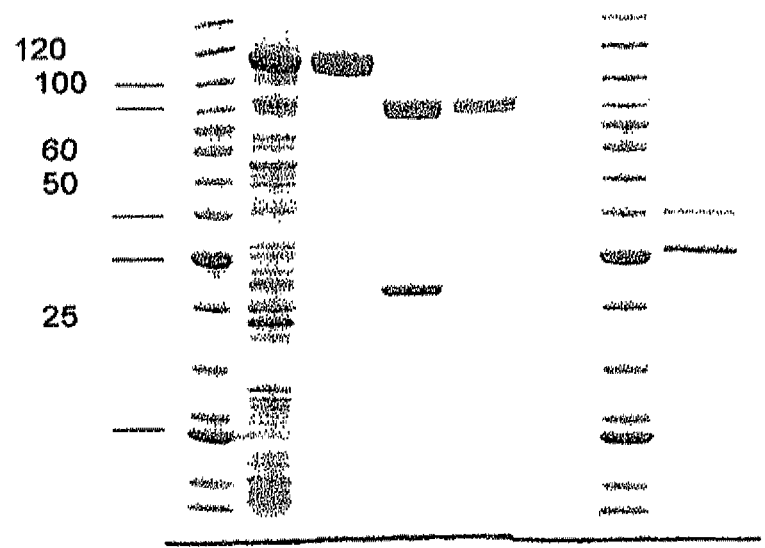
FIG. 10 shows purification of a LH$_N$/C-EGF fusion protein.

Referring to FIG. 10, using the methodology outlined in Example 11, a LH$_N$/C-EGF fusion protein was purified from *E. coli* BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE. Lane 1 & 6: Molecular mass markers (kDa), lane 2: Clarified crude cell lysate, lane 3: First nickel chelating Sepharose column eluant, lane 4: Factor Xa digested protein, lane 5: Purified LH$_N$/C-EGF under non-reducing conditions, lane 7: Purified LH$_N$/C-EGF under reduced conditions.

Figure 11:
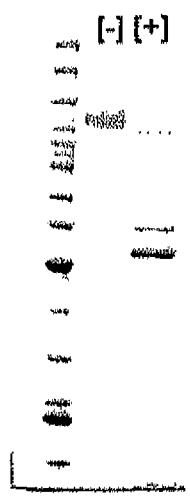
FIG. 11 shows purification of a LH$_N$/B-EGF fusion protein.

Referring to FIG. 11, using the methodology outlined in Example 12, a LH$_N$/B-EGF fusion protein was purified from *E. coli* BL21 cells. Briefly, the soluble products obtained following cell disruption were applied to a nickel-charged affinity capture column. Bound proteins were eluted with 100 mM imidazole, treated with Factor Xa and enterokinase to activate the fusion protein and remove the maltose-binding protein (MBP) tag, then re-applied to a second nickel-charged affinity capture column. Samples from the purification procedure were assessed by SDS-PAGE. The final purified material in the absence and presence of reducing agent is identified in the lanes marked [−] and [+] respectively.

Figure 12:
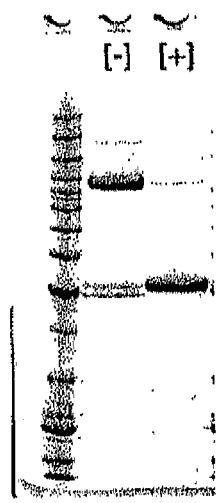
FIG. 12 shows purification of a LH$_N$/C-RGD fusion protein.

Referring to FIG. 12, using the methodology outlined in Example 13, a LH$_N$/C-RGD fusion protein was purified from *E. coli* BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE. The final purified material in the absence and presence of reducing agent is identified in the lanes marked [−] and [+] respectively.

Figure 13:
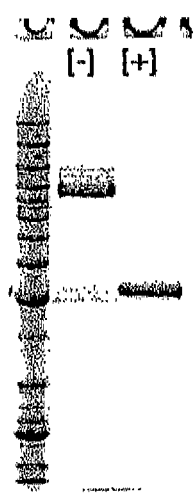
FIG. 13 shows purification of a LH$_N$/C-cyclic RGD fusion protein.

Referring to FIG. 13, using the methodology outlined in Example 14, a LH$_N$/C-cyclic RGD fusion protein was purified from *E. coli* BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE. The final purified material in the absence and presence of reducing agent is identified in the lanes marked [−] and [+] respectively.

Figure 14:
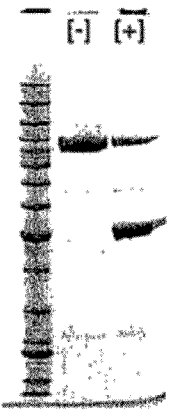
FIG. 14 shows purification of a LC/C-RGD-H$_N$/C fusion protein.

Referring to FIG. 14, using the methodology outlined in Example 15, a LC/C-RGD-H$_N$/C fusion protein was purified from *E. coli* BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE. The final purified material in the absence and presence of reducing agent is identified in the lanes marked [−] and [+] respectively.

Figure 15:
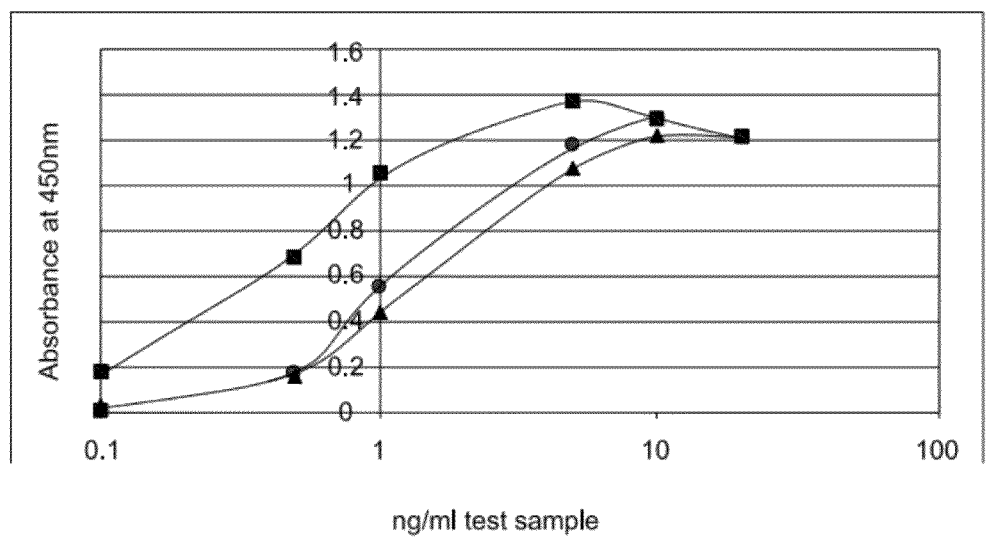
FIG. 15 shows VAMP cleavage activity of LH$_N$/B-EGF.

Referring to FIG. 15, using the methodology outlined in example 16, BoNT/B (●), LH$_N$/B (■) and LH$_N$/B-EGF (▲) were assayed for VAMP cleavage activity.

Figure 16:
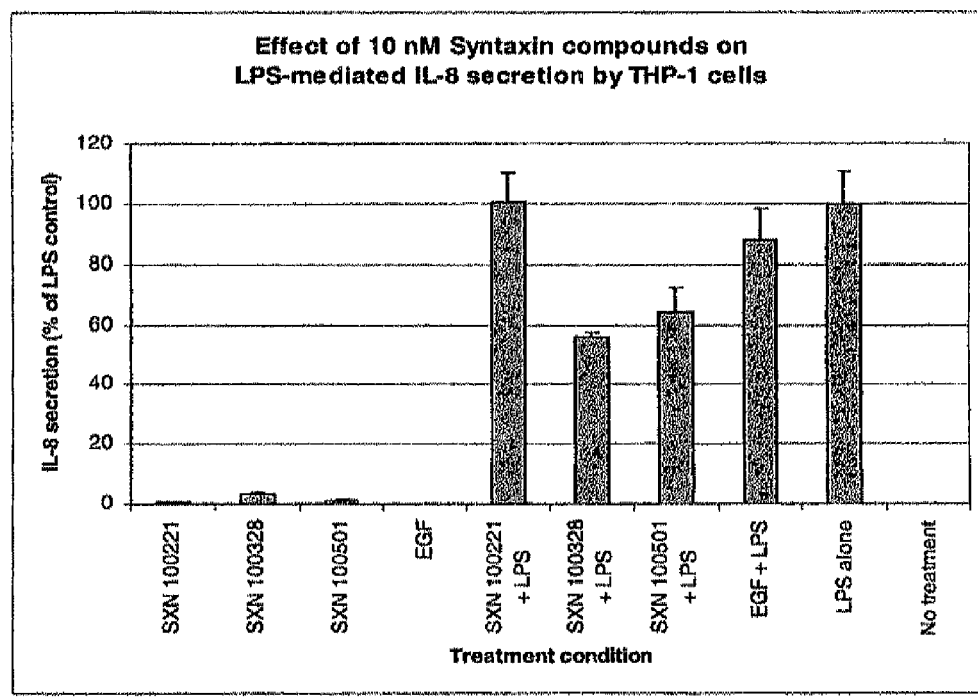
FIG. 16 shows effect of 10 nm Syntaxin compounds con LPS-mediated IL-8 secretion by THP-1 cells.

Referring to FIG. 16, using the methodology outlined in Example 17, the activity of EGF-LH$_N$/C (SXN100501) and EGF-LH$_N$/B (SXN100328) was assessed in THP-1 immune cells. The quantity of secreted IL-8 was determined by Luminex-based technology. Data are presented as % of LPS control.

Figure 17:
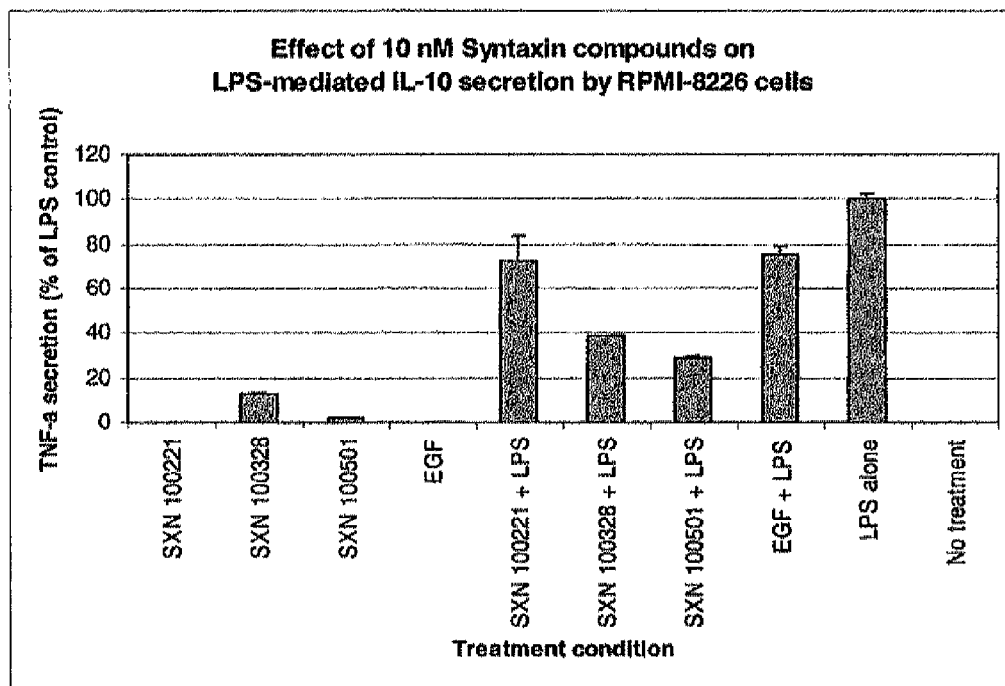
FIG. 17 shows effect of 10 nm Syntaxin compounds con LPS-mediated IL-10 secretion by RPMI-8226 cells.

Referring to FIG. 17, using the methodology outlined in Example 18, the activity of EGF-LH$_N$/C (SXN100501) and EGF-LH$_N$/B (SXN100328) was assessed in RPMI-8226 immune cells. The quantity of secreted IL-10 was determined by Luminex-based technology. Data are presented as % of LPS control.

Figure 18:
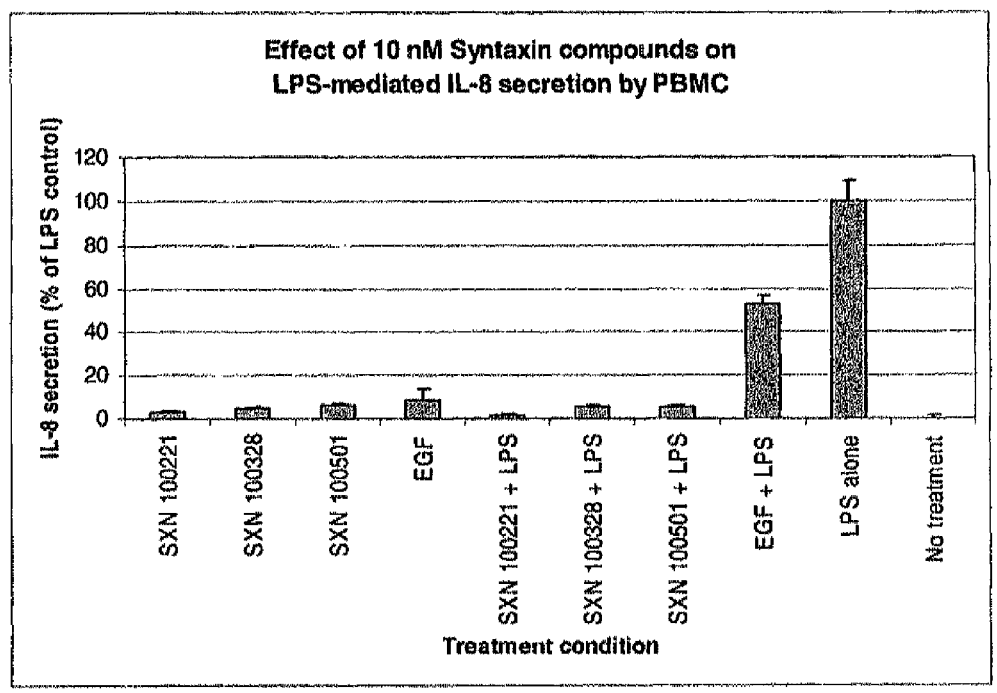
FIG. 18 shows effect of EGF and fusions on IL-8 production and on LPS-stimulated IL-8 secretion.

Referring to FIG. 18, using the methodology outlined in Example 19, the activity of EGF-LH$_N$/C (SXN100501) and EGF-LH$_N$/B (SXN100328) and CP-RGD-LH$_N$/C (SXN100221) was assessed in PBMC immune cells. The quantity of secreted IL-8 was determined by Luminex-based technology. Data are presented as % of LPS control.

Figure 19:
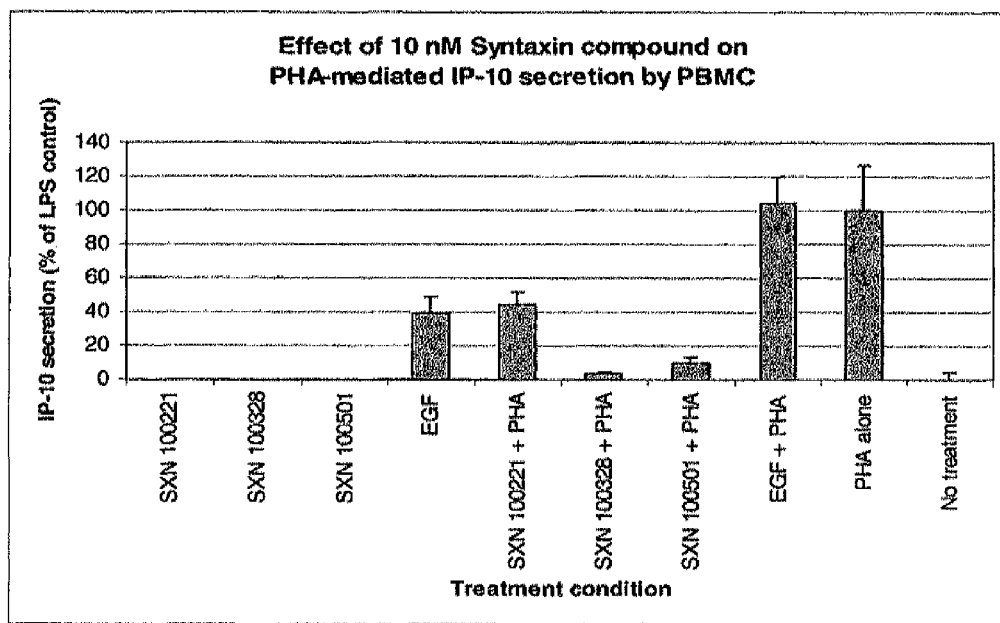
FIG. 19 shows effect of EGF and fusions on IP-10 production and on PHA-stimulated IP-10 secretion.

Referring to FIG. 19, using the methodology outlined in Example 20, the activity of EGF-LH$_N$/C (SXN100501) and EGF-LH$_N$/B (SXN100328) and CP-RGD-LH$_N$/C (SXN100221) was assessed in PBMC immune cells. The quantity of secreted IP-10 was determined by Luminex-based technology. Data are presented as % of PHA control.

EXAMPLES

Example 1

Production of a Conjugate of a Lectin from *Triticum vulgaris* and LH$_N$/A

Materials

Lectin from *Triticum vulgaris* (Wheat Germ Agglutinin—WGA) was obtained from Sigma Ltd.

SPDP was from Pierce Chemical Co.

PD-10 desalting columns were from Pharmacia.

Dimethylsulphoxide (DMSO) was kept anhydrous by storage over a molecular sieve.

Denaturing sodium dodecylsulphate polyacrylamide gel electrophoresis (SDS-PAGE) and non-denaturing polyacrylamide gel electrophoresis was performed using gels and reagents from Novex.

Additional reagents were obtained from Sigma Ltd. LH$_N$/A was prepared according to a previous method (Shone, C. C. and Tranter, H. S. (1995) in "Clostridial Neurotoxins—The molecular pathogenesis of tetanus and botulism", (Montecucco, C., Ed.), pp. 152-160, Springer). FPLC™ chromatography media and columns were obtained from Amersham Pharmacia Biotech, UK. Affi-gel Hz® matrix and materials were from BioRad, UK.

Preparation of an Anti-BoNT/a Antibody-Affinity Column

An antibody-affinity column was prepared with specific monoclonal antibodies essentially as suggested by the manufacturer's protocol. Briefly, monoclonal antibodies 5BA2.3 & 5BA9.3 which have different epitope recognition in the H$_C$ domain (Hallis, B., Fooks, S., Shone, C. and Hambleton, P. (1993) in "Botulinum and Tetanus Neurotoxins", (DasGupta, B. R., Ed.), pp. 433-436, Plenum Press, New York) were purified from mouse hybridoma tissue culture supernatant by Protein G (Amersham Pharmacia Biotech) chromatography. These antibodies represent a source of BoNT/A H$_C$-specific binding molecules and can be immobilised to a matrix or used free in solution to bind BoNT/A. In the presence of partially purified LH$_N$/A (which has no H$_C$ domain) these antibodies will only bind to BoNT/A. The antibodies 5BA2.3 & 5BA9.3 were pooled in a 3:1 ratio and two mg of the pooled antibody was oxidised by the addition of sodium periodate (final concentration of 0.2%) prior coupling to 1 ml Affi-Gel Hz.TM. gel (16 hours at room temperature). Coupling efficiencies were routinely greater than 65%. The matrix was stored at 4° C. in the presence of 0.02% sodium azide.

Purification Strategy for the Preparation of Pure LH$_N$/A

BoNT/A was treated with 17 μg trypsin per mg BoNT/A for a period of 72-120 hours. After this time no material of 150 kDa was observed by SDS-PAGE and Coomassie blue staining. The trypsin digested sample was chromatographed (FPLC™ system, Amersham Pharmacia Biotech) on a Mono Q™ column (HR5/5) to remove trypsin and separate the majority of BoNT/A from LH$_N$/A. The crude sample was loaded onto the column at pH 7 in 20 mM HEPES, 50 mM NaCl and 2 ml LH$_N$/A fractions eluted in a NaCl gradient from 50 mM to 150 mM. The slightly greater pI of BoNT/A (6.3) relative to LH$_N$/A (5.2) encouraged any BoNT/A remaining after trypsinisation to elute from the anion exchange column at a lower salt concentration than LH$_N$/A. LH$_N$/A containing fractions (as identified by SDS-PAGE) were pooled for application to the antibody column.

The semi-purified LH$_N$/A mixture was applied and reapplied at least 3 times to a 1-2 ml immobilised monoclonal antibody matrix at 20° C. After a total of 3 hours in contact with the immobilised antibodies, the LH$_N$/A-enriched supernatant was removed. Entrapment of the BoNT/A contaminant, rather than specifically binding the LH$_N$/A, enables the elution conditions to be maintained at the optimum for LH$_N$ stability. The use of harsh elution conditions e.g. low pH, high salt, chaotropic ions, which may have detrimental effects on LH$_N$ polypeptide folding and enzymatic activity, are therefore avoided. Treatment of the immobilised antibody column with 0.2M glycine/HCl pH2.5 resulted in regeneration of the column and elution of BoNT/A-reactive proteins of 150 kDa.

The LH$_N$/A enriched sample was then applied 2 times to a 1 ml HiTrap™ Protein G column (Amersham Pharmacia Biotech) at 20° C. Protein G was selected since it has a high affinity for mouse monoclonal antibodies. This step was included to remove BoNT/A-antibody complexes that may leach from the immunocolumn. Antibody species bind to the Protein G matrix allowing purified LH$_N$/A to elute, essentially by the method of Shone C. C., Hambleton, P., and Melling, J. 1987, Eur. J. Biochem. 167, 175-180, and as described in PCT/GB00/03519.

Methods

The lyophilised lectin was rehydrated in phosphate buffered saline (PBS) to a final concentration of 10 mg/ml. Aliquots of this solution were stored at −20° C. until use.

The WGA was reacted with an equal concentration of SPDP by the addition of a 10 mM stock solution of SPDP in DMSO with mixing. After one hour at room temperature the reaction was terminated by desalting into PBS over a PD-10 column.

The thiopyridone leaving group was removed from the product to release a free —SH group by reduction with dithiothreitol (DTT; 5 mM; 30 min). The thiopyridone and DTT were removed by once again desalting into PBS over a PD-10 column.

The LH$_N$/A was desalted into PBSE (PBS containing 1 mM EDTA). The resulting solution (0.5-1.0 mg/ml) was reacted with a four-fold molar excess of SPDP by addition of a 10 mM stock solution of SPDP in DMSO. After 3 h at room temperature the reaction was terminated by desalting over a PD-10 column into PBSE.

A portion of the derivatized LH$_N$/A was removed from the solution and reduced with DTT (5 mM, 30 min). This sample was analyzed spectrophotometrically at 280 nm and 343 nm to determine the degree of derivatisation. The degree of derivatisation achieved was 3.53+/−0.59 mol/mol.

The bulk of the derivatized LH$_N$/A and the derivatized WGA were mixed in proportions such that the WGA was in greater than three-fold molar excess. The conjugation reaction was allowed to proceed for >16 h at 4° C.

The product mixture was centrifuged to clear any precipitate that had developed. The supernatant was concentrated by centrifugation through concentrators (with 10000 molecular weight exclusion limit) before application to a Superose 12 column on an FPLC chromatography system (Pharmacia). The column was eluted with PBS and the elution profile followed at 280 nm.

Figure 1:
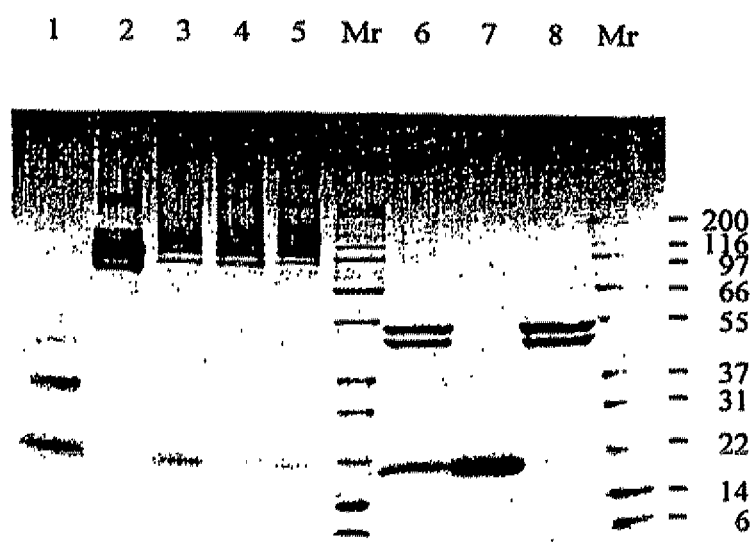
FIG. 1 shows SDS-PAGE analysis of WGA-LH$_N$/A purification scheme.

Fractions were analyzed by SDS-PAGE on 4-20% polyacrylamide gradient gels, followed by staining with Coomassie Blue. The major conjugate products have an apparent molecular mass of between 106-150 kDa, these are separated from the bulk of the remaining unconjugated $LH_N/A$ and more completely from the unconjugated WGA. Fractions containing conjugate were pooled prior to addition to PBS-washed N-acetylglucosamine-agarose. Lectin-containing proteins (i.e. WGA-$LH_N/A$ conjugate) remained bound to the agarose during washing with PBS to remove contaminants (predominantly unconjugated $LH_N/A$). WGA-$LH_N/A$ conjugate was eluted from the column by the addition of 0.3M N-acetylglucosamine (in PBS) and the elution profile followed at 280 nm. See FIG. 1 for SDS-PAGE profile of the whole purification scheme.

The fractions containing conjugate were pooled, dialysed against PBS, and stored at 4° C. until use.

Example 2

Activity of WGA-$LH_N/A$ in Cultured Endocrine Cells (HIT-T15)

The hamster pancreatic B cell line HIT-T15 is an example of a cell line of endocrine origin. It thus represents a model cell line for the investigation of inhibition of release effects of the agents. HIT-T15 cells possess surface moieties that allow for the binding, and internalisation, of WGA-$LH_N/A$.

In contrast, HIT-T15 cells lack suitable receptors for clostridial neurotoxins and are therefore not susceptible to botulinum neurotoxins (BoNTs).

Figure 2:
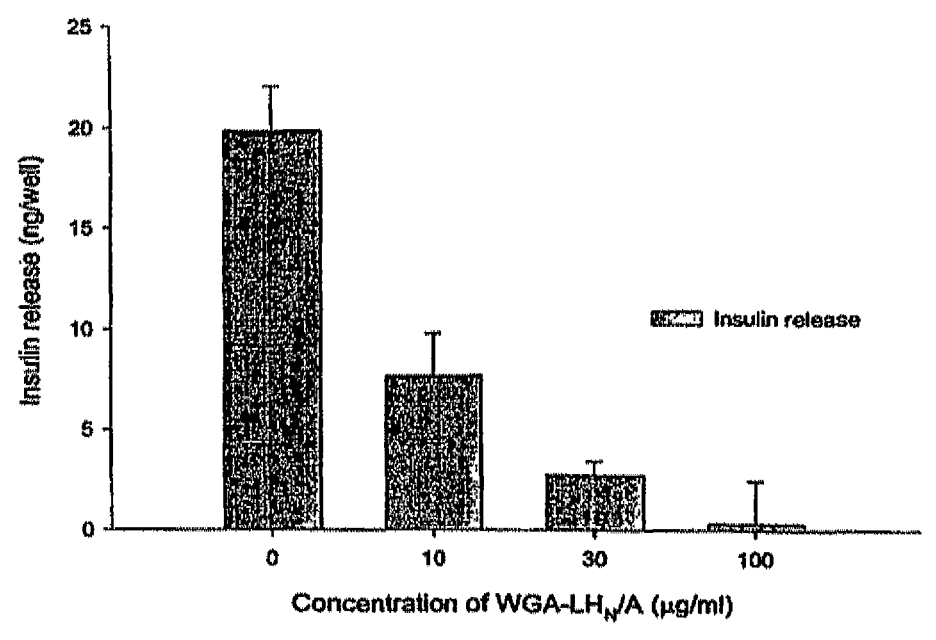

FIG. 2 illustrates the inhibition of release of insulin from HIT-T15 cells after prior incubation with WGA-$LH_N/A$. It is clear that dose-dependent inhibition is observed, indicating that WGA-$LH_N/A$ can inhibit the release of insulin from an endocrine cell model.

Figure 3:
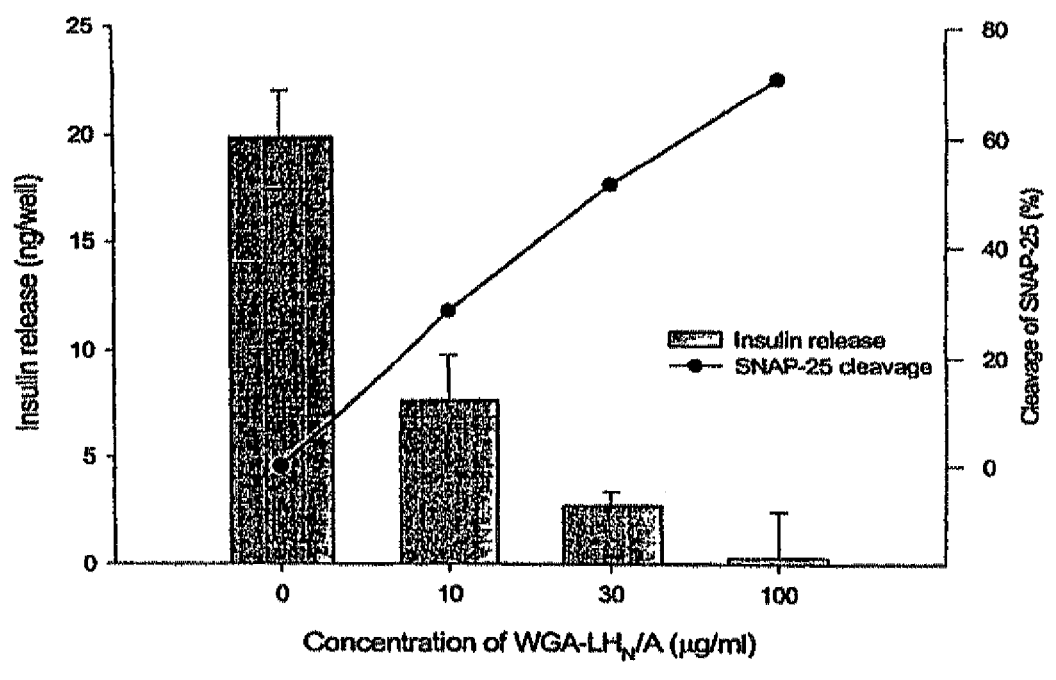

Inhibition of insulin release was demonstrated to correlate with cleavage of the SNARE protein, SNAP-25 (FIG. 3). Thus, inhibition of release of chemical messenger is due to a clostridial endopeptidase-mediated effects of SNARE-protein cleavage.

Materials

Insulin radioimmunoassay kits were obtained from Linco Research Inc., USA. Western blotting reagents were obtained from Novex.

Methods

HIT-T15 cells were seeded onto 12 well plates and cultured in RPMI-1640 medium containing 5% foetal bovine serum, 2 mM L-glutamine for 5 days prior to use. WGA-$LH_N/A$ was applied for 4 hours on ice, the cells were washed to remove unbound WGA-$LH_N/A$, and the release of insulin assayed 16 hours later. The release of insulin from HIT-T15 cells was assessed by radioimmunoassay exactly as indicated by the manufacturer's instructions.

Cells were lysed in 2M acetic acid/0.1% TFA. Lysates were dried then resuspended in 0.1M Hepes, pH 7.0. To extract the membrane proteins Triton-X-114 (10%, v/v) was added and incubated at 4° C. for 60 min. The insoluble material was removed by centrifugation and the supernatants were warmed to 37° C. for 30 min. The resulting two phases were separated by centrifugation and the upper phase discarded. The proteins in the lower phase were precipitated with chloroform/methanol for analysis by Western blotting.

The samples were separated by SDS-PAGE and transferred to nitrocellulose. Proteolysis of SNAP-25, a crucial component of the neurosecretory process and the substrate for the zinc-dependent endopeptidase activity of BoNT/A, was then detected by probing with an antibody (SMI-81) that recognises both the intact and cleaved forms of SNAP-25.

Example 3

Activity of WGA-$LH_N/A$ in Cultured Neuroendocrine Cells (PC12)

Figure 4:
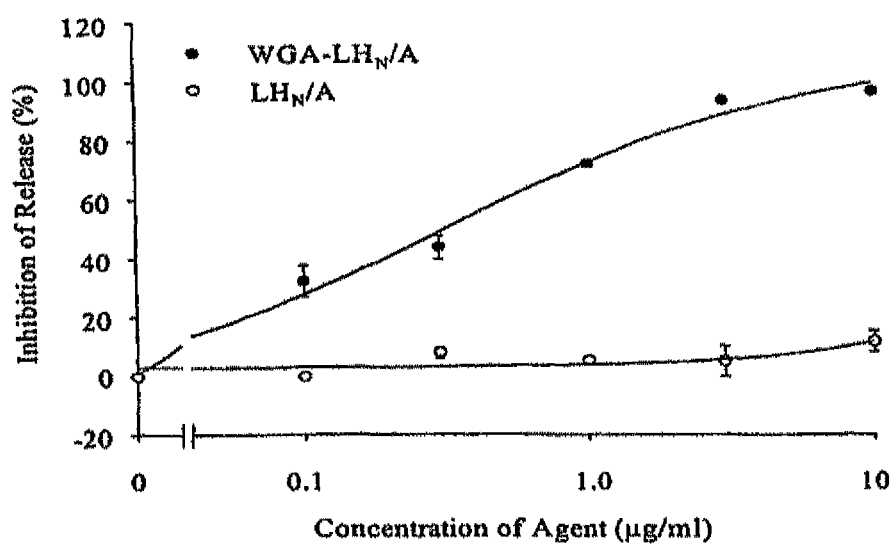
FIG. 4 shows activity of WGA-LH$_N$/A on release of [$^3$H]-noradrenaline from undifferentiated PC12 cells.

The rat pheochromocytoma PC12 cell line is an example of a cell line of neuroendocrine origin. In its undifferentiated form it has properties associated with the adrenal chromaffin cell [Greene and Tischler, in "Advances in Cellular Neurobiology" (Federoff and Hertz, eds), Vol. 3, p 373-414. Academic Press, New York, 1982]. It thus represents a model cell line for the investigation of inhibition of release effects of the agents. PC12 cells possess surface moieties that allow for the binding, and internalisation, of WGA-$LH_N/A$. FIG. 4 illustrates the inhibition of release of noradrenaline from PC12 cells after prior incubation with WGA-$LH_N/A$. It is clear that dose-dependent inhibition is observed, indicating that WGA-$LH_N/A$ can inhibit the release of hormone from a neuroendocrine cell model. Comparison of the inhibition effects observed with conjugate and the untargeted $LH_N/A$ demonstrate the requirement for a targeting moiety (TM) for efficient inhibition of transmitter release.

Methods

PC12 cells were cultured on 24 well plates in RPMI-1640 medium containing 10% horse serum, 5% foetal bovine serum, 1% L-glutamine. Cells were treated with a range of concentrations of WGA-$LH_N/A$ for three days. Secretion of noradrenaline was measured by labelling cells with [$^3$\H]-noradrenaline (2 µCi/ml, 0.5 ml/well) for 60 min. Cells were washed every 15 min for 1 hour then basal release determined by incubation with a balanced salt solution containing 5 mM KCl for 5 min. Secretion was stimulated by elevating the concentration of extracellular potassium (100 mM KCl) for 5 min. Radioactivity in basal and stimulated superfusates was determined by scintillation counting. Secretion was expressed as a percentage of the total uptake and stimulated secretion was calculated by subtracting basal. Inhibition of secretion was dose-dependent with an observed $IC_{50}$ of 0.63+/−0.15 µg/ml (n=3). Inhibition was significantly more potent when compared to untargeted endopeptidase ($LH_N/A$ in FIG. 4). Thus WGA-$LH_N/A$ inhibits release of neurotransmitter from a model neuroendocrine cell type.

Example 4

Expression and Purification of Catalytically Active Recombinant $LH_N/B$

The coding region for $LH_N/B$ was inserted in-frame to the 3' of the gene encoding maltose binding protein (MBP) in the expression vector pMAL (New England Biolabs). In this construct, the expressed MBP and $LH_N/B$ polypeptides are separated by a Factor Xa cleavage site.

Expression of the MBP-$LH_N/B$ in *E. coli* TG1 was induced by addition of IPTG to the growing culture at an approximate OD600 nm of 0.8. Expression was maintained for a further 3 hours in the presence of inducing agent prior to harvest by centrifugation. The recovered cell paste was stored at −20° C. until required.

The cell paste was resuspended in resuspension buffer (50 mM Hepes pH7.5+150 mM NaCl$^+$ a variety of protease inhibitors) at 6 ml buffer per gram paste. To this suspension was added lysozyme to a final concentration of 1 mg/ml. After 10 min at 0° C., the suspension was sonicated for 6×30 seconds at 24μ at 0° C. The broken cell paste was then centrifuged to remove cell debris and the supernatant recovered for chromatography.

In some situations, the cell paste was disrupted by using proprietary disruption agents such as BugBuster™ (Novagen) as per the manufacturers protocol. These agents were satisfactory for disruption of the cells to provide supernatant material for affinity chromatography.

The supernatant was applied to an immobilised amylose matrix at 0.4 ml/min to facilitate binding of the fusion protein. After binding, the column was washed extensively with resuspension buffer to remove contaminating proteins. Bound proteins were eluted by the addition of elution buffer (resuspension buffer+10 mM maltose) and fractions collected. Eluted fractions containing protein were pooled for treatment with Factor Xa.

On some occasions a further purification step was incorporated into the scheme, prior to the addition of Factor Xa. In these instances, the eluted fractions were made to 5 mM DTT and applied to a Pharmacia Mono-Q HR5/5 column (equilibrated in resuspension buffer) as part of an FPLC system. Proteins were bound to the column at 150 mM NaCl, before increased to 500 mM NaCl over a gradient. Fractions were collected and analysed for the presence of MBP-LH$_N$/B by Western blotting (probe antibody=guinea pig anti-BoNT/B or commercially obtained anti-MBP).

Cleavage of the fusion protein by Factor Xa was as described in the protocol supplied by the manufacturer (New England Biolabs). Cleavage of the fusion protein resulted in removal of the MBP fusion tag and separation of the LC and H$_N$ domains of LH$_N$/B. Passage of the cleaved mixture through a second immobilised maltose column removed free MBP from the mixture to leave purified disulphide-linked LH$_N$/B. This material was used for conjugation.

See FIG. 5 for an illustration of the purification of LH$_N$/B.

See FIG. 6 for an illustration of the in vitro catalytic activity of LH$_N$/B.

Example 5

Production of a Conjugate of a Lectin from *Triticum vulgaris* and LH$_N$/B

Materials

Lectin from *Triticum vulgaris* (WGA) was obtained from Sigma Ltd.

LH$_N$/B was prepared as described in Example 4.

SPDP was from Pierce Chemical Co.

PD-10 desalting columns were from Pharmacia.

Dimethylsulphoxide (DMSO) was kept anhydrous by storage over a molecular sieve.

Polyacrylamide gel electrophoresis was performed using gels and reagents from Novex.

Additional reagents were obtained from Sigma Ltd.

Methods

The lyophilised lectin was rehydrated in phosphate buffered saline (PBS) to a final concentration of 10 mg/ml. Aliquots of this solution were stored at −20° C. until use.

The WGA was reacted with an equal concentration of SPDP by the addition of a 10 mM stock solution of SPDP in DMSO with mixing. After one hour at room temperature the reaction was terminated by desalting into PBS over a PD-10 column.

The thiopyridone leaving group was removed from the product to release a free—SH group by reduction with dithiothreitol (DTT; 5 mM; 30 min). The thiopyridone and DTT were removed by once again desalting into PBS over a PD-10 column.

The recLH$_N$/B was desalted into PBS. The resulting solution (0.5-1.0 mg/ml) was reacted with a four-fold molar excess of SPDP by addition of a 10 mM stock solution of SPDP in DMSO. After 3 h at room temperature the reaction was terminated by desalting over a PD-10 column into PBS.

A portion of the derivatized recLH$_N$/B was removed from the solution and reduced with DTT (5 mM, 30 min). This sample was analysed spectrophotometrically at 280 nm and 343 nm to determine the degree of derivatisation.

The bulk of the derivatized recLH$_N$/B and the derivatized WGA were mixed in proportions such that the WGA was in greater than three-fold molar excess. The conjugation reaction was allowed to proceed for >16 h at 4° C.

The product mixture was centrifuged to clear any precipitate that had developed. The supernatant was concentrated by centrifugation through concentrators (with 10000 molecular weight exclusion limit) before application to a Superdex G-200 column on an FPLC chromatography system (Pharmacia). The column was eluted with PBS and the elution profile followed at 280 nm.

Fractions were analysed by SDS-PAGE on 4-20% polyacrylamide gradient gels, followed by staining with Coomassie Blue. The major conjugate products have an apparent molecular mass of between 106-150 kDa, these are separated from the bulk of the remaining unconjugated recLH$_N$/B and more completely from the unconjugated WGA. Fractions containing conjugate were pooled prior to addition to PBS-washed N-acetylglucosamine-agarose. Lectin-containing proteins (i.e. WGA-recLH$_N$/B conjugate) remained bound to the agarose during washing with PBS to remove contaminants (predominantly unconjugated recLH$_N$/B). WGA-recLH$_N$/B conjugate was eluted from the column by the addition of 0.3M N-acetylglucosamine (in PBS) and the elution profile followed at 280 nm.

The fractions containing conjugate were pooled, dialysed against PBS, and stored at 4° C. until use.

Example 6

Activity of BoNT/B in Vascular Endothelial Cells

Human umbilical vein endothelial cells (HUVEC) secrete von Willebrands Factor (vWF) when stimulated with a variety of cell surface receptor agonists including histamine. These cells maintain this property when prepared from full term umbilical cords and grown in culture (Loesberg et al 1983, Biochim. Biophys. Acta. 763, 160-168). The release of vWF by HUVEC thus represents a secretory activity of a non-neuronal cell type derived from the cardiovascular system. FIG. 7 illustrates the inhibition of the histamine stimulated release of vWF by HUVEC when previously treated with BoNT/B in low pH medium. Treatment of cells with toxins in low pH can be used as a technique for facilitating toxin penetration of the plasmalemma of cells refractory to exogenously applied clostridial neurotoxins.

This result clearly shows the ability of botulinum neurotoxins to inhibit secretory activity of non-neuronal cells in the cardiovascular system (see FIG. 7).

Methods

HUVEC were prepared by the method of Jaffe et al 1973, J. Clin. Invest. 52, 2745-2756. Cells were passaged once onto 24 well plates in medium 199 supplemented with 10% foetal calf serum, 10% newborn calf serum, 5 mM L-glutamine, 100 units/ml penicillin, 100 units/ml streptomycin, 20 µg/ml endothelial cell growth factor (Sigma). Cells were treated with DMEM pH 7.4, DMEM pH 4.7 (pH lowered with HCl) or DMEM, pH 4.7 with 500 nM BoNT/B for 2.5 hours then washed three times with HUVEC medium. 24 hours later cells were washed with a balanced salt solution, pH 7.4 and exposed to this solution for 30 minutes for the establishment of basal release. This was removed and BSS containing 1 mM histamine applied for a further 30 minutes. Superfusates were centrifuged to remove any detached cells and the quantity of vWF determined using an ELISA assay as described by Paleolog et al 1990, Blood. 75, 688-695. Stimulated secretion was then calculated by subtracting basal from the histamine stimulated release. Inhibition by BoNT/B treatment at pH 4.7 was calculated at 27.4% when compared to pH 4.7 treatment alone.

Example 7

Activity of BoNT/B in Mucus Secreting Cells

The LS180 colon carcinoma cell line is recognised as a model of mucin secreting cells (McCool, D. J., Forstner, J. F. and Forstner, G. G. 1994 Biochem. J. 302, 111-118). These cells have been shown to adopt goblet cell morphology and release high molecular weight mucin when stimulated with muscarinic agonists (eg carbachol), phorbol esters (PMA) and $Ca^{2+}$ ionophores (eg A23187) (McCool, D. J., Forstner, J. F. and Forstner, G. G. 1995 Biochem. J. 312, 125-133). These cells thus represent a non-neuronal cell type derived from the colon which can undergo regulated mucin secretion. FIG. 8 illustrates the inhibition of the ionomycin stimulated release of high molecular weight, $[^3H]$-glucosamine labelled material from LS180 cells by pretreatment with BoNT/B in low pH medium. Ionomycin is a $Ca^{2+}$ ionophore and treatment of cells with low pH medium has been previously shown to facilitate toxin entry into cells.

This result clearly shows the ability of botulinum neurotoxins to inhibit secretory activity of non-neuronal cells able to release mucin when stimulated with a secretagogue (see FIG. 8).

Methods

Mucin synthesising colon carcinoma LS180 cells were grown on Matrigel coated 24 well plates in minimum essential medium supplemented with 10% foetal calf serum, 2 mM L-glutamine and 1% non-essential amino acids (Sigma) Cells were treated with pH 7.4 medium, pH 4.7 medium and pH 4.7 medium containing 500 nM botulinum neurotoxin type B (BoNT/B) for four hours then labelled with $[^3H]$-glucosamine (1 µCi/ml, 0.5 ml/well) for 18 hours in L15 glucose free medium. Cells were then washed twice with a balanced salt solution (BSS) pH 7.4 and then 0.5 ml of BSS was applied for 30 minutes. This material was removed and 0.5 ml of BSS containing 10 µM ionomycin applied to stimulate mucin release. The stimulating solution was removed and all superfusates centrifuged to remove any detached cells. Supernatants were then centrifuged at 100,000×g for 1 hour. Supernatants were applied to Centricon centrifugal concentrators with a molecular weight cut-off of 100 kDa and centrifuged (2,500×g) until all liquid had passed through the membrane. Membranes were washed with BSS by centrifugation three times and then the membrane scintillation counted for retained, $[^3H]$-glucosamine labelled high molecular weight material.

Example 8

Activity of BoNT/B in Inflammatory Cells

The promyelocytic cell line HL60 can be differentiated into neutrophil like cells by the addition of dibutyryl cyclic AMP to the culture medium. Upon differentiation these cells increase their expression of characteristic enzymes such as β-glucuronidase. In this condition these cells therefore represent a model of a phagocytic cell type which contributes to the inflammatory response of certain disease states (e.g., rheumatoid arthritis). FIG. 9 illustrates the significant ($p>0.05$) inhibition of stimulated release of β-glucuronidase from dbcAMP differentiated HL60 cells by pre-treatment with BoNT/B in low pH medium.

This result clearly shows the ability of botulinum neurotoxins to inhibit the secretory activity of a non-neuronal cell type which is a model of the neutrophil a cell which participates in inflammation.

Methods

HL60 cells were cultured in RPMI 1640 medium containing 10% foetal calf serum and 2 mM glutamine. Cells were exposed to low pH and toxin for 2.5 hours then washed 3 times and differentiated by the addition of dibutyryl cyclic AMP (dbcAMP) to a final concentration of 300 µM. Cells were differentiated for 40 hours and then stimulated release of β-glucuronidase activity was determined. Cells were treated with cytochalasin B (5 µM) 5 minutes before stimulation. Cells were stimulated with 1 µM N-formyl-Met-Leu-Phe with 100 µM ATP for 10 minutes then centrifuged and the supernatant taken for assay of β-glucuronidase activity. Activity was measured in cell lysates and the amount released expressed as a percentage of the total cellular content of enzyme.

β-glucuronidase activity was determined according to the method of Absolom D. R. 1986, (Methods in Enzymology, 132, 160) using p-Nitrophenyl-β-D-glucuronide as the substrate.

Example 9

Preparation of a $LH_N/B$ Backbone Construct

The following procedure creates a clone for use as an expression backbone for multidomain fusion expression. This example is based on preparation of a serotype B based clone (SEQ ID NO:1).

Preparation of Cloning and Expression Vectors pCR 4 (Invitrogen) is the chosen standard cloning vector chosen due to the lack of restriction sequences within the vector and adjacent sequencing primer sites for easy construct confirmation. The expression vector is based on the pMAL (NEB) expression vector which has the desired restriction sequences within the multiple cloning site in the correct orientation for construct insertion (BamHI-SalI-PstI-HindIII). A fragment of the expression vector has been removed to create a non-mobilisable plasmid and a variety of different fusion tags have been inserted to increase purification options.

Preparation of LC/B

The LC/B is created by one of two ways:

The DNA sequence is designed by back translation of the LC/B amino acid sequence (obtained from freely available database sources such as GenBank (accession number P10844) or Swissprot (accession locus BXB_CLOBO) using one of a variety of reverse translation software tools (for example EditSeq best *E. coli* reverse translation (DNASTAR Inc.), or Backtranslation tool v2.0 (Entelechon)). BamHI/SalI recognition sequences are incorporated at the 5' and 3' ends respectively of the sequence maintaining the correct reading frame. The DNA sequence is screened (using software such as MapDraw, DNASTAR Inc.) for restriction enzyme cleavage sequences incorporated during the back translation. Any cleavage sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence containing the LC/B open reading frame (ORF) is then commercially synthesized (for example by Entelechon, Geneart or Sigma-Genosys) and is provided in the pCR 4 vector.

The alternative method is to use PCR amplification from an existing DNA sequence with BamHI and SalI restriction enzyme sequences incorporated into the 5' and 3' PCR primers respectively. Complementary oligonucleotide primers are chemically synthesised by a Supplier (for example MWG or Sigma-Genosys) so that each pair has the ability to hybridize to the opposite strands (3' ends pointing "towards" each other) flanking the stretch of *Clostridium* target DNA, one oligonucleotide for each of the two DNA strands. To generate a PCR product the pair of short oligonucleotide primers specific for the *Clostridium* DNA sequence are mixed with the *Clostridium* DNA template and other reaction components and placed in a machine (the 'PCR machine') that can change the incubation temperature of the reaction tube automatically, cycling between approximately 94° C. (for denaturation), 55° C. (for oligonucleotide annealing), and 72° C. (for synthesis). Other reagents required for amplification of a PCR product include a DNA polymerase (such as Taq or Pfu polymerase), each of the four nucleotide dNTP building blocks of DNA in equimolar amounts (50-200 μM) and a buffer appropriate for the enzyme optimised for Mg2+ concentration (0.5-5 mM).

The amplification product is cloned into pCR 4 using either, TOPO TA cloning for Taq PCR products or Zero Blunt TOPO cloning for Pfu PCR products (both kits commercially available from Invitrogen). The resultant clone is checked by sequencing. Any additional restriction sequences which are not compatible with the cloning system are then removed using site directed mutagenesis (for example using Quickchange (Stratagene Inc.)).

Preparation of $H_N$/B Insert

The $H_N$ is created by one of two ways:

The DNA sequence is designed by back translation of the $H_N$/B amino acid sequence (obtained from freely available database sources such as GenBank (accession number P10844) or Swissprot (accession locus BXB_CLOBO)) using one of a variety of reverse translation software tools (for example EditSeq best *E. coli* reverse translation (DNASTAR Inc.), or Back translation tool v2.0 (Entelechon)). A PstI restriction sequence added to the N-terminus and XbaI-stop codon-HindIII to the C-terminus ensuring the correct reading frame in maintained. The DNA sequence is screened (using software such as MapDraw, DNASTAR Inc.) for restriction enzyme cleavage sequences incorporated during the back translation. Any sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence is then commercially synthesized (for example by Entelechon, Geneart or Sigma-Genosys) and is provided in the pCR 4 vector.

The alternative method is to use PCR amplification from an existing DNA sequence with PstI and XbaI-stop codon-HindIII restriction enzyme sequences incorporated into the 5' and 3' PCR primers respectively. The PCR amplification is performed as described above. The PCR product is inserted into pCR 4 vector and checked by sequencing. Any additional restriction sequences which are not compatible with the cloning system are then removed using site directed mutagenesis (for example using Quickchange (Stratagene Inc.)).

Preparation of the Spacer (LC-$H_N$ Linker)

The LC-$H_N$ linker can be designed from first principle, using the existing sequence information for the linker as the template. For example, the serotype B linker (in this case defined as the inter-domain polypeptide region that exists between the cysteines of the disulphide bridge between LC and $H_N$) has the sequence KSVKAPG (SEQ ID NO:30). This sequence information is freely available from available database sources such as GenBank (accession number P10844) or Swissprot (accession locus BXB_CLOBO). For generation of a specific protease cleavage site, the recognition sequence for enterokinase is inserted into the activation loop to generate the sequence VDEEKLYDDDDKDRWGSSLQ (SEQ ID NO:31). Using one of a variety of reverse translation software tools (for example EditSeq best *E. coli* reverse translation (DNASTAR Inc.), or Backtranslation tool v2.0 (Entelechon)), the DNA sequence encoding the linker region is determined. BamHI/SalI and PstI/XbaI/stop codon/HindIII restriction enzyme sequences are incorporated at either end, in the correct reading frames. The DNA sequence is screened (using software such as MapDraw, DNASTAR Inc.) for restriction enzyme cleavage sequences incorporated during the back translation. Any sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence is then commercially synthesized (for example by Entelechon, Geneart or Sigma-Genosys) and is provided in the pCR 4 vector. If it is desired to clone the linker out of pCR 4 vector, the vector (encoding the linker) is cleaved with either BamHI+SalI or PstI+XbaI combination restriction enzymes. This cleaved vector then serves as the recipient vector for insertion and ligation of either the LC DNA (cleaved with BamHI/SalI) or $H_N$ DNA (cleaved with PstI/XbaI). Once the LC or the $H_N$ encoding DNA is inserted upstream or downstream of the linker DNA, the entire LC-linker or linker-$H_N$ DNA fragment can the be isolated and transferred to the backbone clone.

As an alternative to independent gene synthesis of the linker, the linker-encoding DNA can be included during the synthesis or PCR amplification of either the LC or $H_N$.

Assembly and Confirmation of the Backbone Clone

The LC or the LC-linker is cut out from the pCR 4 cloning vector using BamHI/SalI or BamHI/PstI restriction enzymes digests. The pMAL expression vector is digested with the same enzymes but is also treated with calf intestinal protease (CIP) as an extra precaution to prevent re-circularisation. Both the LC or LC-linker region and the pMAL vector backbone are gel purified. The purified insert and vector backbone are ligated together using T4 DNA ligase and the product is transformed with TOP10 cells which are then screened for LC insertion using BamHI/SalI or BamHI/PstI restriction digestion. The process is then repeated for the $H_N$ or linker-$H_N$ insertion into the PstI/HindIII or SalI/HindIII sequences of the pMAL-LC construct.

Screening with restriction enzymes is sufficient to ensure the final backbone is correct as all components are already sequenced confirmed, either during synthesis or following PCR amplification. However, during the sub-cloning of some components into the backbone, where similar size fragments are being removed and inserted, sequencing of a small region to confirm correct insertion is required.

Example 10

Preparation of a $LH_N$/C Backbone Construct

The following procedure creates a clone for use as an expression backbone for multidomain fusion expression. This example is based on preparation of a serotype C based clone (SEQ ID NO:2).

Preparation of Cloning and Expression Vectors pCR 4 (Invitrogen) is the chosen standard cloning vector chosen due to the lack of restriction sequences within the vector and adjacent sequencing primer sites for easy construct confirmation. The expression vector is based on the pMAL (NEB) expression vector which has the desired restriction sequences within the multiple cloning site in the correct orientation for construct insertion (BamHI-SalI-PstI-HindIII). A fragment of the expression vector has been removed to create a non-mobilisable plasmid and a variety of different fusion tags have been inserted to increase purification options.

Preparation of LC/C

The LC/C is created by one of two ways.

The DNA sequence is designed by back translation of the LC/C amino acid sequence (obtained from freely available database sources such as GenBank (accession number P18640) or Swissprot (accession locus BXC1_CLOBO)) using one of a variety of reverse translation software tools (for example EditSeq best *E. coli* reverse translation (DNASTAR Inc.), or Backtranslation tool v2.0 (Entelechon)). BamHI/SalI recognition sequences are incorporated at the 5' and 3' ends respectively of the sequence maintaining the correct reading frame. The DNA sequence is screened (using software such as MapDraw, DNASTAR Inc.) for restriction enzyme cleavage sequences incorporated during the back translation. Any cleavage sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence containing the LC/C open reading frame (ORF) is then commercially synthesized (for example by Entelechon, Geneart or Sigma-Genosys) and is provided in the pCR 4 vector.

The alternative method is to use PCR amplification from an existing DNA sequence with BamHI and SalI restriction enzyme sequences incorporated into the 5' and 3' PCR primers respectively. Complementary oligonucleotide primers are chemically synthesised by a Supplier (for example MWG or Sigma-Genosys) so that each pair has the ability to hybridize to the opposite strands (3' ends pointing "towards" each other) flanking the stretch of *Clostridium* target DNA, one oligonucleotide for each of the two DNA strands. To generate a PCR product the pair of short oligonucleotide primers specific for the *Clostridium* DNA sequence are mixed with the *Clostridium* DNA template and other reaction components and placed in a machine (the 'PCR machine') that can change the incubation temperature of the reaction tube automatically, cycling between approximately 94° C. (for denaturation), 55° C. (for oligonucleotide annealing), and 72° C. (for synthesis). Other reagents required for amplification of a PCR product include a DNA polymerase (such as Taq or Pfu polymerase), each of the four nucleotide dNTP building blocks of DNA in equimolar amounts (50-200 μM) and a buffer appropriate for the enzyme optimised for Mg2+ concentration (0.5-5 mM).

The amplification product is cloned into pCR 4 using either, TOPO TA cloning for Taq PCR products or Zero Blunt TOPO cloning for Pfu PCR products (both kits commercially available from Invitrogen). The resultant clone is checked by sequencing. Any additional restriction sequences which are not compatible with the cloning system are then removed using site directed mutagenesis (for example using Quickchange (Stratagene Inc.)).

Preparation of $H_N$/C Insert

The $H_N$ is created by one of two ways:

The DNA sequence is designed by back translation of the $H_N$/C amino acid sequence (obtained from freely available database sources such as GenBank (accession number P18640) or Swissprot (accession locus BXC1_CLOBO)) using one of a variety of reverse translation software tools (for example EditSeq best *E. coli* reverse translation (DNASTAR Inc.), or Back translation tool v2.0 (Entelechon)). A PstI restriction sequence added to the N-terminus and XbaI-stop codon-HindIII to the C-terminus ensuring the correct reading frame in maintained. The DNA sequence is screened (using software such as MapDraw, DNASTAR Inc.) for restriction enzyme cleavage sequences incorporated during the back translation. Any sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence is then commercially synthesized (for example by Entelechon, Geneart or Sigma-Genosys) and is provided in the pCR 4 vector.

The alternative method is to use PCR amplification from an existing DNA sequence with PstI and XbaI-stop codon-HindIII restriction enzyme sequences incorporated into the 5' and 3' PCR primers respectively. The PCR amplification is performed as described above. The PCR product is inserted into pCR 4 vector and checked by sequencing. Any additional restriction sequences which are not compatible with the cloning system are then removed using site directed mutagenesis (for example using Quickchange (Stratagene Inc.)).

Preparation of the Spacer (LC-$H_N$ Linker)

The LC-$H_N$ linker can be designed from first principle, using the existing sequence information for the linker as the template. For example, the serotype C linker (in this case defined as the inter-domain polypeptide region that exists between the cysteines of the disulphide bridge between LC and $H_N$) has the sequence HKAIDGRSLYNKTLD (SEQ ID NO:32). This sequence information is freely available from available database sources such as GenBank (accession number P18640) or Swissprot (accession locus BXC1_CLOBO). For generation of a specific protease cleavage site, the recognition sequence for enterokinase is inserted into the activation loop to generate the sequence VDGIITSKTKSD-DDDKNKALNLQ (SEQ ID NO:33). Using one of a variety of reverse translation software tools (for example EditSeq best *E. coli* reverse translation (DNASTAR Inc.), or Backtranslation tool v2.0 (Entelechon)), the DNA sequence encoding the linker region is determined. BamHI/SalI and PstI/XbaI/stop codon/HindIII restriction enzyme sequences are incorporated at either end, in the correct reading frames. The DNA sequence is screened (using software such as MapDraw, DNASTAR Inc.) for restriction enzyme cleavage sequences incorporated during the back translation. Any sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence is then commercially synthesized (for example by Entelechon, Geneart or Sigma-Genosys) and is provided in the pCR 4 vector. If it is desired to clone the linker out of pCR 4 vector, the vector (encoding the linker) is cleaved with either BamHI+SalI or PstI+XbaI combination restriction enzymes. This cleaved vector then serves as the recipient vector for insertion and ligation of either the LC DNA (cleaved with BamHI/SalI) or $H_N$ DNA (cleaved with PstI/XbaI). Once the LC or the $H_N$ encoding DNA is inserted upstream or downstream of the linker DNA, the entire LC-linker or linker-$H_N$ DNA fragment can the be isolated and transferred to the backbone clone.

As an alternative to independent gene synthesis of the linker, the linker-encoding DNA can be included during the synthesis or PCR amplification of either the LC or $H_N$.

Assembly and Confirmation of the Backbone Clone

The LC or the LC-linker is cut out from the pCR 4 cloning vector using BamHI/SalI or BamHI/PstI restriction enzymes digests. The pMAL expression vector is digested with the same enzymes but is also treated with calf intestinal protease (CIP) as an extra precaution to prevent re-circularisation. Both the LC or LC-linker region and the pMAL vector backbone are gel purified. The purified insert and vector backbone are ligated together using T4 DNA ligase and the product is transformed with TOP10 cells which are then screened for LC insertion using BamHI/SalI or BamHI/PstI restriction digestion. The process is then repeated for the $H_N$ or linker-$H_N$ insertion into the PstI/HindIII or SalI/HindIII sequences of the pMAL-LC construct.

Screening with restriction enzymes is sufficient to ensure the final backbone is correct as all components are already sequenced confirmed, either during synthesis or following PCR amplification. However, during the sub-cloning of some components into the backbone, where similar size fragments are being removed and inserted, sequencing of a small region to confirm correct insertion is required.

Example 11

Construction, Expression, and Purification of a $LH_N$/C-EGF Fusion Protein

Preparation of Spacer-EGF Insert

For presentation of an EGF sequence at the C-terminus of the $H_N$ domain, a DNA sequence is designed to flank the spacer and targeting moiety (TM) regions allowing incorporation into the backbone clone (SEQ ID NO:2). The DNA sequence can be arranged as BamHI-SalI-PstI-XbaI-spacer-EGF-stop codon-HindIII (SEQ ID NO:3). The DNA sequence can be designed using one of a variety of reverse translation software tools (for example EditSeq best *E. coli* reverse translation (DNASTAR Inc.), or Backtranslation tool v2.0 (Entelechon)). Once the TM DNA is designed, the additional DNA required to encode the preferred spacer is created in silico. It is important to ensure the correct reading frame is maintained for the spacer, EGF and restriction sequences and that the XbaI sequence is not preceded by the bases, TC which would result on DAM methylation. The DNA sequence is screened for restriction sequence incorporated and any additional sequences are removed manually from the remaining sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence is then commercially synthesized (for example by Entelechon, Geneart or Sigma-Genosys) and is provided in the pCR 4 vector.

Insertion of Spacer-EGF into Backbone

In order to create a LC-linker-$H_N$-spacer-EGF construct (SEQ ID NO:4) using the backbone construct (SEQ ID NO:2) and the newly synthesised pCR 4-spacer-TM vector encoding the EGF TM (SEQ ID NO:3), the following two-step method is employed. Firstly, the $H_N$ domain is excised from the backbone clone using restriction enzymes PstI and XbaI and ligated into similarly digested pCR 4-spacer-EGF vector. This creates an $H_N$-spacer-EGF ORF in pCR 4 that can be excised from the vector using restriction enzymes PstI and HindIII for subsequent ligation into similarly cleaved backbone or expression construct. The final construct contains the LC-linker-$H_N$-spacer-EGF ORF (SEQ ID NO:4) for transfer into expression vectors for expression to result in a fusion protein of the sequence illustrated in SEQ ID NO:5.

Screening with restriction enzymes is sufficient to ensure the final backbone is correct as all components are already sequenced confirmed, either during synthesis or following PCR amplification. However, during the sub-cloning of some components into the backbone, where similar size fragments are being removed and inserted, sequencing of a small region to confirm correct insertion is required.

Alternative Construction Approach

As an alternative to the methodologies described above for the construction of $LH_N$/C-EGF, complete gene synthesis has been used to create a single DNA insert that encodes the LC, the $H_N$, linkers, spacers and a protease activation site. The synthetic DNA is designed to have a NdeI restriction site at the 5' end and a HindIII restriction site at the 3' end to facilitate direct cloning into expression vectors. The sequence of the engineered coding region is subject to the same codon utilisation analysis as described above. The sequence of the synthetic DNA is illustrated in SEQ ID NO:19, and the protein that it encodes is illustrated in SEQ ID NO:20.

Expression of $LH_N$/C-EGF Fusion Protein

Expression of the $LH_N$/C-EGF fusion protein is achieved using the following protocol. Inoculate 100 ml of modified TB containing 0.2% glucose and 100 μg/ml ampicillin in a 250 ml flask with a single colony from the $LH_N$/C-EGF expression strain. Grow the culture at 37° C., 225 rpm for 16 hours. Inoculate 1 L of modified TB containing 0.2% glucose and 100 μg/ml ampicillin in a 2 L flask with 10 ml of overnight culture. Grow cultures at 37° C. until an approximate OD600 nm of 0.5 is reached at which point reduce the temperature to 16° C. After 1 hour induce the cultures with 1 mM IPTG and grow at 16° C. for a further 16 hours.

Purification of LH$_N$/C-EGF Fusion Protein

Defrost falcon tube containing 25 ml 50 mM HEPES pH 7.2 200 mM NaCl and approximately 10 g of *E. coli* BL21 cell paste. Sonicate the cell paste on ice 30 seconds on, 30 seconds off for 10 cycles at a power of 22 microns ensuring the sample remains cool. Spin the lysed cells at 18 000 rpm, 4° C. for 30 minutes. Load the supernatant onto a 0.1 M NiSO4 charged Chelating column (20-30 ml column is sufficient) equilibrated with 50 mM HEPES pH 7.2 200 mM NaCl. Using a step gradient of 10 and 40 mM imidazole, wash away the non-specific bound protein and elute the fusion protein with 100 mM imidazole. Dialyse the eluted fusion protein against 5 L of 50 mM HEPES pH 7.2 200 mM NaCl at 4° C. overnight and measure the OD of the dialysed fusion protein. Add 1 unit of factor Xa per 100 µg fusion protein and incubate at 25° C. static overnight. Load onto a 0.1 M NiSO$_4$ charged Chelating column (20-30 ml column is sufficient) equilibrated with 50 mM HEPES pH 7.2 200 mM NaCl. Wash column to baseline with 50 mM HEPES pH 7.2 200 mM NaCl. Using a step gradient of 10 and 40 mM imidazole, wash away the non-specific bound protein and elute the fusion protein with 100 mM imidazole. Dialyse the eluted fusion protein against 5 L of 50 mM HEPES pH 7.2 200 mM NaCl at 4° C. overnight and concentrate the fusion to about 2 mg/ml, aliquot sample and freeze at −20° C. Test purified protein using OD, BCA and purity analysis. FIG. 8 demonstrates the purified protein as analysed be SDS-PAGE.

Example 12

Construction, Expression and Purification of a LH$_N$/B-EGF Fusion Protein

The LC-H$_N$ linker is designed using the methods described in example 11 using the B serotype linker arranged as BamHI-SalI-PstI-XbaI-spacer-EGF-stop codon-HindIII (SEQ ID NO:3). The $LH_N$/B-EGF fusion is then assembled using the $LH_N$/B backbone clone (SEQ ID NO:1) made using the methods described in example 9 and constructed using methods described in example 11. The final construct contains the LC-linker-$H_N$-spacer-EGF ORF (SEQ ID NO:6) for transfer into expression vectors for expression to result in a fusion protein of the sequence illustrated in SEQ ID NO:7. The resultant expression plasmid, pMAL $LH_N$/B-EGF is transformed into *E. coli* BL21 for recombinant protein expression. Expression and purification of the fusion protein was carried out as described in example 6 except that enterokinase replaced factor Xa in the activation of the fusion protein. FIG. 9 demonstrates the purified protein as analysed by SDS-PAGE.

Example 13

Preparation and Purification of a $LH_N$/C-RGD Fusion Protein

Preparation of Spacer-RGD Insert

For presentation of an RGD sequence at the C-terminus of the $H_N$ domain, a DNA sequence is designed to flank the spacer and TM regions allowing incorporation into the backbone clone (SEQ ID NO:2). The DNA sequence can be arranged as BamHI-SalI-PstI-XbaI-spacer-SpeI-RGD-stop codon-HindIII (SEQ ID NO:8). The DNA sequence can be designed using one of a variety of reverse translation software tools (for example EditSeq best *E. coli* reverse translation (DNASTAR Inc.), or Backtranslation tool v2.0 (Entelechon)). Once the TM DNA is designed, the additional DNA required to encode the preferred spacer is created in silico. It is important to ensure the correct reading frame is maintained for the spacer, RGD and restriction sequences and that the XbaI sequence is not preceded by the bases, TC which would result on DAM methylation. The DNA sequence is screened for restriction sequence incorporated and any additional sequences are removed manually from the remaining sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence is then commercially synthesized (for example by Entelechon, Geneart or Sigma-Genosys) and is provided in the pCR 4 vector.

Insertion of Spacer-RGD into Backbone

In order to create a LC-linker-$H_N$-spacer-RGD construct (SEQ ID NO:9) using the backbone construct (SEQ ID NO:2) and the newly synthesised pCR 4-spacer-TM vector encoding the RGD TM (SEQ ID NO:8), the following two-step method is employed. Firstly, the $H_N$ domain is excised from the backbone clone using restriction enzymes PstI and XbaI and ligated into similarly digested pCR 4-spacer-RGD vector. This creates an $H_N$-spacer-RGD ORF in pCR 4 that can be excised from the vector using restriction enzymes PstI and HindIII for subsequent ligation into similarly cleaved backbone or expression construct. The final construct contains the LC-linker-$H_N$-spacer-RGD ORF (SEQ ID NO:9) for transfer into expression vectors for expression to result in a fusion protein of the sequence illustrated in SEQ ID NO:10.

Screening with restriction enzymes is sufficient to ensure the final backbone is correct as all components are already sequenced confirmed, either during synthesis or following PCR amplification. However, during the sub-cloning of some components into the backbone, where similar size fragments are being removed and inserted, sequencing of a small region to confirm correct insertion is required.

Expression and purification of the fusion protein was carried out as described in example 11. FIG. 10 demonstrates the purified protein as analysed by SDS-PAGE.

Example 14

Preparation and Purification of a $LH_N$/C-Cyclic RGD Fusion Protein

The LC-$H_N$ linker can be designed using the methods described in example 13 using the C serotype linker arranged as BamHI-SalI-PstI-XbaI-spacer-SpeI-cyclic RGD-stop codon-HindIII (SEQ ID NO:11). The $LH_N$/C-cyclic RGD fusion is then assembled using the $LH_N$/C backbone clone (SEQ ID NO:2) made using the methods described in example 10 and constructed using methods described in example 13. The final construct contains the LC-linker-$H_N$-spacer-cyclic RGD ORF (SEQ ID NO:11) for transfer into expression vectors for expression to result in a fusion protein of the sequence illustrated in SEQ ID NO:13. The resultant expression plasmid, pMAL $LH_N$/C-cyclic RGD was transformed into *E. coli* BL21 for recombinant protein expression. Expression and purification of the fusion protein was carried out as described in example 11. FIG. 11 demonstrates the purified protein as analysed by SDS-PAGE.

Example 15

Preparation and Purification of a LC/C-RGD-$H_N$/C Fusion Protein

In order to create the LC-linker-RGD-spacer-$H_N$ construct (SEQ ID NO:15), the pCR 4 vector encoding the linker (SEQ ID NO:14) is cleaved with BamHI+SalI restriction enzymes. This cleaved vector then serves as the recipient vector for insertion and ligation of the LC/C DNA (SEQ ID NO:2) cleaved with BamHI+SalI. The resulting plasmid DNA is then cleaved with PstI+XbaI restriction enzymes and serves as the recipient vector for the insertion and ligation of the $H_N$/C DNA (SEQ ID NO:2) cleaved with PstI+XbaI. The final construct contains the LC-linker-RGD-spacer-$H_N$ ORF (SEQ ID NO:15) for transfer into expression vectors for expression to result in a fusion protein of the sequence illustrated in SEQ ID NO:16. The resultant expression plasmid, pMAL LC/C-RGD-$H_N$/C was transformed into *E. coli* BL21 for recombinant protein expression. Expression and purification of the fusion protein was carried out as described in example 11. FIG. 12 demonstrates the purified protein as analysed by SDS-PAGE.

Alternative Construction Approach

As an alternative to the methodologies described above for the construction of LC-linker-RGD-spacer-$H_N$, complete gene synthesis has been used to create a single DNA insert that encodes the LC, the $H_N$, linkers, spacers and a protease activation site. The synthetic DNA is designed to have a NdeI restriction site at the 5' end and a HindIII restriction site at the 3' end to facilitate direct cloning into expression vectors. The sequence of the engineered coding region is subject to the same codon utilisation analysis as described above. The sequence of the synthetic DNA is illustrated in SEQ ID NO:17, and the protein that it encodes is illustrated in SEQ ID NO:18.

Example 16

VAMP Cleavage Activity Assay

A range of concentrations of $LH_N$/B-EGF in cleavage buffer (50 mM HEPES pH7.4, 10 mM DTT, 20 μM $ZnCl_2$, 1% FBS) are incubated with biotinylated VAMP substrate (1 mg/ml) for two hours at 37° C. in a shaking incubator. The cleavage reaction is transferred to a washed 96-well streptavidin coated plate and incubated at 37° C. in a shaking incubator for 5 minutes. The plate is washed three times with PBS-0.1% tween-20 (PBS-T). The wells are blocked with blocking buffer (5% FCS in PBS-T) for 1 hour at 37° C. The primary antibody (anti-FESS) is added at a dilution of 1 in 500 in blocking buffer and the plate is incubated at 37° C. for 1 hour. The plate is washed three times with PBS-T and the secondary antibody (anti guinea pig HRP conjugate) diluted 1 in 1000 in blocking buffer is applied. Following 1 hour incubation at 37° C. the plate is developed with bioFX TMB substrate. Colour development is allowed to proceed for 1-5 minutes and then stopped with stop solution. The absorbance is measured at 450 nm. FIG. 13 shows the VAMP cleavage activity of $LH_N$/B-EGF fusion protein.

Example 17

Activity of EGF-$LH_N$/C and EGF-$LH_N$/B in THP-1 Immune Cells

The THP-1 cell line is a human-derived suspension (non-adherent) culture that is used frequently to provide a model system for primary monocytes. It is a well characterized model and over 2000 reviewed publications have utilized the THP-1 line to investigate molecular and cellular processes. Recent studies have demonstrated the utility of the THP-1 cell line as a model to assess the secretion of anti- and pro-inflammatory cytokines (Qiu et. al. 2007 J. Lipid Res. 48(2) 385-394, Prunet et. al. 2006 Cytometry A. 69, 359-373 and Segura et al 2002 Clin. Exp. Immunol. 127(2) 243-254).

FIG. 14 illustrates the significant inhibition of LPS-stimulated release of IL-8 from THP-1 cells in culture by pretreatment with either EGF-$LH_N$/C (SXN 100501) or with EGF-$LH_N$/B (SXN 100328).

This result shows clearly the ability of fusion proteins to inhibit the pro-inflammatory cytokine secretory activity of a non-neuronal immune cell type that is a model for the monocyte cell which participates in inflammation.

Methods

THP-1, cells were pre-incubated with 10 nM compound or vehicle control for 48 hours at 37° C./5% $CO_2$. After the pre-incubation, LPS was added at a final concentration of 1 mg/ml and the cells incubated for a further 16 hours (overnight). For inhibitory controls; cells were treated with Staurosporine (1 μM) or Dexamethasone (1 μM) for 30 minutes prior to adding the LPS, and then incubated for 16 hours (overnight). Culture supernatant from each well was harvested and analyzed for cytokine by Luminex-based technology (BioSource). All estimations were performed in triplicate.

Example 18

Activity of EGF-$LH_N$/C and EGF-$LH_N$/B in RPMI Immune Cells

The RPMI-8226 cell line is a human-derived culture that is used frequently to provide a model system for primary B-lymphocytes. It is a well characterized model and over 250 reviewed publications have utilized the RPMI-8226 line to investigate molecular and cellular processes. Recent studies have demonstrated the utility of the RPMI-8226 cell line as a model to assess the secretion of cytokines (Xu et. al. J. Leukoc. Biol. 2002, 72(2) 410-416 and Gupta et. al. 2001, 15(12) 1950-1961).

FIG. 15 illustrates the significant inhibition of LPS-stimulated release of IL-10 from RPMI-8226 cells in culture by pretreatment with either EGF-$LH_N$/C (SXN 100501) or with EGF-$LH_N$/B (SXN 100328).

This result shows clearly the ability of fusion proteins to inhibit the cytokine secretory activity of a non-neuronal immune cell type that is a model for the B-lymphocyte cell which participates in immune responses.

Methods

RPMI-8226 cells were pre-incubated with 10 nM compound or vehicle control for 48 hours at 37° C./5% $CO_2$. After the pre-incubation, LPS was added at a final concentration of 1 mg/ml and the cells incubated for a further 16 hours (overnight). For inhibitory controls; cells were treated with Staurosporine (1 µM) or Dexamethasone (1 µM) for 30 minutes prior to adding the LPS, and then incubated for 16 hours (overnight). Culture supernatant from each well was harvested and analyzed for cytokine by Luminex-based technology (BioSource). All estimations were performed in triplicate.

Example 19

Activity of EGF-LH$_N$/C, CP-RGD-LH$_N$/C and EGF-LH$_N$/B in Human PBMC Immune Cells PBMC are peripheral blood mononuclear cells providing a primary culture that is highly diverse in constituent cell phenotype. It is a well characterized model and over 3000 reviewed publications have utilized primary human PBMC to investigate molecular and cellular processes. Recent studies have demonstrated the utility of human PBMC as a model to assess the secretion of cytokines (Bachmann et. al. Cell Microbiol. 2006, 8(2) 289-300, Siejka et. al. Endocr. Regul. 2005, 39(1) 7-11, Reddy et. al. 2004, 293(1-2) 127-142).

FIG. 16 illustrates the significant inhibition of LPS-stimulated release of IL-8 from human PBMC cells in culture by pretreatment with CP-RGD-LH$_N$/C (SXN 100221), EGF-LH$_N$/C (SXN 100501) or with EGF-LH$_N$/B (SXN 100328).

This result shows clearly the ability of fusion proteins to inhibit the cytokine secretory activity of non-neuronal human immune cells which participates in immune responses.

Methods

PBMC cells were pre-incubated with 10 nM compound or vehicle control for 24 hours at 37° C./5% $CO_2$. After the pre-incubation, LPS was added at a final concentration of 1 mg/ml and the cells incubated for a further 16 hours (overnight). For inhibitory controls; cells were treated with Staurosporine (1 µM) or Dexamethasone (1 µM) for 30 minutes prior to adding the LPS, and then incubated for 16 hours (overnight). Culture supernatant from each well was harvested and analyzed for cytokine by Luminex-based technology (BioSource). All estimations were performed in triplicate.

Example 20

Activity of EGF-LH$_N$/C, CP-RGD-LH$_N$/C and EGF-LH$_N$/B in Human PBMC Immune Cells PBMC are peripheral blood mononuclear cells providing a primary culture that is highly diverse in constituent cell phenotype. It is a well characterized model and over 3000 reviewed publications have utilized primary human PBMC to investigate molecular and cellular processes. Recent studies have demonstrated the utility of human PBMC as a model to assess the secretion of cytokines (Bachmann et. al. Cell Microbiol. 2006, 8(2) 289-300, Siejka et. al. Endocr. Regul. 2005, 39(1) 7-11, Reddy et. al. 2004, 293(1-2) 127-142).

FIG. 17 illustrates the significant inhibition of PHA-stimulated release of IP-10 from human PBMC cells in culture by pretreatment with CP-RGD-LH$_N$/C (SXN 100221), EGF-LH$_N$/C (SXN 100501) or with EGF-LH$_N$/B (SXN 100328).

This result shows clearly the ability of fusion proteins to inhibit the cytokine secretory activity of non-neuronal human immune cells which participates in immune responses.

Methods

PBMC cells were pre-incubated with 10 nM compound or vehicle control for 24 hours at 37° C./5% $CO_2$. After the pre-incubation, PHA was added at a final concentration of 2 mg/ml and the cells incubated for a further 16 hours (overnight). For inhibitory controls; cells were treated with Staurosporine (1 µM) or Dexamethasone (1 µM) for 30 minutes prior to adding the PHA, and then incubated for 16 hours (overnight). Culture supernatant from each well was harvested and analyzed for cytokine by Luminex-based technology (BioSource). All estimations were performed in triplicate.

Example 21

Clinical Example

A 54 year old male suffering from asthma presents at his GP. Despite daily treatment with his preventer inhaler, the use of his reliever inhaler has increased significantly. The patient presents with difficulty in performing everyday tasks due continued shortness of breath and frequent asthma attacks. The GP prescribes a 6-month course of SXN100501 (as prepared in previous examples) in nebuliser form, 80 µg to be taken monthly. Following discussion with the physician, the patient selects the most appropriate nebuliser for their personal situation from a range of suitable devices. After a single dose of SXN100501 the patient experiences a reduced frequency of attacks and a general improvement in FEV1. Further treatment enhances these parameters further and improves quality of life.

Example 22

Clinical Example

A 26 year old female suffering from seasonal allergic rhinitis (hay fever) presents at her GP. Despite completion of a course of preventer treatment (consisting of daily treatment with flixonase for a period of 3 weeks) and subsequent treatment with OTC anti-histamines, the frequency and severity of rhinitis increases. The GP prescribes a 4-month course of SXN100328 (as prepared in previous examples), 80 µg to be taken monthly in the form of a nasal spray. After a single dose of SXN100328 the patient experiences a reduced frequency of rhinitis and generally improved quality of life. Further treatments continue to decrease the severity of the rhinitis.

SEQ ID LIST

SEQ ID NO:1 DNA sequence of LH$_N$/B
SEQ ID NO:2 DNA sequence of LH$_N$/C
SEQ ID NO:3 DNA sequence of the EGF linker
SEQ ID NO:4 DNA sequence of the EGF-C fusion
SEQ ID NO:5 Protein sequence of the EGF-C fusion
SEQ ID NO:6 DNA sequence of the EGF-B fusion
SEQ ID NO:7 Protein sequence of the EGF-B fusion
SEQ ID NO:8 DNA sequence of the RGD linker
SEQ ID NO:9 DNA sequence of the RGD-C fusion
SEQ ID NO:10 Protein sequence of the RGD-C fusion
SEQ ID NO:11 DNA sequence of the cyclic RGD linker
SEQ ID NO:12 DNA sequence of the cyclic RGD-C fusion
SEQ ID NO:13 Protein sequence of the cyclic RGD-C fusion
SEQ ID NO:14 DNA sequence of the LC/C-RGD-H$_N$/C linker
SEQ ID NO:15 DNA sequence of the LC/C-RGD-H$_N$/C fusion
SEQ ID NO:16 Protein sequence of the LC/C-RGD-H$_N$/C fusion
SEQ ID NO:17 DNA sequence of the fully synthesised LC/C-RGD-H$_N$/C fusion SEQ ID NO:18 Protein sequence of the fully synthesised LC/C-RGD-H$_N$/C fusion
SEQ ID NO:19 DNA sequence of the fully synthesised EGF-LH$_N$/C fusion
SEQ ID NO:20 Protein sequence of the fully synthesised EGF-LH$_N$/C fusion
SEQ ID NO:21 Integrin binding peptide sequence
SEQ ID NO:22 Integrin binding peptide sequence
SEQ ID NO:23 Cyclic RGD peptide
SEQ ID NO:24 Linear integrin binding sequence
SEQ ID NO:25 Cyclic integrin binding sequence

What is claimed is:

1. A method of suppressing hypersecretion from an inflammatory cell in a patient in need thereof, said method comprising;
   administering an effective amount of a modified clostridial neurotoxin to said patient;
   wherein the modified clostridial neurotoxin comprises a clostridial toxin light chain and a clostridial toxin translocation domain in which the neuronal targeting activity of the clostridial neurotoxin has been removed;
   wherein said modified clostridial neurotoxin is covalently linked to a ligand that binds to a receptor on an inflammatory cell;
   wherein the inflammatory cell is an inflammatory cell selected from the group consisting of a mast cell, an eosinophil, a macrophage, a monocyte, a neutrophil, and a fibroblast; and
   wherein upon binding of the ligand to a receptor on an inflammatory cell, the light chain is translocated into the cytosol of the cell by the translocation domain and cleaves one or more SNARE proteins essential to exocytosis in the cell.

2. The method according to claim 1, wherein the modified clostridial neurotoxin comprises a clostridial neurotoxin in which the $H_C$ binding ability of the clostridial neurotoxin has been removed.

3. The method according to claim 1, wherein said clostridial toxin translocation domain is provided by a clostridial neurotoxin H-chain having a carboxy-terminal half and an amino-terminal half, wherein the neuronal targeting activity of the carboxy-terminal half of the H-chain has been removed.

4. The method according to claim 1, wherein said clostridial toxin translocation domain comprises the amino-terminal half of a clostridial neurotoxin H-chain.

5. The method according to claim 1, wherein said clostridial neurotoxin L-chain and said clostridial toxin translocation domain are present in the form of a di-chain in which the clostridial neurotoxin L-chain is covalently bonded to the clostridial toxin translocation domain.

6. The method according to claim 1, wherein the patient suffers from an allergy or asthma.

* * * * *